US011795202B2

(12) United States Patent
Griffioen et al.

(10) Patent No.: US 11,795,202 B2
(45) Date of Patent: Oct. 24, 2023

(54) FUSION POLYPEPTIDE COMPRISING A FOREIGN ANTIGEN AND SELF ANTIGEN

(71) Applicant: STICHTING VUMC, Amsterdam (NL)

(72) Inventors: Arjan Willem Griffioen, Amsterdam (NL); Elisabeth Johanna Maria Huijbers, Amsterdam (NL); Patrycja Nowak-Sliwinska, Amsterdam (NL)

(73) Assignee: STICHTING VUMC, Amsterdam (NL)

( * ) Notice: Subject to any disclaimer, the term of this patent is extended or adjusted under 35 U.S.C. 154(b) by 840 days.

(21) Appl. No.: 16/322,786

(22) PCT Filed: Aug. 4, 2017

(86) PCT No.: PCT/NL2017/050526
§ 371 (c)(1),
(2) Date: Feb. 1, 2019

(87) PCT Pub. No.: WO2018/026283
PCT Pub. Date: Feb. 8, 2018

(65) Prior Publication Data
US 2020/0017564 A1    Jan. 16, 2020

(30) Foreign Application Priority Data
Aug. 4, 2016   (EP) .................................... 16182827

(51) Int. Cl.
| *A61K 39/00* | (2006.01) |
| *C07K 14/47* | (2006.01) |
| *A61P 35/00* | (2006.01) |
| *C07K 14/245* | (2006.01) |
| *C07K 14/78* | (2006.01) |
| *C07K 16/18* | (2006.01) |
| *C12N 15/62* | (2006.01) |
| *C12Q 1/6886* | (2018.01) |

(52) U.S. Cl.
CPC ...... *C07K 14/4748* (2013.01); *A61K 39/0011* (2013.01); *A61P 35/00* (2018.01); *C07K 14/245* (2013.01); *C07K 14/78* (2013.01); *C07K 16/18* (2013.01); *C12N 15/62* (2013.01); *C12Q 1/6886* (2013.01); *A61K 2039/55566* (2013.01); *A61K 2039/585* (2013.01); *A61K 2039/6068* (2013.01); *C07K 2319/21* (2013.01); *C07K 2319/35* (2013.01); *C12Q 2600/106* (2013.01); *C12Q 2600/112* (2013.01)

(58) Field of Classification Search
None
See application file for complete search history.

(56) References Cited

U.S. PATENT DOCUMENTS

2002/0115827 A1* 8/2002 Kim .................... C12N 9/0036
530/350
2011/0293621 A1* 12/2011 Mueller ............... A61K 39/385
424/139.1

FOREIGN PATENT DOCUMENTS

CN         1189539 A  *  8/1998
WO    WO2011/151721 A1    12/2011

OTHER PUBLICATIONS

Henderson, Emily; "Reserchers identify new targets to control angiogenesis." News Medical and Life Sciences (2021).*
Nicosia, Roberto F. et al; "Fibronectin promotes the elongation of microvesssels during angiogenesis in vivo." J. Cell. Physiol. (1993) 154 p. 654-661.*
Brentville, Victoria A. et al; "Cirtullinated vimentin presented on MHC-II in tumor cells is a target for cd4+ t cell mediated antitumor immunity." Cancer Res. (2016) 76(3) p. 548-561.*
Bergmann-Leitner, Elke S. and Leitner, Wolfgang W.; "Adjuvants in the driver's seat: how magnitude, type, fine specificity and longevity of immune responses are driven by distinct classes of immune potentiators." Vaccines (2014) 2 p. 252-296.*
Singh, Bhagirath et al; "Minimum peptide sequences necessary for priming and triggering of humoral and cell mediated immune responses in mice: use of synthetic peptide antigens of defined structure." J. Immunol. (1980) 124(3) p. 1336-1343.*
Yampolsky, Lev Y. and Stoltzfus, Arlin; "The exchangeability of amino acids in proteins." Genetics (2005) 170 p. 1459-1472.*
Machine translation of CN-1189539A.*
Huijbers, et. al., "Vaccination against the extra domain-B of fibronectin as a novel tumor therapy", The FASEB Journal, vol. 24, Nov. 2010, pp. 4535-4544.
Griffioen, Arjan J., "Genomic screening of the Embryo for Novel targets in the tumor Endothelium", Marie Curie Intra-European Fellowships (IEF), Final Project Report under Grant Agreement No. 328695, May 1, 2013 to Apr. 30, 2015, www.mcgene.eu.
Saupe, et. al., "Vaccines targeting self-antigens; mechanisms and efficacy-determining parameters", The FASEB Journal, vol. 29, No. 8, Jan. 2017, pp. 3253-3262.
International Search Report and Written Opinion regarding International App. No. PCT/NL2017/050526, dated Nov. 24, 2017.
International Preliminary Report on Patentability regarding International App. No. PCT/NL2017/050526, dated Feb. 5, 2019.
European Search Report and Written Opinion regarding European App. No. 16182827, dated Jan. 12, 2017.
European Office Action regarding European App. No. 17754837.7, dated Dec. 10, 2019.
European Office Action regarding European App. No. 17754837.7, dated Jun. 12, 2020.

(Continued)

*Primary Examiner* — Fred H Reynolds
(74) *Attorney, Agent, or Firm* — DENTONS US LLP

(57) ABSTRACT

The invention is in the field of medicine. More specifically, it is in the field of diagnosing tumor angiogenesis status and in the field of medical treatment of a subject who is suffering, suspected to suffer, or might suffer from a tumor in the future. In particular, the invention relates to a fusion polypeptide comprising a foreign antigen and a self antigen, wherein said foreign antigen consists of a polypeptide comprising an amino acid sequence of at least 12-15 amino acid residues, 12-24% of which residues are hydrophilic, bulky amino acid residues selected from the group consisting of histidine, glutamate, arginine, glutamine, aspartic acid and/or lysine.

20 Claims, 45 Drawing Sheets
Specification includes a Sequence Listing.

(56) References Cited

OTHER PUBLICATIONS

European Office Action regarding European App. No. 17754837.7, dated Nov. 2, 2020.
European Office Action regarding European App. No. 17754837.7, dated Jul. 26, 2021.

* cited by examiner

Figure 9

| Ensembl ID | Gene ID mouse | Gene ID human | Name | GenBank accession no. | Human ortholog |
|---|---|---|---|---|---|
| ENSMUSG00000026728 | 22352 | 7431 | Vim | NP_035831.2, NM_011701.4 | NP_003371.2, NM_003380.3 |
|  | 673094 | 4267 | CD99 | NP_079860.2, NM_025584.2 | NP_001264639.1, NM_001277710.1 |

Figure 10

| Ensembl ID | Gene ID mouse | Gene ID human | Name | GenBank accession no. | Human ortholog |
|---|---|---|---|---|---|
| ENSMUSG00000027435 | 17064 | 22918 | Cd93 | NP_034870.1, NM_010740.3 | NP_036204.2, NM_012072.3 |

Figure 11

| Ensembl ID | Gene ID mouse | Gene ID human | Name | GenBank accession no. | Human ortholog |
|---|---|---|---|---|---|
| ENSMUSG00000000957 | 17387 | 4323 | Mmp14 | NP_032634.3, NM_008608.3 | NP_004986.1, NM_004995.3 |
| ENSMUSG00000039787 | 99151 | 51148 | Cercam | NP_997181.1, NM_207298.2 | NM_001286760.1, NP_001273689.1 |
| ENSMUSG00000016918 | 240725 | 23213 | Sulf1 | NP_001185494.1, NM_001198565.1 | NP_055985.2, NM_015170.2 |
| ENSMUSG00000044017 | 243277 | 283383 | Gpr133 | NP_001074811.1, NM_001081342.1 | NP_942122.2, NM_198827.3 |
| ENSMUSG00000034463 | 219151 | 51435 | Scara3 | NP_766192.1, NM_172604.3 | NP_878185.1, NM_182826.1 |
| ENSMUSG00000005534 | 16337 | 3643 | Insr | NP_034698.2, NM_010568.2 | NP_001073285.1, NM_001079817.1 |
| ENSMUSG00000001773 | 53320 | 219595 | Folh1 | NP_001153178.1, NM_001159706.1 | NP_710163.1, NM_153696.2 |
|  | 673094 | 4267 | CD99 | NP_079860.2, NM_025584.2 | NP_001264639.1, NM_001277710.1 |
| ENSMUSG00000000530 | 11482 | 94 | Acvrl1 | NP_001264188.1, NM_001277259.1 | NP_000011.2, NM_000020.2 |
| ENSMUSG00000026768 | 241226 | 8516 | Itga8 | NP_001001309.1, NM_001001309.2 | NP_001278423.1, NM_001291494.1 |
| ENSMUSG00000050808 | 269328 | 143662 | Muc15 | NP_766567.1, NM_172979.3 | NP_001128564.1, NM_001135092.1 |
| ENSMUSG00000018166 | 13867 | 2065 | Erbb3 | NP_034283.1, NM_010153.1 | NP_001973.2 and NM_001982.3 |

Figure 11 (continued)

| ENSMUSG00000062312 | 13866 | 2064 | Erbb2 | NP_001003817.1, NM_001003817.1 | NP_001276865.1, NM_001289936.1, NP_001005862.1, NM_001005862.2, NP_001276867.1, NM_001289938.1 |

Figure 12

| Ensembl ID | Gene ID mouse | Gene ID human | Name | GenBank accession no. | Human ortholog |
|---|---|---|---|---|---|
| ENSMUSG00000001131 | 21857 | 7076 | Timp1 | NM_001044384.1 | NM_003254.2 |
| ENSMUSG00000037010 | 30878 | 8862 | Apln | NM_013912.3 | NM_017413.4 |
| ENSMUSG00000040026 | 20210 | | Saa3 | NM_011315.3 | S73444.1 |
| ENSMUSG00000027832 | 19288 | 5806 | Ptx3 | NP_033013.3, NM_008987.3 | NP_002843.2, NM_002852.3 |
| ENSMUSG00000053475 | 21930 | 7130 | Tnfaip6 | NP_033424.1, NM_009398.2 | NP_009046.2, NM_007115.3 |
| ENSMUSG00000036596 | 242939 | 8532 | Cpz | NP_694747.2, NM_153107.2 | NP_003643.2, NM_003652.3, NP_001014447.1, NM_001014447.2, NP_001014448.1, NM_001014448.2 |
| ENSMUSG00000025359 | 20431 | 6490 | Pmel | NP_068682.2, NM_021882.4, XP_006513468.1, XM_006513405.2 | NP_001186983.1, NM_001200054.1, NP_001186982.1, NM_001200053.1 |
| ENSMUSG00000036412 | 545260 | 340075 | Arsi | NP_001033588.1, NM_001038499.1 | NP_001012301.1, NM_001012301.2 |
| ENSMUSG00000006403 | 240913 | 9507 | Adamts4 | NM_172845.2 | NP_005090.3, NM_005099.4 |
| ENSMUSG00000023885 | 21826 | 7058 | Thbs2 | NP_035711.2, NM_011581.3 | NP_003238.2, NM_003247.3 |
| ENSMUSG00000000957 | 17387 | 4323 | Mmp14 | NP_032634.3, NM_008608.3 | NP_004986.1, NM_004995.3 |
| ENSMUSG00000020427 | 16009 | 3486 | Igfbp3 | NP_032369.2, NM_008343.2 | NP_001013416.1, NM_001013398.1, NP_000589.2, NM_000598.4 |

Figure 12 (continued)

| | | | | | |
|---|---|---|---|---|---|
| ENSMUSG00000040152 | 21825 | 7057 | Thbs1 | NP_035710.2, NM_011580.3 | NP_003237.2, NM_003246.2 |
| ENSMUSG00000027204 | 14118 | 2200 | Fbn1 | NP_032019.2, NM_007993.2 | NP_000129.3, NM_000138.4 |
| ENSMUSG00000027750 | 50706 | 10631 | Postn | NP_001185695.1, NM_001198766.1 | NP_001273596.1, NM_001286667.1 |
| ENSMUSG00000000693 | 16950 | 84695 | Loxl3 | NP_038614.2, NM_013586.4 | NP_001276093.1, NM_001289164.1 |
| ENSMUSG00000030116 | 50530 | 8076 | Mfap5 | NM_015776.2, NP_056591.1 | NP_001284639.1, NM_001297710.1 |
| ENSMUSG00000024909 | 58859 | 30008 | Efemp2 | NM_001164352.1, NP_001157824.1 | NP_058634.4, NM_016938.4 |
| ENSMUSG00000037362 | 18133 | 4856 | Nov | NP_035060.1, NM_010930.4 | NP_002505.1, NM_002514.3 |
| ENSMUSG00000021614 | 13003 | 1462 | Vcan | NP_001127947.1, NM_001134475.1 | NP_004376.2, NM_004385.4 |
| ENSMUSG00000029675 | 13717 | 2006 | Eln | NP_031951.2, NM_007925.3 | NP_001075223.1, NM_001081754.2 |
| ENSMUSG00000028195 | 16007 | 3491 | Cyr61 | NP_034646.1, NM_010516.2 | NP_001545.2, NM_001554.4 |
| ENSMUSG00000016918 | 240725 | 23213 | Sulf1 | NP_001185494.1, NM_001198565.1 | NP_055985.2, NM_015170.2 |
| ENSMUSG00000021806 | 18074 | 22795 | Nid2 | NP_032721.2, NM_008695.2 | NP_031387.3, NM_007361.3 |
| ENSMUSG00000019846 | 16775 | 3910 | Lama4 | NP_034811.2, NM_010681.4 | NP_002281.3, NM_002290.4 |
| ENSMUSG00000056427 | 20564 | 6586 | Slit3 | NP_035542.2, NM_011412.3 | NP_003053.1, NM_003062.3 |

Figure 12 (continued)

| | | | | | |
|---|---|---|---|---|---|
| ENSMUSG00000020695 | 17534 | 9902 | Mrc2 | NP_032652.3, NM_008626.3 | NP_006030.2, NM_006039.4 |
| ENSMUSG00000062345 | 18788 | 5055 | Serpinb2 | NM_001174170.1, NP_001167641.1 | NP_001137290.1, NM_001143818.1 |
| ENSMUSG00000035385 | 20296 | 6347 | Ccl2 | NP_035463.1, NM_011333.3 | NP_002973.1, NM_002982.3 |
| | 673094 | 4267 | CD99 | NP_079860.2, NM_025584.2 | NP_001264639.1, NM_001277710.1 |
| ENSMUSG00000039304 | 22035 | 8743 | Tnfsf10 | NP_033451.1, NM_009425.2 | NP_001177871.1, NM_001190942.1 |
| ENSMUSG00000022991 | 16770 | 3906 | Lalba | NP_034809.1, NM_010679.1 | NP_002280.1, NM_002289.2 |

Figure 13

| Ensembl ID | Gene ID mouse | Gene ID human | Name | GenBank accession no. | Human ortholog |
|---|---|---|---|---|---|
| ENSMUSG00000037010 | 30878 | 8862 | Apln | NM_013912.3 | NM_017413.4 |
| ENSMUSG00000040026 | 20210 | | Saa3 | NM_011315.3 | S73444.1 |
| ENSMUSG00000026728 | 22352 | 7431 | Vim | NP_035831.2, NM_011701.4 | NP_003371.2, NM_003380.3 |
| ENSMUSG00000025359 | 20431 | 6490 | Pmel | NP_068682.2, NM_021882.4, XP_006513468.1, XM_006513405.2 | NP_001186983.1, NM_001200054.1, NP_001186982.1, NM_001200053.1 |
| ENSMUSG00000036412 | 545260 | 340075 | Arsi | NP_001033588.1, NM_001038499.1 | NP_001012301.1, NM_001012301.2 |
| ENSMUSG00000005124 | 22402 | 8840 | Wisp1 | NP_061353.1, NM_018865.2 | NP_001191799.1, NM_001204870.1 |
| ENSMUSG00000001555 | 14230 | 60681 | Fkbp10 | NP_038557.1, NM_013529.3 | NM_021939.3, NP_068758.3 |

Figure 14

| Ensembl ID | Gene ID mouse | Gene ID human | Name | GenBank accession no. | Human ortholog |
|---|---|---|---|---|---|
| ENSMUSG00000001131 | 21857 | 7076 | Timp1 | NM_001044384.1 | NM_003254.2 |
| ENSMUSG00000037010 | 30878 | 8862 | Apln | NM_013912.3 | NM_017413.4 |
| ENSMUSG00000040026 | 20210 | | Saa3 | NM_011315.3 | S73444.1 |
| ENSMUSG00000027832 | 19288 | 5806 | Ptx3 | NP_033013.3, NM_008987.3 | NP_002843.2, NM_002852.3 |
| ENSMUSG00000026728 | 22352 | 7431 | Vim | NP_035831.2, NM_011701.4 | NP_003371.2, NM_003380.3 |
| ENSMUSG00000053475 | 21930 | 7130 | Tnfaip6 | NP_033424.1, NM_009398.2 | NP_009046.2, NM_007115.3 |
| ENSMUSG00000036596 | 242939 | 8532 | Cpz | NP_694747.2, NM_153107.2 | NP_003643.2, NM_003652.3, NP_001014447.1, NM_001014447.2, NP_001014448.1, NM_001014448.2 |
| ENSMUSG00000036412 | 545260 | 340075 | Arsi | NP_001033588.1, NM_001038499.1 | NP_001012301.1, NM_001012301.2 |
| ENSMUSG00000042379 | 71690 | 11082 | Esm1 | NP_076101.1, NM_023612.3 | NP_008967.1, NM_007036.4, NP_001129076.1, NM_001135604.1 |
| ENSMUSG00000000555 | 16402 | 3678 | Itga5 | NP_034707.3, NM_010577.3 | NP_002196.2, NM_002205.2 |
| ENSMUSG00000036545 | 216725 | 9509 | Adamts 2 | NP_001264234.1, NM_001277305.1, NP_783574.1, NM_175643.3 | NP_067610.1, NM_021599.2, NP_055059.2, NM_014244.4 |
| ENSMUSG00000023885 | 21826 | 7058 | Thbs2 | NP_035711.2, NM_011581.3 | NP_003238.2, NM_003247.3 |

Figure 14 (continued)

| | | | | | |
|---|---|---|---|---|---|
| ENSMUSG00000000957 | 17387 | 4323 | Mmp14 | NP_032634.3, NM_008608.3 | NP_004986.1, NM_004995.3 |
| ENSMUSG00000040152 | 21825 | 7057 | Thbs1 | NP_035710.2, NM_011580.3 | NP_003237.2, NM_003246.2 |
| ENSMUSG00000027204 | 14118 | 2200 | Fbn1 | NP_032019.2, NM_007993.2 | NP_000129.3, NM_000138.4 |
| ENSMUSG00000027750 | 50706 | 10631 | Postn | NP_001185695.1, NM_001198766.1 | NP_001273596.1, NM_001286667.1 |
| ENSMUSG00000024598 | 14119 | 2201 | Fbn2 | NP_034311.2, NM_010181.2 | NP_001990.2, NM_001999.3 |
| ENSMUSG00000039787 | 99151 | 51148 | Cercam | NP_997181.1, NM_207298.2 | NM_001286760.1, NP_001273689.1 |
| ENSMUSG00000000693 | 16950 | 84695 | Loxl3 | NP_038614.2, NM_013586.4 | NP_001276093.1, NM_001289164.1 |
| ENSMUSG00000030116 | 50530 | 8076 | Mfap5 | NM_015776.2, NP_056591.1 | NP_001284639.1, NM_001297710.1 |
| ENSMUSG00000024909 | 58859 | 30008 | Efemp2 | NM_001164352.1, NP_001157824.1 | NP_058634.4, NM_016938.4 |
| ENSMUSG00000037362 | 18133 | 4856 | Nov | NP_035060.1, NM_010930.4 | NP_002505.1, NM_002514.3 |
| ENSMUSG00000021614 | 13003 | 1462 | Vcan | NP_001127947.1, NM_001134475.1 | NP_004376.2, NM_004385.4 |
| ENSMUSG00000029675 | 13717 | 2006 | Eln | NP_031951.2, NM_007925.3 | NP_001075223.1, NM_001081754.2 |
| ENSMUSG00000028195 | 16007 | 3491 | Cyr61 | NP_034646.1, NM_010516.2 | NP_001545.2, NM_001554.4 |
| ENSMUSG00000016918 | 240725 | 23213 | Sulf1 | NP_001185494.1, NM_001198565.1 | NP_055985.2, NM_015170.2 |

Figure 14 (continued)

| | | | | | |
|---|---|---|---|---|---|
| ENSMUSG00000021806 | 18074 | 22795 | Nid2 | NP_032721.2, NM_008695.2 | NP_031387.3, NM_007361.3 |
| ENSMUSG00000019846 | 16775 | 3910 | Lama4 | NP_034811.2, NM_010681.4 | NP_002281.3, NM_002290.4 |
| ENSMUSG00000056427 | 20564 | 6586 | Slit3 | NP_035542.2, NM_011412.3 | NP_003053.1, NM_003062.3 |
| ENSMUSG00000020695 | 17534 | 9902 | Mrc2 | NP_032652.3, NM_008626.3 | NP_006030.2, NM_006039.4 |
| ENSMUSG00000044017 | 243277 | 283383 | Gpr133 | NP_001074811.1, NM_001081342.1 | NP_942122.2, NM_198827.3 |
| ENSMUSG00000034463 | 219151 | 51435 | Scara3 | NP_766192.1, NM_172604.3 | NP_878185.1, NM_182826.1 |
| ENSMUSG00000005534 | 16337 | 3643 | Insr | NP_034698.2, NM_010568.2 | NP_001073285.1, NM_001079817.1 |
| ENSMUSG00000001773 | 53320 | 219595 | Folh1 | NP_001153178.1, NM_001159706.1 | NP_710163.1, NM_153696.2 |
| | 673094 | 4267 | CD99 | NP_079860.2, NM_025584.2 | NP_001264639.1, NM_001277710.1 |
| ENSMUSG00000000530 | 11482 | 94 | Acvrl1 | NP_001264188.1, NM_001277259.1 | NP_000011.2, NM_000020.2 |
| ENSMUSG00000029675 | 13717 | 2006 | Eln | NP_031951.2, NM_007925.3 | NP_001075223.1, NM_001081754.2 |
| ENSMUSG00000026768 | 241226 | 8516 | Itga8 | NP_001001309.1, NM_001001309.2 | NP_001278423.1, NM_001291494.1 |
| ENSMUSG00000039304 | 22035 | 8743 | Tnfsf10 | NP_033451.1, NM_009425.2 | NP_001177871.1, NM_001190942.1 |
| ENSMUSG00000022991 | 16770 | 3906 | Lalba | NP_034809.1, NM_010679.1 | NP_002280.1, NM_002289.2 |

Figure 14 (continued)

| | | | | | |
|---|---|---|---|---|---|
| ENSMUSG00000050808 | 269328 | 143662 | Muc15 | NP_766567.1, NM_172979.3 | NP_001128564.1, NM_001135092.1 |
| ENSMUSG00000018166 | 13867 | 2065 | Erbb3 | NP_034283.1, NM_010153.1 | NP_001973.2 and NM_001982.3 |
| ENSMUSG00000062312 | 13866 | 2064 | Erbb2 | NP_001003817.1, NM_001003817.1 | NP_001276865.1, NM_001289936.1, NP_001005862.1, NM_001005862.2, NP_001276867.1, NM_001289938.1 |

Figure 15

| Ensembl ID | Gene ID mouse | Gene ID human | Name | GenBank accession no. | Human ortholog |
|---|---|---|---|---|---|
| ENSMUSG00000027435 | 17064 | 22918 | Cd93 | NP_034870.1, NM_010740.3 | NP_036204.2, NM_012072.3 |
| ENSMUSG00000075254 | 77446 | 57493 | Heg1 | NP_780465.4, NM_175256.5 | NP_065784.1, NM_020733.1 |
| ENSMUSG00000015468 | 18132 | 4855 | Notch4 | NP_035059.2, NM_010929.2 | NP_004548.3, NM_004557.3 |
| ENSMUSG00000044338 | 23796 | 187 | Aplnr | NP_035914.1, NM_011784.3 | NP_005152.1, NM_005161.4, NR_027991.1 |
| ENSMUSG00000004891 | 18008 | 10763 | Nes | NP_057910.3, NM_016701.3 | NP_006608.1, NM_006617.1 |
| ENSMUSG00000028364 | 21923 | 3371 | Tnc | NP_035737.2, NM_011607.3 | NP_002151.2, NM_002160.3 |
| ENSMUSG00000042821 | 20613 | 6615 | Snai1 | NP_035557.1, NM_011427.2 | NP_005976.2, NM_005985.3 |
| ENSMUSG00000028597 | 67305 | 2882 | Gpx7 | NP_077160.1, NM_024198.3 | NM_015696.4 |
| ENSMUSG00000039883 | 74511 | 10234 | Lrrc17 | NP_083253.1, NM_028977.1 | NP_005815.2, NM_005824.2 |
| ENSMUSG00000021319 | 20379 | 6424 | Sfrp4 | NP_057896.1, NM_016687.3 | NP_003005.2, NM_003014.3 |
| ENSMUSG00000022440 | 72709 | 114904 | C1qtnf6 | NM_001204153.1, NP_001191082.1 | NM_031910.3, NP_114116.3 |
| ENSMUSG00000036334 | 242050 | 285313 | Igsf10 | NP_001156356.1, NM_001162884.1 | NM_001178145.1, NP_001171616.1 |

Figure 15 (continued)

| | | | | | |
|---|---|---|---|---|---|
| ENSMUSG00000027996 | 20319 | 6423 | Sfrp2 | NP_033170.1, NM_009144.2 | NP_003004.1, NM_003013.2 |
| ENSMUSG00000020363 | 14584 | 9945 | Gfpt2 | NP_038557.1, NM_013529.3 | NP_005101.1, NM_005110.2 |
| ENSMUSG00000027408 | 56264 | 56265 | Cpxm1 | NP_062670.2, NM_019696.2 | NP_001171628.1, NM_001184699.1 |
| ENSMUSG00000056481 | 70445 | 57124 | Cd248 | NP_473383.1, NM_054042.2 | NP_065137.1, NM_020404.2 |
| ENSMUSG00000034205 | 94352 | | Loxl2 | NP_201582.2, NM_033325.2 | |
| ENSMUSG00000022816 | 14314 | 11167 | Fstl1 | NP_032073.2, NM_008047.5 | NP_009016.1, NM_007085.4 |
| ENSMUSG00000028369 | 64817 | 79987 | Svep1 | NP_073725.2, NM_022814.2 | NP_699197.3, NM_153366.3 |
| ENSMUSG00000046841 | 216197 | 10970 | Ckap4 | NP_780660.1, NM_175451.1 | NP_006816.2, NM_006825.3 |
| ENSMUSG00000024053 | 246707 | 84034 | Emilin2 | NP_660140.1, NM_145158.3 | NP_114437.2, NM_032048.2 |
| ENSMUSG00000001622 | 12994 | 1448 | Csn3 | NP_031812.2, NM_007786.4 | NP_005203.2, NM_005212.2 |
| ENSMUSG00000059588 | 54598 | 10203 | Calcrl | NP_061252.2, NM_018782.2 | NP_001258680.1, NM_001271751.1 |
| ENSMUSG00000028859 | 12986 | 1441 | Csf3r | NP_031808.2, NM_007782.3 | NP_758519.1, NM_172313.2 |
| ENSMUSG00000028262 | 80797 | | Clca2 | NP_085104.1, NM_030601.3 | |
| ENSMUSG00000045930 | 66864 | 161198 | Clec14a | NP_080085.3, NM_025809.5 | NP_778230.1, NM_175060.2 |

Figure 15 (continued)

| | | | | | |
|---|---|---|---|---|---|
| ENSMUSG00000069763 | 67888 | 55273 | Tmem100 | NP_080709.1, NM_026433.2 | NP_001093110.1, NM_001099640.1 |
| ENSMUSG00000041134 | 224405 | 116159 | Cyyr1 | NP_659102.1, NM_144853.3 | NP_443186.1, NM_052954.2 |
| ENSMUSG00000038007 | 230379 | 340485 | Acer2 | NP_001277472.1, NM_001290543.1 | NP_001010887.2, NM_001010887.2 |
| ENSMUSG00000038679 | 83925 | 7227 | Trps1 | NP_114389.2, NM_032000.2 | NP_054831.2, NM_014112.4 |
| ENSMUSG00000024451 | 106952 | 64411 | Arap3 | NP_001192265.1, NM_001205336.1 | NP_071926.4, NM_022481.5 |
| ENSMUSG00000021904 | 218877 | 56920 | Sema3g | NP_001020550.1, NM_001025379.1 | NP_064548.1, NM_020163.1 |
| ENSMUSG00000024754 | 83921 | 23670 | Tmem2 | NP_001028931.1, NM_001033759.2 | NP_001129292.1, NM_001135820.1 |
| ENSMUSG00000059325 | 74318 | 84525 | Hopx | NP_783199.1, NM_175606.3 | NP_001138932.1, NM_001145460.1 |
| ENSMUSG00000048960 | 109294 | 80243 | Prex2 | NP_083801.1, NM_029525.1 | NP_079146.2, NM_024870.2 |
| ENSMUSG00000037846 | 170799 | 219790 | Rtkn2 | NP_001074815.1, NM_001081346.1 | NP_660350.2, NM_145307.3 |
| ENSMUSG00000076431 | 20677 | 6659 | Sox4 | NP_033264.2, NM_009238.2 | NP_003098.1, NM_003107.2 |
| ENSMUSG00000027217 | 241556 | 90139 | Tspan18 | NP_899003.1, NM_183180.2 | NP_570139.3, NM_130783.4 |
| ENSMUSG00000039116 | 215798 | 57211 | Gpr126 | NP_001002268.1, NM_001002268.3 | NP_065188.4, NM_020455.5 |
| ENSMUSG00000033082 | 243653 | 51267 | Clec1a | NP_780735.2, NM_175526.3 | NP_001284678.1, NM_001297749.1 |

Figure 15 (continued)

| ENSMUSG00000040289 | 15213 | 23462 | Hey1 | NP_034553.2, NM_010423.2 | NP_036390.3, NM_012258.3 |

Figure 16

| Ensembl ID | Gene ID mouse | Gene ID human | Name | GenBank accession no. | Human ortholog |
|---|---|---|---|---|---|
| ENSMUSG00000001131 | 21857 | 7076 | Timp1 | NM_001044384.1 | NM_003254.2 |
| ENSMUSG00000037010 | 30878 | 8862 | Apln | NM_013912.3 | NM_017413.4 |
| ENSMUSG00000040026 | 20210 | | Saa3 | NM_011315.3 | S73444.1 |
| ENSMUSG00000027435 | 17064 | 22918 | Cd93 | NP_034870.1, NM_010740.3 | NP_036204.2, NM_012072.3 |
| ENSMUSG00000075254 | 77446 | 57493 | Heg1 | NP_780465.4, NM_175256.5 | NP_065784.1, NM_020733.1 |
| ENSMUSG00000015468 | 18132 | 4855 | Notch4 | NP_035059.2, NM_010929.2 | NP_004548.3, NM_004557.3 |
| ENSMUSG00000044338 | 23796 | 187 | Aplnr | NP_035914.1, NM_011784.3 | NP_005152.1, NM_005161.4, NR_027991.1 |
| ENSMUSG00000004891 | 18008 | 10763 | Nes | NP_057910.3, NM_016701.3 | NP_006608.1, NM_006617.1 |
| ENSMUSG00000028364 | 21923 | 3371 | Tnc | NP_035737.2, NM_011607.3 | NP_002151.2, NM_002160.3 |
| ENSMUSG00000027832 | 19288 | 5806 | Ptx3 | NP_033013.3, NM_008987.3 | NP_002843.2, NM_002852.3 |
| ENSMUSG00000026728 | 22352 | 7431 | Vim | NP_035831.2, NM_011701.4 | NP_003371.2, NM_003380.3 |
| ENSMUSG00000053475 | 21930 | 7130 | Tnfaip6 | NP_033424.1, NM_009398.2 | NP_009046.2, NM_007115.3 |

Figure 16 (continued)

| | | | | | |
|---|---|---|---|---|---|
| ENSMUSG00000036596 | 242939 | 8532 | Cpz | NP_694747.2, NM_153107.2 | NP_003643.2, NM_003652.3, NP_001014447.1, NM_001014447.2, NP_001014448.1, NM_001014448.2 |
| ENSMUSG00000042821 | 20613 | 6615 | Snai1 | NP_035557.1, NM_011427.2 | NP_005976.2, NM_005985.3 |
| ENSMUSG00000025359 | 20431 | 6490 | Pmel | NP_068682.2, NM_021882.4, XP_006513468.1, XM_006513405.2 | NP_001186983.1, NM_001200054.1, NP_001186982.1, NM_001200053.1 |
| ENSMUSG00000036412 | 545260 | 340075 | Arsi | NP_001033588.1, NM_001038499.1 | NP_001012301.1, NM_001012301.2 |
| ENSMUSG00000005124 | 22402 | 8840 | Wisp1 | NP_061353.1, NM_018865.2 | NP_001191799.1, NM_001204870.1 |
| ENSMUSG00000028597 | 67305 | 2882 | Gpx7 | NP_077160.1, NM_024198.3 | NM_015696.4 |
| ENSMUSG00000006403 | 240913 | 9507 | Adamts4 | NM_172845.2 | NP_005090.3, NM_005099.4 |
| ENSMUSG00000042379 | 71690 | 11082 | Esm1 | NP_076101.1, NM_023612.3 | NP_008967.1, NM_007036.4, NP_001129076.1, NM_001135604.1 |
| ENSMUSG00000000555 | 16402 | 3678 | Itga5 | NP_034707.3, NM_010577.3 | NP_002196.2, NM_002205.2 |
| ENSMUSG00000036545 | 216725 | 9509 | Adamts2 | NP_001264234.1, NM_001277305.1, NP_783574.1, NM_175643.3 | NP_067610.1, NM_021599.2, NP_055059.2, NM_014244.4 |
| ENSMUSG00000023885 | 21826 | 7058 | Thbs2 | NP_035711.2, NM_011581.3 | NP_003238.2, NM_003247.3 |
| ENSMUSG00000000957 | 17387 | 4323 | Mmp14 | NP_032634.3, NM_008608.3 | NP_004986.1, NM_004995.3 |
| ENSMUSG00000020427 | 16009 | 3486 | Igfbp3 | NP_032369.2, NM_008343.2 | NP_001013416.1, NM_001013398.1, NP_000589.2, NM_000598.4 |

Figure 16 (continued)

| | | | | | |
|---|---|---|---|---|---|
| ENSMUSG00000040152 | 21825 | 7057 | Thbs1 | NP_035710.2, NM_011580.3 | NP_003237.2, NM_003246.2 |
| ENSMUSG00000027204 | 14118 | 2200 | Fbn1 | NP_032019.2, NM_007993.2 | NP_000129.3, NM_000138.4 |
| ENSMUSG00000027750 | 50706 | 10631 | Postn | NP_001185695.1, NM_001198766.1 | NP_001273596.1, NM_001286667.1 |
| ENSMUSG00000039883 | 74511 | 10234 | Lrrc17 | NP_083253.1, NM_028977.1 | NP_005815.2, NM_005824.2 |
| ENSMUSG00000024598 | 14119 | 2201 | Fbn2 | NP_034311.2, NM_010181.2 | NP_001990.2, NM_001999.3 |
| ENSMUSG00000039787 | 99151 | 51148 | Cercam | NP_997181.1, NM_207298.2 | NM_001286760.1, NP_001273689.1 |
| ENSMUSG00000021319 | 20379 | 6424 | Sfrp4 | NP_057896.1, NM_016687.3 | NP_003005.2, NM_003014.3 |
| ENSMUSG00000022440 | 72709 | 114904 | C1qtnf6 | NM_001204153.1, NP_001191082.1 | NM_031910.3, NP_114116.3 |
| ENSMUSG00000000693 | 16950 | 84695 | Loxl3 | NP_038614.2, NM_013586.4 | NP_001276093.1, NM_001289164.1 |
| ENSMUSG00000036334 | 242050 | 285313 | Igsf10 | NP_001156356.1, NM_001162884.1 | NM_001178145.1, NP_001171616.1 |
| ENSMUSG00000027996 | 20319 | 6423 | Sfrp2 | NP_033170.1, NM_009144.2 | NP_003004.1, NM_003013.2 |
| ENSMUSG00000001555 | 14230 | 60681 | Fkbp10 | NP_038557.1, NM_013529.3 | NM_021939.3, NP_068758.3 |
| ENSMUSG00000020363 | 14584 | 9945 | Gfpt2 | NP_038557.1, NM_013529.3 | NP_005101.1, NM_005110.2 |
| ENSMUSG00000027408 | 56264 | 56265 | Cpxm1 | NP_062670.2, NM_019696.2 | NP_001171628.1, NM_001184699.1 |

Figure 16 (continued)

| | | | | | |
|---|---|---|---|---|---|
| ENSMUSG00000030116 | 50530 | 8076 | Mfap5 | NM_015776.2, NP_056591.1 | NP_001284639.1, NM_001297710.1 |
| ENSMUSG00000024909 | 58859 | 30008 | Efemp2 | NM_001164352.1, NP_001157824.1 | NP_058634.4, NM_016938.4 |
| ENSMUSG00000037362 | 18133 | 4856 | Nov | NP_035060.1, NM_010930.4 | NP_002505.1, NM_002514.3 |
| ENSMUSG00000021614 | 13003 | 1462 | Vcan | NP_001127947.1, NM_001134475.1 | NP_004376.2, NM_004385.4 |
| ENSMUSG00000029675 | 13717 | 2006 | Eln | NP_031951.2, NM_007925.3 | NP_001075223.1, NM_001081754.2 |
| ENSMUSG00000028195 | 16007 | 3491 | Cyr61 | NP_034646.1, NM_010516.2 | NP_001545.2, NM_001554.4 |
| ENSMUSG00000016918 | 240725 | 23213 | Sulf1 | NP_001185494.1, NM_001198565.1 | NP_055985.2, NM_015170.2 |
| ENSMUSG00000021806 | 18074 | 22795 | Nid2 | NP_032721.2, NM_008695.2 | NP_031387.3, NM_007361.3 |
| ENSMUSG00000056481 | 70445 | 57124 | Cd248 | NP_473383.1, NM_054042.2 | NP_065137.1, NM_020404.2 |
| ENSMUSG00000034205 | 94352 | | Loxl2 | NP_201582.2, NM_033325.2 | |
| ENSMUSG00000022816 | 14314 | 11167 | Fstl1 | NP_032073.2, NM_008047.5 | NP_009016.1, NM_007085.4 |
| ENSMUSG00000028369 | 64817 | 79987 | Svep1 | NP_073725.2, NM_022814.2 | NP_699197.3, NM_153366.3 |
| ENSMUSG00000019846 | 16775 | 3910 | Lama4 | NP_034811.2, NM_010681.4 | NP_002281.3, NM_002290.4 |
| ENSMUSG00000056427 | 20564 | 6586 | Slit3 | NP_035542.2, NM_011412.3 | NP_003053.1, NM_003062.3 |

Figure 16 (continued)

| | | | | | |
|---|---|---|---|---|---|
| ENSMUSG00000020695 | 17534 | 9902 | Mrc2 | NP_032652.3, NM_008626.3 | NP_006030.2, NM_006039.4 |
| ENSMUSG00000046841 | 216197 | 10970 | Ckap4 | NP_780660.1, NM_175451.1 | NP_006816.2, NM_006825.3 |
| ENSMUSG00000044017 | 243277 | 283383 | Gpr133 | NP_001074811.1, NM_001081342.1 | NP_942122.2, NM_198827.3 |
| ENSMUSG00000029581 | 14086 | 6624 | Fscn1 | NP_032010.2, NM_007984.2 | NP_003079.1, NM_003088.3 |
| ENSMUSG00000024053 | 246707 | 84034 | Emilin2 | NP_660140.1, NM_145158.3 | NP_114437.2, NM_032048.2 |
| ENSMUSG00000034463 | 219151 | 51435 | Scara3 | NP_766192.1, NM_172604.3 | NP_878185.1, NM_182826.1 |
| ENSMUSG00000062345 | 18788 | 5055 | Serpinb2 | NM_001174170.1, NP_001167641.1 | NP_001137290.1, NM_001143818.1 |
| ENSMUSG00000035385 | 20296 | 6347 | Ccl2 | NP_035463.1, NM_011333.3 | NP_002973.1, NM_002982.3 |
| ENSMUSG00000005534 | 16337 | 3643 | Insr | NP_034698.2, NM_010568.2 | NP_001073285.1, NM_001079817.1 |
| ENSMUSG00000001773 | 53320 | 219595 | Folh1 | NP_001153178.1, NM_001159706.1 | NP_710163.1, NM_153696.2 |
| | 673094 | 4267 | CD99 | NP_079860.2, NM_025584.2 | NP_001264639.1, NM_001277710.1 |
| ENSMUSG00000018166 | 13867 | 2065 | Erbb3 | NP_034283.1, NM_010153.1 | NP_001973.2 and NM_001982.3 |
| ENSMUSG00000062312 | 13866 | 2064 | Erbb2 | NP_001003817.1, NM_001003817.1 | NP_001276865.1, NM_001289936.1, NP_001005862.1, NM_001005862.2, NP_001276867.1, NM_001289938.1 |

Figure 17

| Ensembl ID | Gene ID mouse | Gene ID human | Name | GenBank accession no. | Human ortholog |
|---|---|---|---|---|---|
| ENSMUSG00000001622 | 12994 | 1448 | Csn3 | NP_031812.2, NM_007786.4 | NP_005203.2, NM_005212.2 |
| ENSMUSG00000059588 | 54598 | 10203 | Calcrl | NP_061252.2, NM_018782.2 | NP_001258680.1, NM_001271751.1 |
| ENSMUSG00000000530 | 11482 | 94 | Acvrl1 | NP_001264188.1, NM_001277259.1 | NP_000011.2, NM_000020.2 |
| ENSMUSG00000028859 | 12986 | 1441 | Csf3r | NP_031808.2, NM_007782.3 | NP_758519.1, NM_172313.2 |
| ENSMUSG00000028262 | 80797 | | Clca2 | NP_085104.1, NM_030601.3 | |
| ENSMUSG00000045930 | 66864 | 161198 | Clec14a | NP_080085.3, NM_025809.5 | NP_778230.1, NM_175060.2 |
| ENSMUSG00000069763 | 67888 | 55273 | Tmem100 | NP_080709.1, NM_026433.2 | NP_001093110.1, NM_001099640.1 |
| ENSMUSG00000041134 | 224405 | 116159 | Cyyr1 | NP_659102.1, NM_144853.3 | NP_443186.1, NM_052954.2 |
| ENSMUSG00000029675 | 13717 | 2006 | Eln | NP_031951.2, NM_007925.3 | NP_001075223.1, NM_001081754.2 |
| ENSMUSG00000038007 | 230379 | 340485 | Acer2 | NP_001277472.1, NM_001290543.1 | NP_001010887.2, NM_001010887.2 |
| ENSMUSG00000038679 | 83925 | 7227 | Trps1 | NP_114389.2, NM_032000.2 | NP_054831.2, NM_014112.4 |
| ENSMUSG00000024451 | 106952 | 64411 | Arap3 | NP_001192265.1, NM_001205336.1 | NP_071926.4, NM_022481.5 |

Figure 17 (continued)

| | | | | | |
|---|---|---|---|---|---|
| ENSMUSG00000026768 | 241226 | 8516 | Itga8 | NP_001001309.1, NM_001001309.2 | NP_001278423.1, NM_001291494.1 |
| ENSMUSG00000021904 | 218877 | 56920 | Sema3g | NP_001020550.1, NM_001025379.1 | NP_064548.1, NM_020163.1 |
| ENSMUSG00000024754 | 83921 | 23670 | Tmem2 | NP_001028931.1, NM_001033759.2 | NP_001129292.1, NM_001135820.1 |
| ENSMUSG00000039304 | 22035 | 8743 | Tnfsf10 | NP_033451.1, NM_009425.2 | NP_001177871.1, NM_001190942.1 |
| ENSMUSG00000059325 | 74318 | 84525 | Hopx | NP_783199.1, NM_175606.3 | NP_001138932.1, NM_001145460.1 |
| ENSMUSG00000022991 | 16770 | 3906 | Lalba | NP_034809.1, NM_010679.1 | NP_002280.1, NM_002289.2 |
| ENSMUSG00000048960 | 109294 | 80243 | Prex2 | NP_083801.1, NM_029525.1 | NP_079146.2, NM_024870.2 |
| ENSMUSG00000050808 | 269328 | 143662 | Muc15 | NP_766567.1, NM_172979.3 | NP_001128564.1, NM_001135092.1 |
| ENSMUSG00000037846 | 170799 | 219790 | Rtkn2 | NP_001074815.1, NM_001081346.1 | NP_660350.2, NM_145307.3 |
| ENSMUSG00000076431 | 20677 | 6659 | Sox4 | NP_033264.2, NM_009238.2 | NP_003098.1, NM_003107.2 |
| ENSMUSG00000027217 | 241556 | 90139 | Tspan18 | NP_899003.1, NM_183180.2 | NP_570139.3, NM_130783.4 |
| ENSMUSG00000039116 | 215798 | 57211 | Gpr126 | NP_001002268.1, NM_001002268.3 | NP_065188.4, NM_020455.5 |
| ENSMUSG00000033082 | 243653 | 51267 | Clec1a | NP_780735.2, NM_175526.3 | NP_001284678.1, NM_001297749.1 |
| ENSMUSG00000040289 | 15213 | 23462 | Hey1 | NP_034553.2, NM_010423.2 | NP_036390.3, NM_012258.3 |

SEQUENCE LISTING

<160> NUMBER OF SEQ ID NOS: 9

<210> SEQ ID NO 1
<211> LENGTH: 109
<212> TYPE: PRT
<213> ORGANISM: Escherichia coli

<400> SEQUENCE: 1

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 2
<211> LENGTH: 182
<212> TYPE: PRT
<213> ORGANISM: Escherichia coli

<400> SEQUENCE: 2

Met Lys Ile Lys Thr Leu Ala Ile Val Val Leu Ser Ala Leu Ser Leu
1               5                   10                  15

Ser Ser Thr Ala Ala Leu Ala Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
            115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175

Phe Lys Val Gln Tyr Gln
            180

```
<210> SEQ ID NO 3
<211> LENGTH: 66
<212> TYPE: PRT
<213> ORGANISM: Artificial Sequence
<220> FEATURE:
<223> OTHER INFORMATION: scrambled protein

<400> SEQUENCE: 3

Met Asp Asn Asn Ser Leu Ser Gln Glu Val Gln Asn Gly Ser Asn His
1               5                   10                  15

Leu Glu Asn Asn Gln Ser Gln Ser Asn Gly Gly Ser Asp Ser Ala
            20                  25                  30

Leu Ser Leu Ser Ser Lys Thr Ala Ala Leu Ala Ala Ala Thr Thr Val
            35                  40                  45

Asn Asp Gly Ser Asp Gly Ala Thr Ser Ser Ala Val Gly Met Asx Leu
        50                  55                  60

Glu Asp
65

<210> SEQ ID NO 4
<211> LENGTH: 58
<212> TYPE: PRT
<213> ORGANISM: Artificial Sequence
<220> FEATURE:
<223> OTHER INFORMATION: truncated thioredocin-1

<400> SEQUENCE: 4

Gly Lys Leu Thr Val Ala Lys Leu Asn Ile Asp Gln Asn Pro Gly Thr
1               5                   10                  15

Ala Pro Lys Tyr Gly Ile Arg Gly Ile Pro Thr Leu Leu Leu Phe Lys
            20                  25                  30

Asn Gly Glu Val Ala Ala Thr Lys Val Gly Ala Leu Ser Lys Gly Gln
            35                  40                  45

Leu Lys Glu Phe Leu Asp Ala Asn Leu Ala
        50                  55

<210> SEQ ID NO 5
<211> LENGTH: 73
<212> TYPE: PRT
<213> ORGANISM: Artificial Sequence
<220> FEATURE:
<223> OTHER INFORMATION: truncated thioredocin-1

<400> SEQUENCE: 5

Met Gly Lys Leu Thr Val Ala Lys Leu Asn Ile Asp Gln Asn Pro Gly
1               5                   10                  15

Thr Ala Pro Lys Tyr Gly Ile Arg Gly Ile Pro Thr Leu Leu Leu Phe
            20                  25                  30

Lys Asn Gly Glu Val Ala Ala Thr Lys Val Gly Ala Leu Ser Lys Gly
            35                  40                  45

Gln Leu Lys Glu Phe Leu Asp Ala Asn Leu Ala Gly Ser Gly Ser Gly
        50                  55                  60

Ser Gly Ser His His His His His His
65                  70

<210> SEQ ID NO 6
<211> LENGTH: 131
<212> TYPE: PRT
<213> ORGANISM: Artificial Sequence
<220> FEATURE:
<223> OTHER INFORMATION: truncated fimbrial protein
```

<400> SEQUENCE: 6

Ala Ala Thr Thr Val Asn Gly Gly Thr Val His Phe Lys Gly Glu Val
1               5                   10                  15

Val Asn Ala Ala Cys Ala Val Asp Ala Gly Ser Val Asp Gln Thr Val
            20                  25                  30

Gln Leu Gly Gln Val Arg Thr Ala Ser Leu Ala Gln Glu Gly Ala Thr
        35                  40                  45

Ser Ser Ala Val Gly Phe Asn Ile Gln Leu Asn Asp Cys Asp Thr Asn
    50                  55                  60

Val Ala Ser Lys Ala Ala Val Ala Phe Leu Gly Thr Ala Ile Asp Ala
65                  70                  75                  80

Gly His Thr Asn Val Leu Ala Leu Gln Ser Ala Ala Gly Ser Ala
                85                  90                  95

Thr Asn Val Gly Val Gln Ile Leu Asp Arg Thr Gly Ala Ala Leu Thr
                100                 105                 110

Leu Asp Gly Ala Thr Phe Ser Ser Glu Thr Thr Leu Asn Asn Gly Thr
            115                 120                 125

Asn Thr Ile
    130

<210> SEQ ID NO 7
<211> LENGTH: 131
<212> TYPE: PRT
<213> ORGANISM: Artificial Sequence
<220> FEATURE:
<223> OTHER INFORMATION: truncated fimbrial protein

<400> SEQUENCE: 7

Lys Ala Thr Thr Val Asn Gly Gly Thr Val His Phe Lys Gly Glu Val
1               5                   10                  15

Val Asn Ala Ala Cys Ala Val Asp Ala Gly Ser Val Asp Gln Thr Val
            20                  25                  30

Gln Leu Gly Gln Val Arg Thr Ala Ser Leu Ala Gln Glu Gly Ala Thr
        35                  40                  45

Ser Ser Lys Val Gly Phe Asn Ile Gln Leu Asn Asp Cys Asp Thr Asn
    50                  55                  60

Val Ala Ser Lys Ala Ala Val Ala Phe Leu Gly Thr Lys Ile Asp Ala
65                  70                  75                  80

Gly His Thr Asn Val Leu Ala Leu Gln Ser Ala Ala Gly Ser Asp
                85                  90                  95

Thr Asn Val Gly Val Gln Ile Leu Asp Arg Thr Gly Ala Ala Leu Thr
                100                 105                 110

Leu Asp Gly Ala Thr Phe Ser Ser Glu Thr Thr Leu Asn Asn Asp Thr
            115                 120                 125

Asn Thr Ile
    130

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
tatcatatgg gcaaactgac cgttgcaaaa ctga                            34

```
<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
agcggatccg ctaccagaac cagaaccggc cag                               33
```

FUSION POLYPEPTIDE COMPRISING A FOREIGN ANTIGEN AND SELF ANTIGEN

RELATED APPLICATIONS

This application is a United States National Phase under 35 U.S.C. § 371 of International Application No. PCT/NL2017/050526, filed on 4 Aug. 2017, which claims priority to European Patent Application No. 16182827.2, filed 4 Aug. 2016, both of which are hereby incorporated by reference in their entirety for all purposes.

FIELD OF THE INVENTION

The invention is in the field of medicine. More specifically, it is in the field of medical treatment and diagnostics relating to immunotherapy based on anti-self antibodies, as produced by a subjects immune system to foreign-self protein fusions. The invention relates to foreign-self protein fusions, to compositions comprising such fusions as immunogens, and vaccines based thereon. The invention further relates to methods of producing antiself antibodies. The invention also relates to methods of detecting protein expression using antiself antibodies, in particular for diagnostic purpose, such as for determining tumor angiogenesis status in the diagnosis of cancer. In particular, the invention relates to foreign-self protein fusions as therapeutic antigens, to antiself antibodies for use in therapy and diagnostics, and to compositions comprising such fusions or antibodies.

BACKGROUND OF THE INVENTION

Human antiself antibodies are of particular value for in vivo therapeutic and diagnostic purposes, since they avoid the problems arising from the antigenicity of foreign, e.g. mouse antibodies. The most useful human antibodies for therapy are those directed against cell surface molecules, such as receptors, adhesins and integrins, and those directed against circulating biological effector molecules, such as hormones, growth factors and cytokines. It has been extremely difficult to obtain human antibodies against such self antigens (anti-self antibodies) and to generate human mAbs directed against human antigens, for example to treat or prevent atherosclerosis or asthma, to treat cancer, or to block septic shock. This difficulty results from immunological tolerance mechanisms that prevent the antigen-driven expansion of B-cell clones with self specificities. This invention provides a powerful way of obtaining such antibodies.

In methods of treating cancer by immunotherapy, it is essential to target tumor-specific self-antigens. As angiogenesis is a process occurring in tumors, and since the vascular endothelial growth factor (VEGF) is one of the main growth factors promoting tumor angiogenesis, there are several drugs on the market that specifically target the VEGF signaling pathway in order to inhibit and stop tumor growth. These include VEGF neutralizing antibodies such as bevacizumab (Avastin®) or tyrosine kinase inhibitors of the growth factor receptors (e.g. sunitinib, Sutent®).

These drugs, however, only show a modest effect on patient survival. For example, bevacizumab prolongs survival in colorectal cancer patients on average by only 3-4 months. Part of this limited therapeutic effect is due to induction of drug resistance that develops upon inhibition of tumor-derived growth. Besides their limited activity, current angiogenesis inhibitors show severe side-effects in patients.

Therefore, anti-angiogenic cancer drugs with higher specificity are needed. It is noted herein that especially the development of therapeutic anti-angiogenic cancer vaccine compositions, comprising tumor vascular antigens "self" to the human body that are involved in angiogenesis, is an arduous task. The immune response to self-antigens is tightly regulated to avoid recognition of self-molecules and thereby destruction of "self" tissues. At the onset of cancer, T-cells are occasionally able to recognize self-antigens on cancer cells and to evoke an immune response against the cancer. However, when the cancer progresses, immune surveillance of the disease is impaired due to the fact that the cancer employs several mechanisms to impair the immune response. These mechanisms include, amongst others, downregulation of MHC-I, secretion of TGF beta, which suppresses the immune system and the induction of T regulatory cells. For these reasons, vaccination against cancer is a challenge.

The art describes inter alia anti-angiogenic cancer vaccine compositions that comprise a fusion protein consisting of a foreign part (e.g. bacterial thioredoxin, TRX), linked to a "self" antigen (e.g. extra domain-B (EDB) of fibronectin). A problem related to the use of such fusion proteins is that, although the foreign immunogen is a requirement for inducing the immune response against self, an overt antigenicity of the foreign part of the fusion protein can suppress the humoral immune response against the self antigen. There are currently no fusion polypeptides in vaccine compositions that allow for the induction of a suitable amount of immunogenicity against the self part. This is due to the strong antibody titer response against the foreign immunogen. In other words, in the art, there are no fusion polypeptides described that provide for a reduced humoral immune response against a foreign, non-self antigen, thereby maximizing the response to the self antigen.

Further, it is clear that there is a need in the art for diagnostic tools that are based on highly specific tumor angiogenesis markers and a need for therapeutic modalities, based on such highly specific tumor angiogenesis markers, such as vaccine compositions capable of eliciting an immune response against tumor angiogenesis antigens "self" to the human body and therefore breaking self-tolerance to the self-antigen. It is a goal of the present invention to provide such highly specific tumor angiogenesis markers and to provide therapeutic modalities based on these markers. More specifically, it is a goal of the invention to provide anti-angiogenic cancer vaccine compositions that exhibit improved elicitation of an immune response by modification of the foreign part of the fusion protein. It is thus a goal of the invention to provide anti-angiogenic cancer vaccine compositions that induce a clinically relevant immune response.

SUMMARY OF THE INVENTION

It was found that by carefully designing the non-self or foreign polypeptide part to contain either a truncation as compared to an immunogenic parent polypeptide and/or a specific percentage of hydrophilic, bulky amino acid residues, it was possible to provide a fusion polypeptide that is capable of inducing an immune response against the self polypeptide by redirecting the immune response to reduce the antibody response to the foreign antigen. In such a way, an immunogenic composition is provided that is improved in that it exhibits a reduced humoral immune response against a foreign, non-self antigen, while having an increased humoral immune response against an antigen of interest, such as a self-antigen, as compared to inter alia a non-truncated parent molecule from which the non-self antigen is derived. It was further found that such a tumor vaccine, when administered to a subject, elicits a relevant immune response against an antigen such as a self-antigen.

The inventors solved the aforementioned problem by providing a fusion polypeptide comprising a foreign antigen and a self antigen, wherein said foreign antigen consists of a polypeptide comprising an amino acid sequence of at least 12-15 amino acid residues, 12-24% of which residues are hydrophilic, bulky amino acid residues selected from the group consisting of histidine, glutamate, arginine, glutamine, aspartic acid and/or lysine.

In a preferred embodiment of a fusion polypeptide according to the invention, said foreign antigen comprises an immunogenic region of the truncated protein of SEQ ID NO:1 or of a truncated protein having at least 90% sequence identity (over the length of the protein) to the protein of SEQ ID NO:1; or an immunogenic region of the truncated protein of SEQ ID NO:2 or of a truncated protein having at least 90% sequence identity (over the length of the protein) to the protein of SEQ ID NO:2; or an immunogenic region of the optionally truncated protein of SEQ ID NO:3 or of a protein having at least 90% sequence identity to the optionally truncated protein of SEQ ID NO:3.

In another preferred embodiment of a fusion polypeptide according to the invention, said truncation in said truncated protein comprises a removal of from between 1 and 100 amino acids, preferably between 10 and 50 amino acids, from the C-terminal side, the N-terminal side, or both the C- and N-terminal side of said protein.

In yet another preferred embodiment of a fusion polypeptide according to the invention, said foreign antigen comprises an immunogenic region of 45-70 consecutive amino acid residues of the protein of SEQ ID NO:1 or of a protein having at least 90% sequence identity to the protein of SEQ ID NO:1; or an immunogenic region of 110-150 consecutive amino acid residues of the protein of SEQ ID NO:2 or of a protein having at least 90% sequence identity to the protein of SEQ ID NO:2; or an immunogenic region of 45-61 consecutive amino acid residues of the protein of SEQ ID NO:3 or of a protein having at least 90% sequence identity to the protein of SEQ ID NO:3.

In yet another preferred embodiment of a fusion polypeptide according to the invention, said fusion polypeptide elicits a serum level of immunoglobulins against said self antigen of at least 0.5%, preferably at least 1%, of the total serum immunoglobulin level in a mammalian subject to which said fusion polypeptide is administered.

In yet another preferred embodiment of a fusion polypeptide according to the invention, said foreign antigen comprises the amino acid sequence of SEQ ID NOs: 3, 4, 6 or 7.

In yet another preferred embodiment of a fusion polypeptide according to the invention, said self antigen is a mammalian, preferably human, polypeptide, the expression of which is associated with tumor angiogenesis, preferably said polypeptide is selected from the group consisting of tissue inhibitor of metalloproteinase 1 (Timp1), apelin (Apln), serum amyloid A3 (Saa3), CD93 antigen (Cd93), heart development protein with EGF-like domains 1 (Heg1), Notch 4, apelin receptor (Aplnr), nestin (Nes), tenascin C (Tnc), pentraxin related gene (Ptx3), vimentin (Vim), human EGF receptor-2 (erbb2, HER2), erbb3 (HER3), tumor necrosis factor alpha induced protein 6 (Tnfaip6), carboxypeptidase Z (Cpz), snail family zinc finger 1 (Snai1), premelanosome protein (Pmel), arylsulfatase I (Arsi), WNT1 inducible signaling pathway protein 1 (Wisp1), glutathione peroxidase 7 (Gpx7), a disintegrin-like and metallopeptidase (reprolysin type) with thrombospondin type 1 motif, 4 (Adamts4), endothelial cell-specific molecule 1 (Esm1), integrin alpha 5 (fibronectin receptor alpha) (Itga5), a disintegrin-like and metallopeptidase (reprolysin type) with thrombospondin type 1 motif, 2 (Adamts2), thrombospondin 2 (Thbs2), matrix metallopeptidase 14 (membrane-inserted) (Mmp14), insulin-like growth factor binding protein 3 (1043), thrombospondin 1 (Thbs1), fibrillin 1 (Fbn1), periostin, osteoblast specific factor (Postn), leucine rich repeat containing 17 (Lrrc17), fibrillin 2 (Fbn2), cerebral endothelial cell adhesion molecule (Cercam), secreted frizzled-related protein 4 (Sfrp4), C1q and tumor necrosis factor related protein 6 (C1qtnf6), lysyl oxidase-like 3 (Loxl3), immunoglobulin superfamily, member 10 (Igsf10), secreted frizzled-related protein 2 (Sfrp2), FK506 binding protein 10 (Fkbp10), glutamine fructose-6-phosphate transaminase 2 (Gfpt2), carboxypeptidase X 1 (Cpxm1), microfibrillar associated protein 5 (Mfap5), epidermal growth factor-containing fibulin-like extracellular matrix protein 2 (Efemp2), nephroblastoma overexpressed gene (Nov), versican (Vcan), elastin (Eln), cysteine rich protein 61 (Cyr61), sulfatase 1 (Sulf1), nidogen 2 (Nid2), CD248 antigen, endosialin (Cd248), lysyl oxidase-like 2 (Loxl2), follistatin-like 1 (Fstl1), sushi, von Willebrand factor type A, EGF and pentraxin domain containing 1 (Svep1), laminin, alpha 4 (Lama4), slit homolog 3 (Slit3), mannose receptor, C type 2 (Mrc2), cytoskeleton-associated protein 4 (Ckap4), G protein-coupled receptor 133 (Gpr133), fascin homolog 1, actin bundling protein (Fscn1), elastin microfibril interfacer 2 (Emilin2), scavenger receptor class A, member 3 (Scara3), serine (or cysteine) peptidase inhibitor, clade B, member 2 (Serpinb2), chemokine (C—C motif) ligand 2 (Ccl2), insulin receptor (Insr), folate hydrolase 1 (Folh1), CD99 antigen (CD99), casein kappa (Csn3), calcitonin receptor-like (Calcrl), activin A receptor, type II-like 1 (Acvrl1), colony stimulating factor 3 receptor (Csf3r), chloride channel calcium activated 2 (Clca2), C-type lectin domain family 14, member a (Clec14a), transmembrane protein 100 (Tmem100), cysteine and tyrosine-rich protein 1 (Cyyr1), alkaline ceramidase 2 (Acer2), trichorhinophalangeal syndrome I (Trps1), ArfGAP with RhoGAP domain, ankyrin repeat and PH domain 3 (Arap3), integrin alpha 8 (Itga8), sema domain, immunoglobulin domain (Ig), short basic domain, secreted, (semaphorin) 3G (Sema3g), transmembrane protein 2 (Tmem2), tumor necrosis factor (ligand) superfamily, member 10 (Tnfsf10), HOP homeobox (Hopx), lactalbumin, alpha (Lalba), phosphatidylinositol-3,4,5-trisphosphate-dependent Rac exchange factor 2 (Prex2), mucin 15 (Muc15), rhotekin 2 (Rtkn2), SRY (sex determining region Y)-box 4 (Sox4), tetraspanin 18 (Tspan18), G protein-coupled receptor 126 (Gpr126), C-type lectin domain family 1, member a (Clec1a), extra domain-B of fibronectin (ED-B), hairy/enhancer-of-split related with YRPW motif 1 (Hey1) and sulfatase 2 (Sulf2).

In yet another preferred embodiment of a fusion polypeptide according to the invention, said immunogenic region of the protein of SEQ ID NO:1 is in the region of Ala-30 to Ala-109, preferably the region of Gln-52 to Ala-109, of the protein of SEQ ID NO:1; and/or wherein said 110-150 immunogenic amino acid residue region of the protein of SEQ ID NO:2 is the region of Ala-24 to Ile-154 of the protein of SEQ ID NO:2.

In yet another preferred embodiment of a fusion polypeptide according to the invention, said foreign antigen consists of the amino acid sequence of SEQ ID NOs: 3, 4, 6 or 7.

In yet another preferred embodiment of a fusion polypeptide according to the invention, said fusion protein comprises a linker peptide linking said foreign and self antigen, preferably a GS linker peptide.

In another aspect, the present invention provides the fusion polypeptide according to the invention as described above for use as a medicament, preferably for use as a vaccine antigen for eliciting an immune response against said self antigen, more preferably for use in treating or preventing arthritis, atherosclerosis, restenosis, transplant arteriopathy, warts, scar keloids, synovitis, osteomyelitis, asthma, nasal polyps, polypoidal choroidal vasculopathy, age-related macular degeneration, retinopathy of prematurity, diabetic retinopathy, AIDS, IBD, Crohn's disease, endometriosis, uterine bleeding, psoriasis, myoma's, cancer, or combinations thereof.

In another aspect, the present invention provides the fusion polypeptide according to the invention for use in inhibiting, counteracting or blocking tumor angiogenesis and/or removing tumor vasculature in a subject.

In another aspect, the present invention provides a nucleic acid encoding a fusion polypeptide according to the invention, optionally comprised in an expression vector.

In another aspect, the present invention provides a host cell comprising the nucleic acid according to the invention.

In another aspect, the present invention provides an immunogenic composition comprising the fusion polypeptide according to the invention or the nucleic acid according to the invention, said composition further comprising a pharmaceutically acceptable carrier, preferably an aqueous liquid, and optionally an adjuvant.

In a preferred embodiment of the composition of the invention, the composition is a vaccine composition, preferably for use in treating or preventing arthritis, atherosclerosis, restenosis, transplant arteriopathy, warts, scar keloids, synovitis, osteomyelitis, asthma, nasal polyps, polypoidal choroidal vasculopathy, age-related macular degeneration, retinopathy of prematurity, diabetic retinopathy, AIDS, IBD, Crohn's disease, endometriosis, uterine bleeding, psoriasis, myoma's, cancer, or combinations thereof.

In yet another preferred embodiment of the composition of the invention, said composition comprises an adjuvant in a weight percent ratio range of fusion polypeptide:adjuvant of 3:1 to 1:3, preferably about 1:1.

In another aspect, the present invention provides an isolated antiself antibody that specifically binds to the self antigen of the fusion polypeptide according to the invention.

In a preferred embodiment of the isolated antiself antibody of the invention, said antibody is a monoclonal antibody, preferably of the IgG isotype, preferably said monoclonal antibody is isolated from a B-cell from a mammal having received the fusion protein and for which said self antigen is self.

In yet another preferred embodiment of the isolated antiself antibody of the invention, said antibody is labeled with a detectable label.

In another aspect, the present invention provides an immortalized B-cell line producing a monoclonal antibody that specifically binds to the self antigen of the fusion polypeptide according to the invention.

In another aspect, the present invention provides a method for eliciting an immune response against a self antigen comprising administering to a subject in need of treatment a therapeutically effective dose of the fusion polypeptide according to the invention or the composition according to the invention.

In another aspect, the present invention provides a method for treating or preventing arthritis, atherosclerosis, restenosis, transplant arteriopathy, warts, scar keloids, synovitis, osteomyelitis, asthma, nasal polyps, polypoidal choroidal vasculopathy, age-related macular degeneration, retinopathy of prematurity, diabetic retinopathy, AIDS, IBD, Crohn's disease, endometriosis, uterine bleeding, psoriasis, myoma's, cancer, or combinations thereof, comprising administering to a subject in need of treatment a therapeutically effective dose of the fusion polypeptide according to the invention or the composition according to the invention.

In yet another preferred embodiment of a method of typing a subject, comprising contacting said subject or a body sample of said subject with the isolated antiself antibody according to the invention, allowing said antibody to specifically bind to its antigen, and evaluating the level of specific binding between said antibody and said antigen, preferably by measuring the amount of specifically bound antibody wherein said antibody is an antibody labeled with a detectable label, preferably wherein said method of typing is a method of stratifying patients.

In another aspect, the present invention provides a method of typing a subject for a tumor angiogenesis status, comprising the steps of a) measuring a gene expression level of at least one gene expression product in a sample of a subject comprising, or suspected to comprise, tumor cells, preferably tumor endothelial cells, wherein said at least one gene expression product is selected from the group formed by tissue inhibitor of metalloproteinase 1 (Timp1), apelin (Apln), serum amyloid A3 (Saa3), CD93 antigen (Cd93), heart development protein with EGF-like domains 1 (Heg1), Notch 4, apelin receptor (Aplnr), nestin (Nes), tenascin C (Tnc), pentraxin related gene (Ptx3), vimentin (Vim), tumor necrosis factor alpha induced protein 6 (Tnfaip6), carboxypeptidase Z (Cpz), snail family zinc finger 1 (Snai1), premelanosome protein (Pmel), arylsulfatase I (Arsi), WNT1 inducible signaling pathway protein 1 (Wisp1), glutathione peroxidase 7 (Gpx7), a disintegrin-like and metallopeptidase (reprolysin type) with thrombospondin type 1 motif, 4 (Adamts4), endothelial cell-specific molecule 1 (Esm1), integrin alpha 5 (fibronectin receptor alpha) (Itga5), a disintegrin-like and metallopeptidase (reprolysin type) with thrombospondin type 1 motif, 2 (Adamts2), thrombospondin 2 (Thbs2), matrix metallopeptidase 14 (membrane-inserted) (Mmp14), insulin-like growth factor binding protein 3 (Igfbp3), thrombospondin 1 (Thbs1), fibrillin 1 (Fbn1), periostin, osteoblast specific factor (Postn), leucine rich repeat containing 17 (Lrrc17), fibrillin 2 (Fbn2), cerebral endothelial cell adhesion molecule (Cercam), secreted frizzled-related protein 4 (Sfrp4), C1q and tumor necrosis factor related protein 6 (C1qtnf6), lysyl oxidase-like 3 (Loxl3), immunoglobulin superfamily, member 10 (Igsf10), secreted frizzled-related protein 2 (Sfrp2), FK506 binding protein 10 (Fkbp10), glutamine fructose-6-phosphate transaminase 2 (Gfpt2), carboxypeptidase X 1 (Cpxm1), microfibrillar associated protein 5 (Mfap5), epidermal growth factor-containing fibulin-like extracellular matrix protein 2 (Efemp2), nephroblastoma overexpressed gene (Nov), versican (Vcan), elastin (Eln), cysteine rich protein 61 (Cyr61), sulfatase 1 (Sulf1), nidogen 2 (Nid2), CD248 antigen, endosialin (Cd248), lysyl oxidase-like 2 (Loxl2), follistatin-like 1 (Fstl1), sushi, von Willebrand factor type A, EGF and pentraxin domain containing 1 (Svep1), laminin, alpha 4 (Lama4), slit homolog 3 (Slit3), mannose receptor, C type 2 (Mrc2), cytoskeleton-associated protein 4 (Ckap4), G protein-coupled receptor 133 (Gpr133), fascin homolog 1, actin bundling protein (Fscn1), elastin microfibril interfacer 2 (Emilin2), scavenger receptor class A, member 3 (Scara3), serine (or cysteine) peptidase inhibitor, clade B, member 2 (Serpinb2), chemokine (C—C motif) ligand 2 (Ccl2), insulin receptor (Insr), folate hydrolase 1 (Folh1), CD99 antigen (CD99), casein kappa (Csn3), calcitonin receptor-like (Calcrl), activin A receptor, type II-like 1 (Acvrl1), colony stimulating factor 3 receptor (Csf3r), chloride channel calcium activated 2 (Clca2), C-type lectin domain family 14, member a (Clec14a), transmembrane protein 100 (Tmem100), cysteine and tyrosine-rich protein 1 (Cyyr1), alkaline ceramidase 2 (Acer2), trichorhinophalangeal syndrome I (Trps1), ArfGAP with RhoGAP domain, ankyrin repeat and PH domain 3 (Arap3), integrin alpha 8 (Itga8), sema domain, immunoglobulin domain (Ig), short basic domain, secreted, (semaphorin) 3G (Sema3g), transmembrane protein 2 (Tmem2), tumor necrosis factor (ligand) superfamily, member 10 (Tnfsf10), HOP homeobox (Hopx), lactalbumin, alpha (Lalba), phosphatidylinositol-3,4,5-trisphosphate-dependent Rac exchange factor 2 (Prex2), mucin 15 (Muc15), rhotekin 2 (Rtkn2), SRY (sex determining region Y)-box 4 (Sox4), tetraspanin 18 (Tspan18), G protein-coupled receptor 126 (Gpr126), C-type lectin domain family 1, member a (Clec1a), extra domain-B of fibronectin (ED-B), hairy/enhancer-of-split related with YRPW motif 1 (Hey1) and sulfatase 2 (Sulf2); b) comparing said gene expression level to a gene expression control value; c) typing said subject for a tumor angiogenesis status on the basis of the difference between said gene expression level and said gene expression control value.

In a preferred embodiment of the method of typing a subject for a tumor angiogenesis status, said typing is the typing of said sample of said subject.

In yet another preferred embodiment of the method of typing a subject for a tumor angiogenesis status, said gene expression control value is obtained by measuring the gene expression level of said at least one gene expression product in a control sample comprising non-tumor endothelial cells of a subject.

In yet another preferred embodiment of the method of typing a subject for a tumor angiogenesis status, said subject is typed positive for tumor angiogenesis status if the gene expression level of said at least one gene expression product is at least 5 times, preferably at least 20 times, higher than said gene expression control value, or wherein said subject is typed negative for tumor angiogenesis status if the gene expression level of said at least one gene expression product is not at least 5 times higher, preferably not at least 20 times higher, than said gene expression control value.

In another aspect, the present invention provides a diagnostic method comprising using the antibody according to the invention, wherein said diagnostic method comprises evaluating cytostatic efficacy of a cytostatic or prediction of drug activity.

In general, the various therapeutic methods of the invention may also be used for anti-angiogenic therapies, including, but not limited to disorders relating to angiogenesis.

DESCRIPTION OF THE DRAWINGS

FIG. 1D shows a Venn-diagram, indicating genes upregulated in E11, E18 and TEC compared to adult mouse (as explained in Example 1).

FIG. 3 again underlines the fact that the fusion proteins of the invention elicit increased anti-EDB antibody titers as compared to the TRX-EDB fusion protein.

FIG. 9 lists a preferred embodiment for the self antigen, wherein said self antigen has an antitumor effect.

FIG. 10 lists a preferred embodiment for the self antigen, wherein said self antigen is high in Mets.

FIG. 11 lists a number of preferred embodiments for the self antigens, wherein said self antigens are membrane antigens.

FIG. 12 lists a number of preferred embodiments for the self antigens, wherein said self antigens are secreted antigens.

FIG. 13 lists a number of preferred embodiments for the self antigens, wherein said self antigens are cytoplasmatic targets.

FIG. 14 lists a number of preferred embodiments for the self antigens, wherein said self antigens are extracellular targets.

FIG. 15 lists a number of preferred embodiments for the self antigens, wherein said self antigens are involved in various disease related processes.

FIG. 16 lists a number of preferred embodiments for the self antigens, wherein said self antigens are involved in tumor development.

FIG. 17 lists a number of preferred embodiments for the self antigens, wherein said self antigens are involved in metastasis.

The identifiers given in the tables herein pertain to NCBI-GenBank Flat File Release 213.0 incorporating data processed by the INSDC databases as of Thursday, Apr. 14, 2016. Genbank references indicated herein include reference to those sequences in their entirety.

Figure 18:
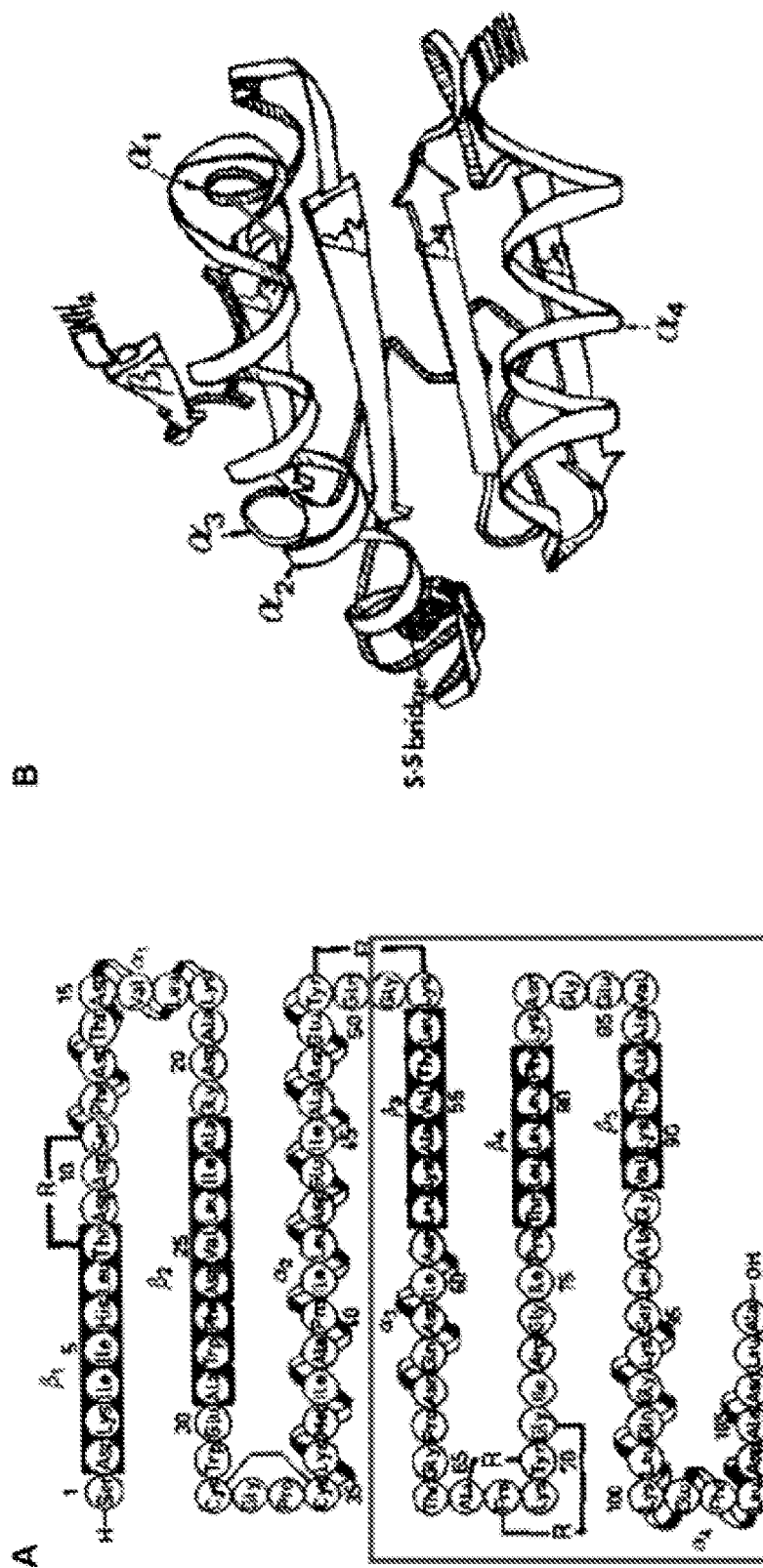

FIG. 18 shows in panel A) the amino acid sequence of thioredoxin-$S_2$ from *E. coli* and its secondary structure elements. Amino acid residues 51-108 were used to generate a truncated immunogenic region of 45-70 consecutive amino acid residues of the protein of SEQ ID NO:1 or of a protein having at least 90% sequence identity to the protein of SEQ ID NO:1 (TRX-trunc) (box). In this illustration, the starting amino acid methionine (M) is lacking. Panel B) shows a schematic drawing of the three-dimensional structure of *E. coli* thioredoxin-$S_2$. The line (close to the arrowed $\alpha_1$ subunit) indicates the cleavage site to generate TRX-trunc as indicated in SEQ ID NO: 4.

Figure 19:
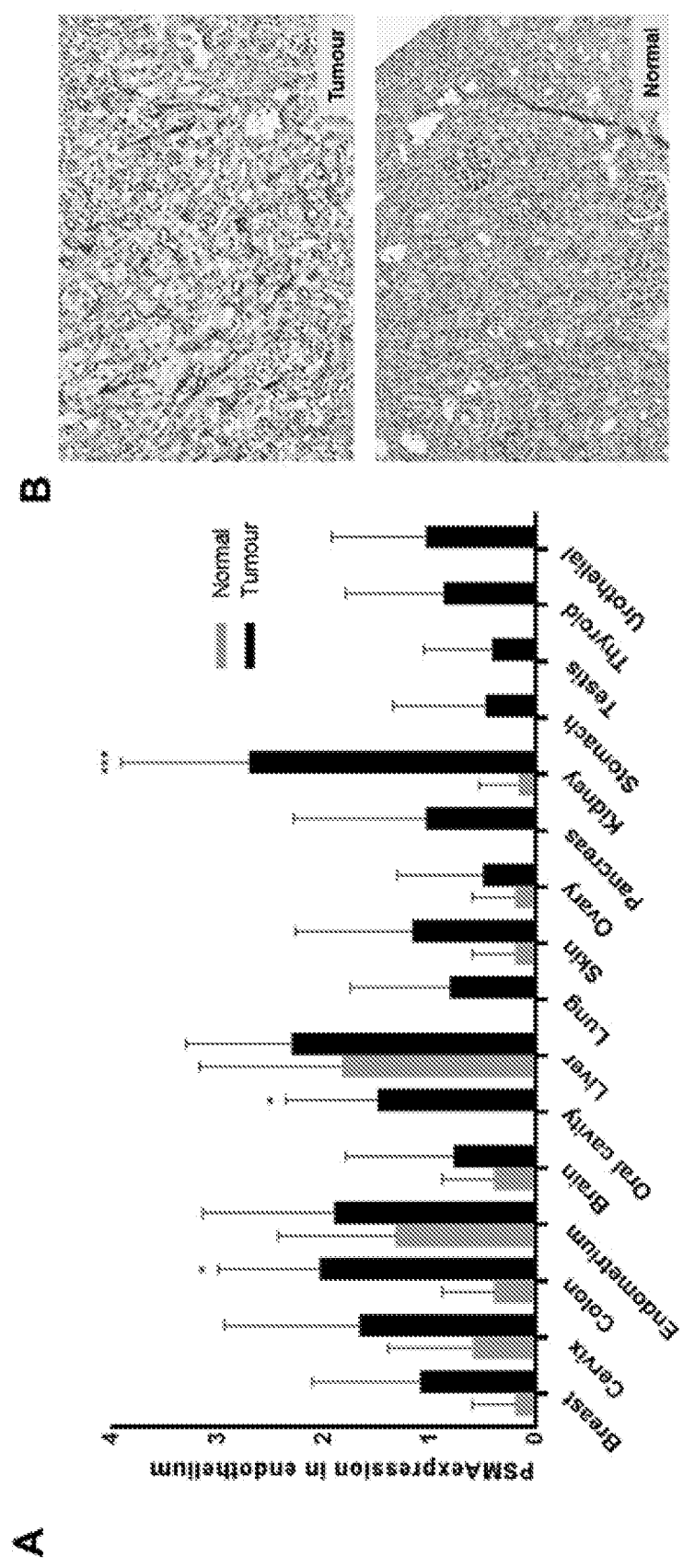

FIG. 19 shows expression of self antigen target PSMA in tumour endothelium compared to normal endothelium. A) Comparison of PSMA expression on endothelium of different tumour types compared to normal endothelium. Data obtained from the Human Protein Atlas and scored as follows: 0, no staining detected; 1, weak; 2, moderate; 3 high; 4, extremely high. Breast: tumour n=21, normal n=5; Cervix: tumour n=24, normal n=5; Colon: tumour n=23, normal n=5; Endometrium: tumour n=22, normal n=6; Brain: tumour n=21, normal n=5; Oral cavity: tumour n=8, normal n=5; Liver: tumour n=23, normal n=6; Lung: tumour n=22, normal n=6; Skin: tumour n=24, normal n=5; Ovary: tumour n=24, normal n=6; Pancreas: tumour n=24, normal n=6; Kidney: tumour n=24, normal n=6; Stomach: tumour n=23, normal n=6; Testis: tumour n=24, normal n=5; Thyroid: tumour n=8, normal n=6; Urothelial: tumour n=24, normal n=5. Values with P<0.05 were considered to be significant. B) Renal cell carcinoma and normal kidney sections stained with anti-PSMA antibody obtained from the Human Protein Atlas.

Figure 20:
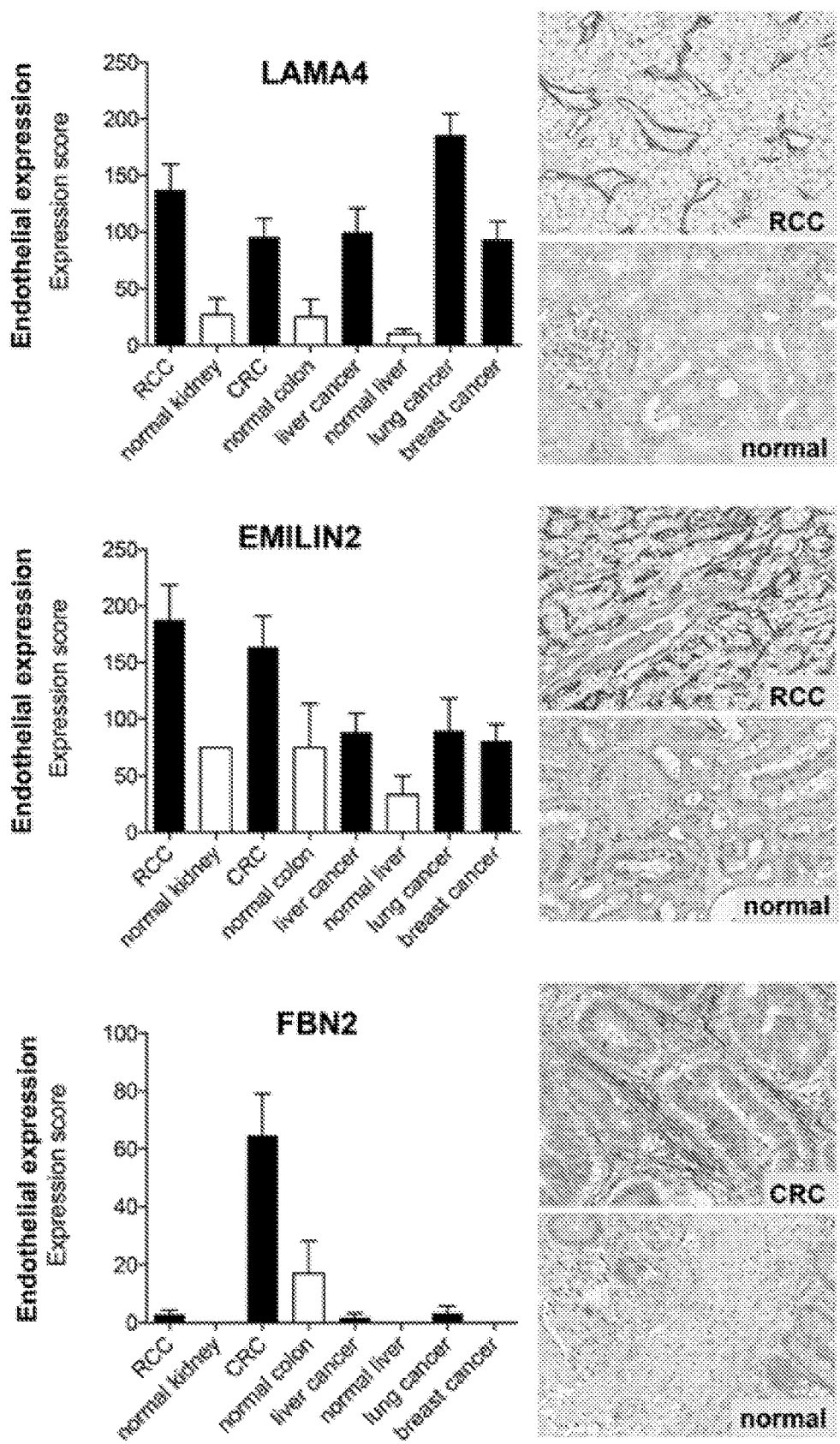

FIG. 20 shows expression of the self antigen targets LAMA4, EMILIN2 and FBN2 in tumour endothelium compared to normal endothelium. Left panels: Comparison of target gene expression on endothelium of different tumour types compared to normal endothelium. Data obtained from the Human Protein Atlas and scored as follows: 0, no staining detected; 1, weak; 2, moderate; 3 high. LAMA4: kidney: tumor n=12; normal n=5; colon: tumor n=12; normal n=5; lung: tumor n=12; normal n=5; liver: tumor n=12; normal n=6; breast: tumor n=12; EMILIN2: kidney: tumor n=10; normal n=3; colon: tumor n=11; normal n=3; lung: tumor n=10; liver: tumor n=11; normal n=3; breast: tumor n=11; FBN2: kidney: tumor n=11; normal n=6; colon: tumor n=11; normal n=5; lung: tumor n=12; liver: tumor n=12; normal n=6; breast: tumor n=12. Right panels: Renal cell carcinoma (RCC) and normal kidney sections stained with anti-LAMA4 or EMILIN2 antibody obtained from the Human Protein Atlas. Colorectal cancer (CRC) sections or normal colon stained with anti-FBN2 antibody obtained from the Human Protein Atlas.

Figure 21:
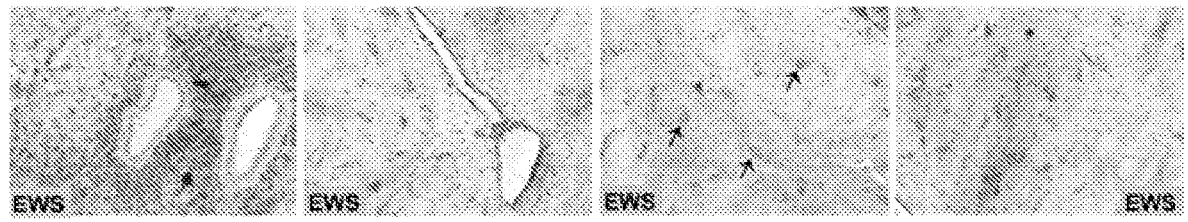

FIG. 21 shows the expression of the self antigen target CD99 in tumour endothelium of Ewing sarcoma (EWS). Human Ewing sarcoma tissues were stained with an anti-CD99 antibody (ab27271, Abcam, Cambridge, UK). Arrows in the third picture from the left indicate vascular expression of CD99. Magnification 200×.

Figure 22:
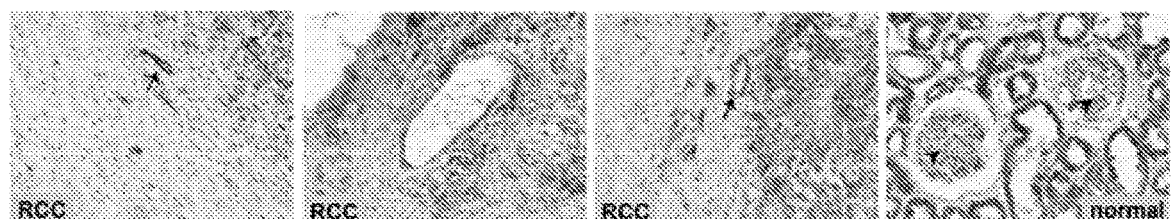

FIG. 22 shows the expression of the self antigen target VCAN in the tumor endothelium of renal cell carcinoma. Human renal cell carcinoma tissues and normal kidney were stained with an anti-Versican antibody. Arrows indicate vascular expression of VCAN. Arrow heads in the far right panel show that no vascular staining is present in the glomeruli of normal kidney tissue. Magnification 200×.

Figure 23:
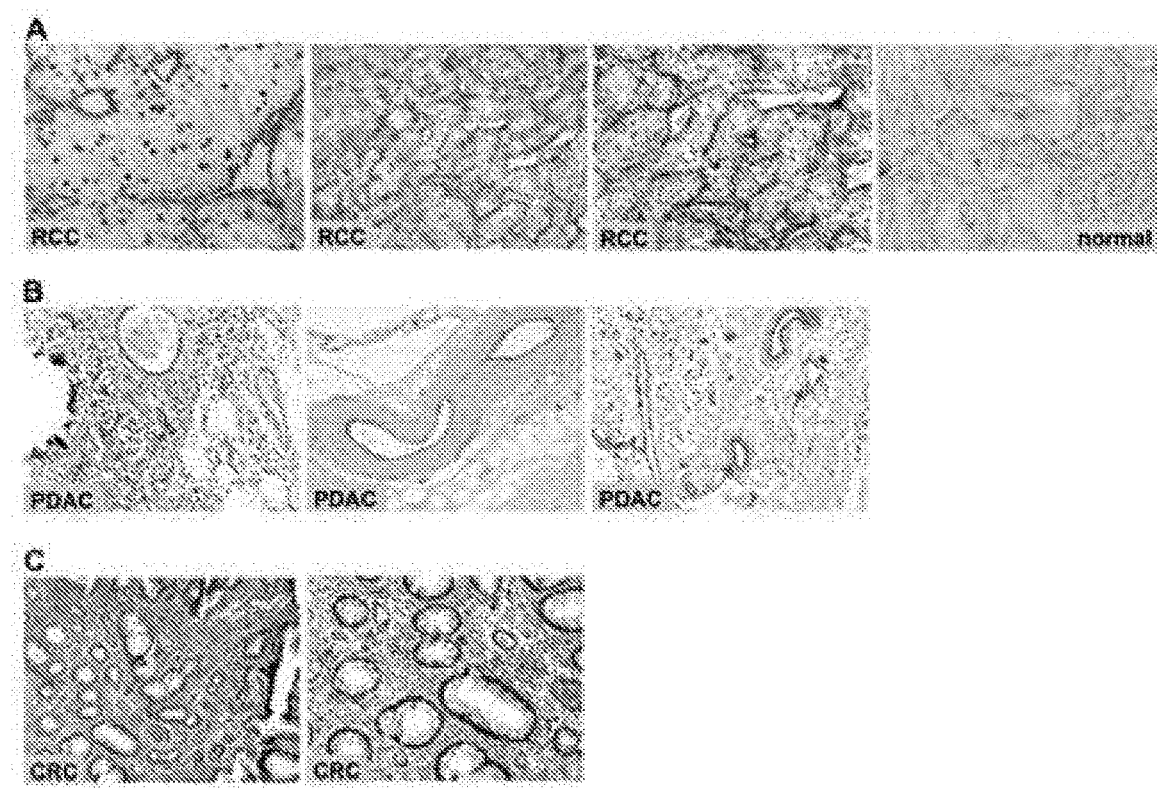

FIG. 23 shows the expression of the self antigen target CD93 in the tumor endothelium. A) Human renal cell carcinoma tissues and normal kidney were stained with an anti-CD93 antibody. Arrows indicate vascular expression of CD93. Picture 1, 3 and 4 have 200× magnification and picture 2 is magnified 100×. Normal kidney tissue is devoid of CD93 staining. B) CD93 is expressed in the vasculature of pancreatic adenocarcinoma (PDAC). Arrows indicate vascular expression of CD93. Magnification 200×. C) Expression of CD93 in the vasculature of colorectal carcinoma (CRC). Arrows indicate vascular expression of CD93. Magnification 200×.

Figure 24:
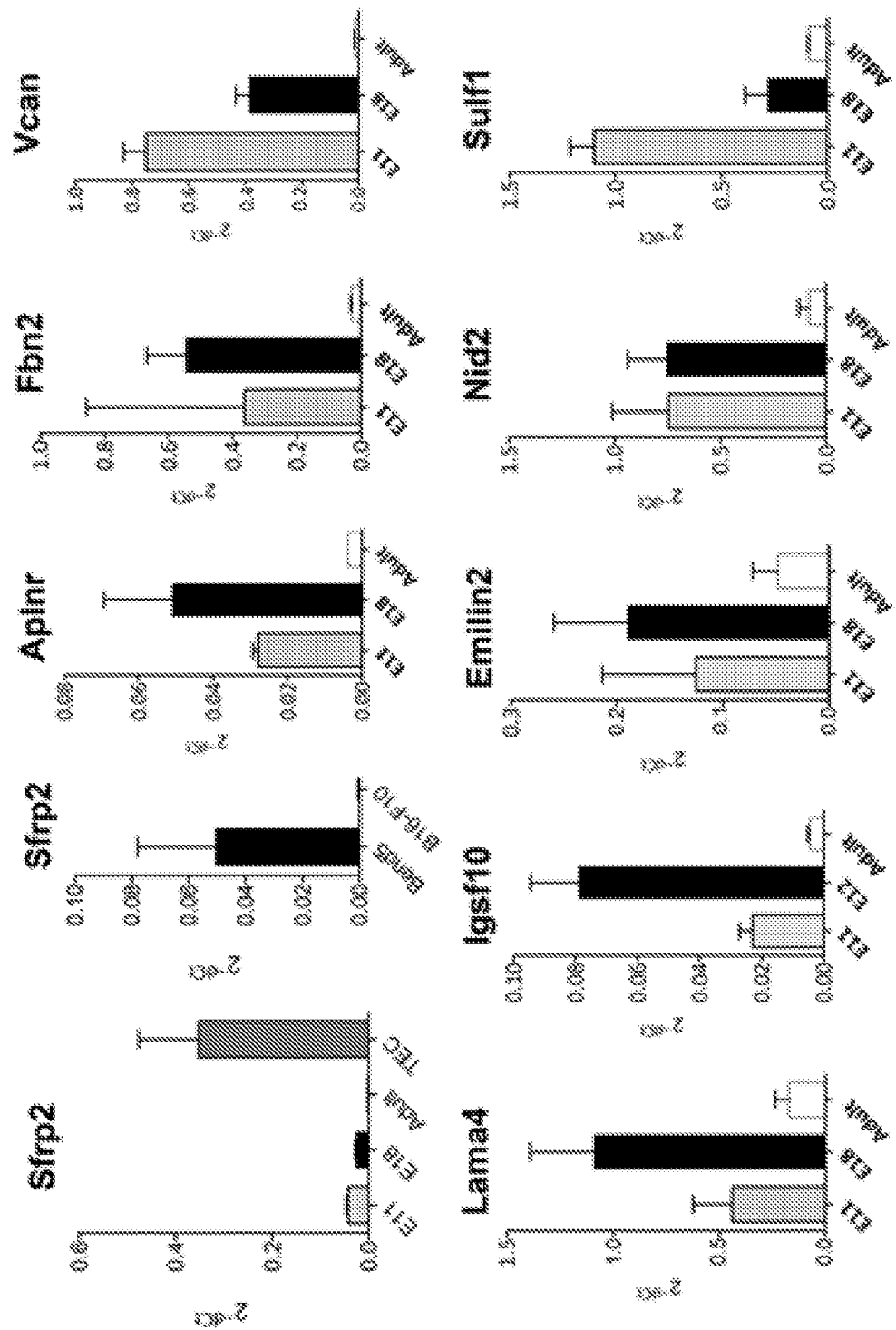

FIG. 24 shows mRNA expression (through RT-qPCR) of the self-antigen target genes Sfrp2, Aplnr, Fbn2, Vcan, Lama4, Igsf10, Emilin2, Nid2 and Sulf2 in embryo E11, embryo E18 and adult mouse. Sfrp2 mRNA is heavily upregulated in tumor endothelium (TEC). Also in the mouse endothelial cell line Bend5 Sfrp2 is expressed, whereas B16-F10 melanoma cells do not express Sfrp2.

Figure 25:
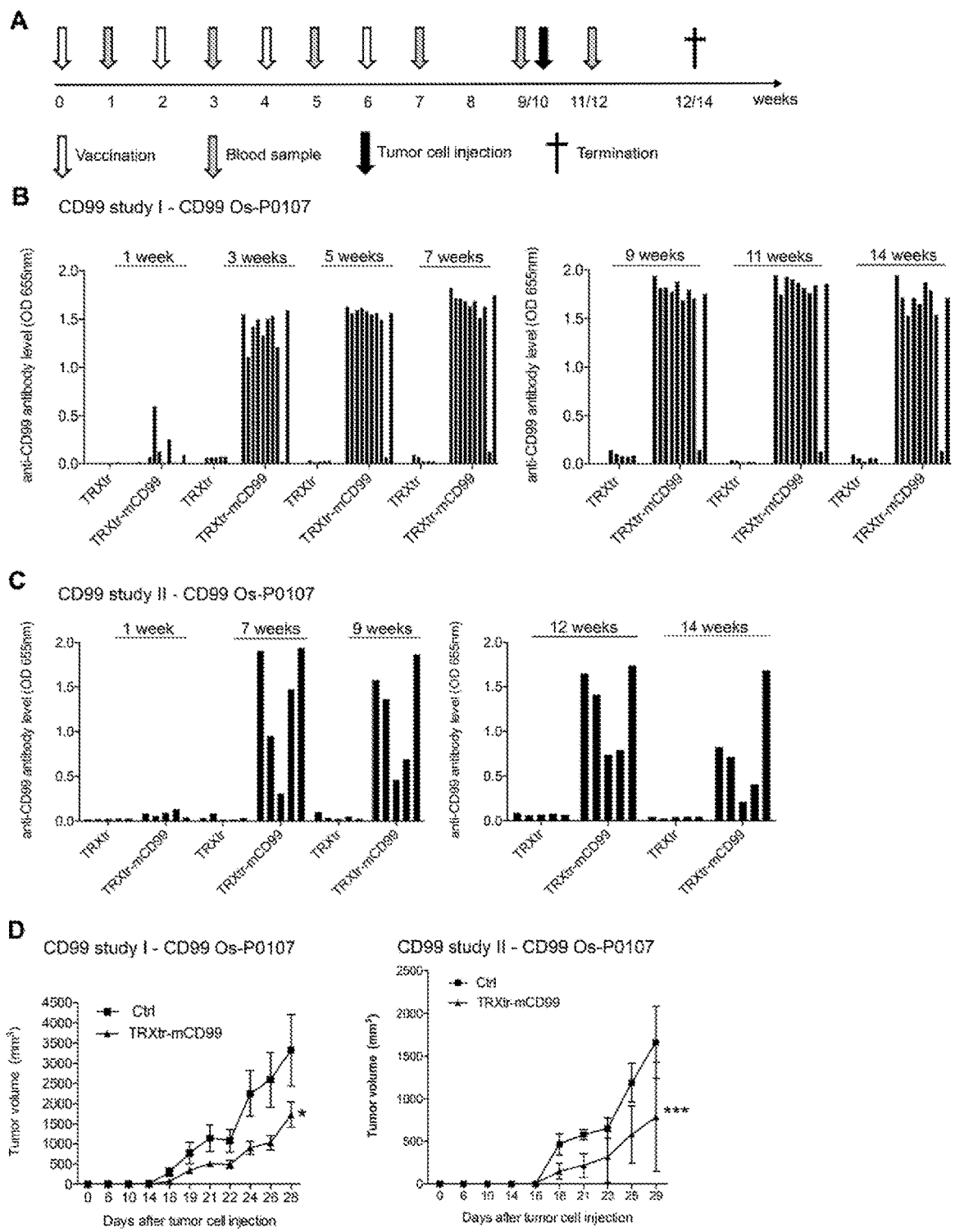

FIG. 25 shows that the induction of a humoral immune response against CD99 with a fusion polypeptide of the invention inhibits Ewing Sarcoma (EWS) tumor growth. A) Schematic illustration of the experimental set-up. Mice are vaccinated 4 times (white arrows). At set time-points blood samples are taken for measurement of anti-mCD99 antibodies in the sera of the mice (grey arrows). When anti-mCD99 levels are high, tumor cells are injected subcutaneously into the left flank of the mice (black arrow). Tumors are allowed to grow 3-5 weeks before the mice are sacrificed (cross). B)+C) Anti-mCD99 antibody levels in the sera of the C3H mice after 4 vaccinations, prior to tumor cell injection and 10 days after tumor cell injection. In the $1^{st}$ study (CD99 study I) all but one TRXtr-mCD99 vaccinated mouse (n=10, TRXtr-mCD99) responded with the production of anti-mCD99 antibodies, whereas in the sera of TRXtr vaccinated mice (n=5, TRXtr, control) no anti-mCD99 antibodies were present. In the $2^{nd}$ study (CD99 study II) all TRXtr-mCD99 vaccinated mice (n=5) responded with the production of anti-mCD99 antibodies and the control vaccinated mice (n=5, TRXtr) did not have any anti-mCD99 antibodies. D) Tumor growth curves of CD99 Os-P0107 in TRXtr-mCD99 vaccinated and control vaccinated mice (Ctrl). In both studies (CD99 study I, II) tumor growth was significantly inhibited in TRXtr-mCD99 vaccinated compared to control vaccinated mice. Tumor growth curves were compared by two-way ANOVA (*P<0.05; ***P<0.001).

Figure 26:
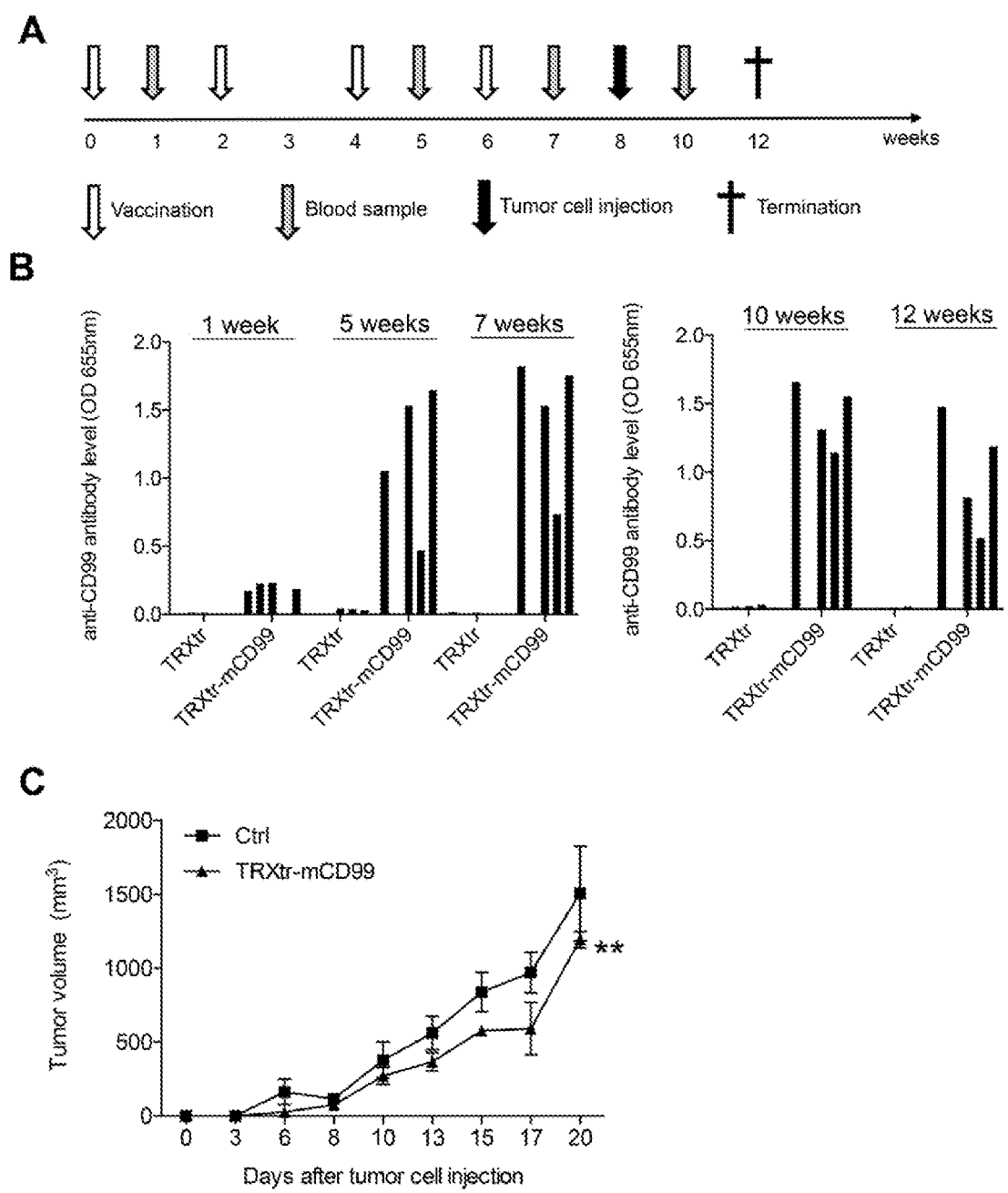

FIG. 26 shows that the induction of a humoral immune response against CD99 with a fusion polypeptide of the invention inhibits CT26 colon tumor growth. A) Schematic illustration of the experimental set-up. Mice are vaccinated 4 times (white arrows). At set time-points blood samples are taken for measurement of anti-mCD99 antibodies in the sera of the mice (grey arrows). When anti-mCD99 levels are high, tumor cells are injected subcutaneously into the left flank of the mice (black arrow). Tumors are allowed to grow 3-4 weeks before the mice are sacrificed (cross). B) Anti-mCD99 antibody levels in the sera of the BALB/c mice after 4 vaccinations, prior to tumor cell injection and 10 days after tumor cell injection. All TRXtr-mCD99 vaccinated mice (n=4, TRXtr-mCD99) responded with the production of anti-mCD99 antibodies, whereas in the sera of TRXtr vaccinated mice (n=5, TRXtr, control) no anti-mCD99 antibodies were present. C) Tumor growth curves of CT26 in TRXtr-mCD99 vaccinated and control vaccinated mice (Ctrl). Vaccination against CD99 does not entirely protect from tumor growth in this model (**P<0.01).

Figure 27:
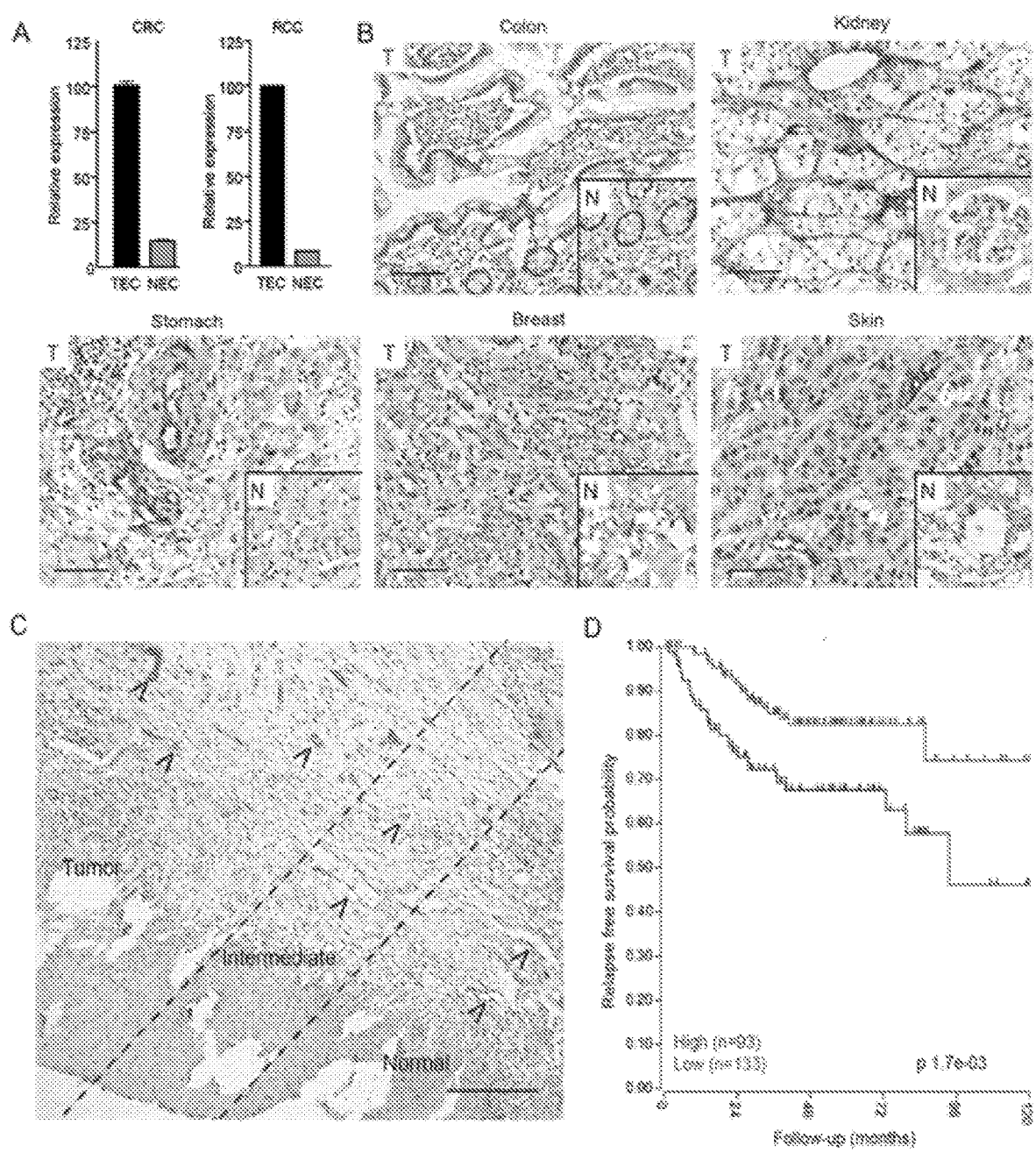

FIG. 27 shows that self antigen target insulin receptor (INSR) is overexpressed in tumor endothelial cells. (A) Overexpression of INSR in colorectal cancer (qPCR; (8)) and renal cell cancer (proteomics; (49)) associated endothelial cells. (B) Immunohistochemical staining for INSR on sections of different paraffin embedded human solid tumors (colon, kidney, stomach, breast, skin) and the INSR normal tissue counterparts. A clear induction of vascular staining (brown) is seen in tumors (T) as compared to normal tissues (insets; N). Scale bars represent 50 µm. (C) Immunohistochemical staining for INSR of human head and neck squamous carcinoma tissue with adjacent normal tissue. Overexpression of INSR is related to malignancy as strong vascular staining is observed in the tumor, less pronounced staining in the intermediate area and absence of staining in the adjacent normal tissue. Arrows heads highlight the blood vessels. The scale bar represents 200 µm. (D) Kaplan-Meier survival analysis of 226 CRC cases based on average INSR expression (high (n=93) is lower graph and low (n=133) is upper graph).

Figure 28:
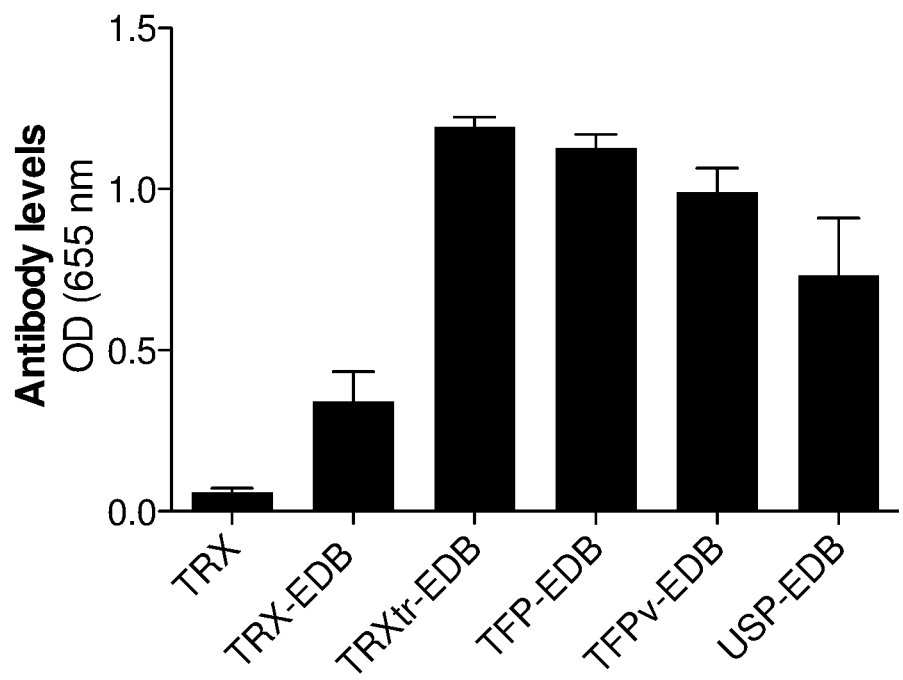

FIG. 28 shows on the y-axis anti-self antigen antibody levels (antibodies against EDB) induced with different fusion polypeptide constructs of the invention (TRX-EDB, TRXtr-EDB, TFP-EDB, TFPv-EDB and USP-EDB. All foreign antigens are superior to full-length TRX in inducing antibodies against the self-antigen EDB.

DETAILED DESCRIPTION OF THE INVENTION

Definitions and Embodiments

The term "immunogenic", as used herein, refers to the ability of a compound, for example formulated in a vaccine, to elicit an immune response, either humoral or cell-mediated, or both. If an antigen elicits such an immune response it is also referred to as an immunogen. Preferably, the immune response is a humoral immune response mediated primarily by B cells and helper T-cells. The skilled person is well aware of standard tests for measuring immunogenicity. It is well established that T-cell response can be determined with ELISPOT or ELISA, and that a humoral immune response can be determined with ELISA. An immunogenic composition as referred to herein is a pharmaceutical composition, preferably in the form of a suspension, emulsion or solution. The immunogenic compositions disclosed herein may or may not be immunoprotective or therapeutic. The term immunogenic composition is not intended to be limited to vaccines. Preferably the immunogenic composition is a vaccine such as a tumor vaccine, also referred to as a tumor antigen vaccine. An immunogenic composition is in general made under conditions allowing for administration to a subject, e.g., it is made under GMP conditions. An immunogenic composition of the invention may comprise pharmaceutically acceptable excipients, e.g., without limitation, emulsifiers (surfactants) stabilizers, bulking agents, buffers, carriers, diluents, vehicles, solubilizers, and binders. The skilled person understands that the selection of appropriate excipients depends on the route of administration and the dosage form, as well as the active ingredient and other factors. An immunogenic composition of the invention comprising foreign-self protein fusions is preferably adapted for administration by vaccination such as intramuscular or intradermal. An immunogenic composition of the invention comprising foreign-self protein fusions is preferably not for intravenous or other forms of parenteral administration. A composition of the invention comprising antiself antibodies (such as monoclonal antibodies) is preferably adapted for parenteral administration, such as intravenous administration and/or is preferably not for parenteral administration. An immunogenic composition or vaccine comprising foreign-self protein fusions may optionally comprise an adjuvant. Alternatively, the adjuvant is provided in a separate formulation and is administered before, after or essentially at the same time as administration of a foreign-self protein fusion of the invention. Administration of the adjuvant may occur via the same route of administration as foreign-self protein fusion, or via a different route of administration.

The term "antigen" generally refers to a biological molecule, usually a protein, peptide, polysaccharide, lipid or conjugate which contains at least one epitope to which a cognate antibody can selectively bind; or in some instances to an immunogenic substance, i.e. immunogen, that stimulates the production of antibodies or T-cell responses, or both, in a subject. The immune response may be generated against the whole molecule, or to one or more various portions of the molecule (e.g., an epitope or hapten). The term preferably refers to a polypeptide moiety. An antigen is recognized by antibodies, T-cell receptors or other elements of specific humoral and/or cellular immunity. The term "antigen" includes reference to at least one, or all, antigenic epitopes of polypeptide moieties or proteins described herein. Thus, when the term "antigen" is used in the context of polypeptide moieties described herein, also functional parts, i.e. a part of a polypeptide moiety against which an antigenic response is elicitable, are envisaged. In other words, also antigenic parts of the proteins or polypeptides moieties described herein are envisaged in a fusion polypeptide of the invention. Such antigenic parts preferably have a folded conformation corresponding to the antigenic part of the native, folded conformation of the full-length polypeptide moiety. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes may be identified by determining spatial conformation of amino acids such as by, e.g., x-ray crystallography and 2-dimensional nuclear magnetic resonance. See, e.g., Epitope Mapping Protocols, supra. Furthermore, for purposes of the present invention, an "antigen" may also be used to refer to a polypeptide moiety that includes modifications, such as deletions, additions and substitutions (generally conservative in nature, but they may be non-conservative), to the native sequence, as long as the polypeptide moiety maintains the ability to elicit an immunological response in a subject. These modifications may be deliberate, as through site-directed mutagenesis, or through particular synthetic procedures, or through a genetic engineering approach, or may be accidental, such as through mutations of hosts, which produce the antigens. Synthetic antigens are also included, for example, polyepitopes, flanking epitopes, and other recombinant or synthetically derived antigens (Bergmann et al. (1993) *Eur. J. Immunol.* 23:2777 2781; Bergmann et al. (1996) *J. Immunol.* 157:3242 3249; Suhrbier, A. (1997) *Immunol. and Cell Biol.* 75:402 408; Gardner et al. (1998) 12th World AIDS Conference, Geneva, Switzerland, Jun. 28-Jul. 3, 1998). In a fusion polypeptide of the invention, the antigen denoted as the self antigen is preferably of mammalian, more preferably of mouse, dog or human, more preferably of human, origin. Such a human antigen, if administration to a human individual as envisaged, is also referred to as a self-antigen. The self antigen, in the context of the invention, may be a self-antigen of any mammal, such as of a horse, dog, monkey, mouse, cat, rat, preferably a human. A self-antigen is in general not immunogenic when administered to a subject that is "self" in relation to the antigen. A preferred antigen is an antigen specific for angiogenesis, such as tumor-angiogenesis.

The term "immunogen", as used herein, refers to a compound such as a polypeptide capable of eliciting an immune response. In the context of the invention, an immunogen is also an antigen. As stated hereinabove, an antigen is not necessarily an immunogen. An immunogen is preferably of non-mammalian—such as bacterial—, origin and/or synthetic.

The term "fusion polypeptide" as used herein, refers to a polypeptide composed of at least two different polypeptide moieties, which are typically in their native, folded conformation and are generally joined by their respective amino and carboxyl termini through a peptide linker. The terms "polypeptide", "protein" and "peptide" are used interchangeably herein. These terms encompasses (poly)peptide analogs, which may have, for example, modifications rendering the peptides more stable while in a body or more capable of penetrating into cells. Such modifications include, but are not limited to, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH and backbone modifications. Methods for preparing peptidomimetic compounds are well known in the art and are specified, for example, in Quantitative Drug Design, C. A. Ramsden Gd., Chapter 17.2, F. Choplin, Pergamon Press (1992).

The term "hydrophilic, bulky amino acid residues", as used herein, refers to a group of amino acid residues consisting of histidine, glutamic acid, arginine, glutamine, aspartic acid and lysine. By way of experimentation, the inventors discovered that the immunogenic properties of an immunogen could be modulated by varying the percentage of hydrophilic and bulky amino acid residues in the immunogen denoted as the foreign antigen. When reference to a percentage of hydrophilic, bulky amino acid residues is made, it is meant that the sum of the number of hydrophilic, bulky amino acid residues in said immunogenic region of said foreign antigen is divided by the total number of amino acid residues in said immunogenic region, thus calculated over the full length of the immunogenic region. With respect to immunogenic regions defined with respect to SEQ ID NO:1, the percentage of hydrophilic, bulky amino acid residues is preferably 20-24%. With respect the immunogenic regions defined with respect to SEQ ID NO:2, the percentage of hydrophilic, bulky amino acid residues is preferably 14-22%. With respect to immunogenic regions defined with respect to SEQ ID NO:3, the percentage of hydrophilic, bulky amino acid residues is preferably 13-17%.

The term "clinically relevant immune response", as used herein, preferably refers to a serum level of immunoglobulins against a self antigen as referred to herein of at least 0.5%, preferably at least 1%, of the total serum immunoglobulin G (IgG) level in a subject.

The term "sequence identity", as used herein, refers to sequence identity between two amino acid (or nucleic acid) sequences, expressed as a percentage of amino acid (or nucleotide) residues that are identical upon comparison of two amino acid (or nucleic acid) sequences. Said comparison preferably is performed over the total length of the two amino acid (or nucleic acid) sequences. By way of example, according to this definition, a polypeptide having 10 amino acid residues can per definition maximally have 50% sequence identity to a polypeptide having 20 amino acid residues. Preferably, sequence identity is expressed as percentage of sequence similarity (i.e. identity) over the length of the entire protein.

The term "subject" refers to an animal, preferably a mammal such as a horse, dog, monkey, mouse, cat, rat, pig, Guinee pig, hamster, more preferably a human. The subject is preferably in need of administration of a foreign-self protein fusion, antibody, or composition of the invention, for therapy or diagnosis. The subject is preferably in need of administration of a foreign-self protein fusion, antibody, or composition of the invention, for therapy.

The term "foreign antigen" as used herein, refers to an antigen foreign to the immune system of a mammal, such as a bacterial antigen. The antigen may be part of a fusion protein.

The term "self antigen" as used herein, refers to an antigen that is "self" to the immune system of a mammal, such as a normal human protein. The self antigen may be part of a fusion protein. In the context of this disclosure, the term "self antigen" includes reference to mammalian polypeptides the expression of which is associated with tumor angiogenesis.

The term "truncation" or "truncated", as used in the context of fusion polypeptides of the invention, refers to an amino acid sequence that is not identical to its reference sequence, for the reason that, in comparison to that reference sequence, at least one amino acid residue is missing from the N-terminal and/or C-terminal end.

The term "serum", as used herein, refers to blood serum.

The term "linker peptide", as used herein, refers to amino acid sequences that connect or link at least two polypeptide moieties.

Cancers treatable using the fusion proteins, compositions and vaccines of the invention include carcinomas, sarcomas, leukaemias, lymphomas, and other types of cancer.

The term "tumor", as used herein, refers to a cellular mass exhibiting abnormal growth in tissue, which occurs when cellular proliferation is more rapid than proliferation of normal tissue and continues to grow after the stimuli that normally initiate growth cease. As used herein the term "tumor" includes cancer cells, necrosis, as well as stroma. Tumors generally exhibit partial or complete lack of structural organization and functional coordination with normal, healthy tissue, and usually form a distinct mass of tissue which may be benign or malignant. Preferably, the tumor treated or vaccinated against is a malignant tumor requiring tumor angiogenesis in order to continue growing and eventually metastasizing. More preferably, said tumor is a leukemia or a solid tumor or solid cancer, preferably selected from the group formed by sarcomas, carcinomas, and lymphomas. Exemplary solid tumors include but are not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioblastoma multiforme, astrocytoma, medulloblastoma, craniopharyngioma, ependymoma, pinealoma, hemangioblastoma, acoustic neuroma, oligodendroglioma, melanoma, neuroblastoma, and retinoblastoma.

The term "leukaemia" refers broadly to progressive, malignant diseases of the blood-forming organs and is generally characterized by a distorted proliferation and development of leukocytes and their precursors in the blood and bone marrow. Leukaemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukaemic or aleukaemic (subleukaemic). Accordingly, the present invention includes a method of treating leukaemia, and, preferably, a method of treating acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, a leukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stein cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "angiogenesis", as used herein, generally refers to the physiological process of blood vessel formation, preferably blood vessel formation from pre-existing blood vessels. The term "tumor angiogenesis", as used herein, refers to tumor-induced angiogenesis, i.e. the physiological process of tumor-induced blood vessel formation, preferably from pre-existing blood vessels, so as to secure blood supply to the tumor. In general, tumors growing beyond a certain diameter, e.g. about 1-2 mm, require tumor angiogenesis to continue growing.

The term "antigen as a self antigen", or "self antigen", as used in the context of the present invention, refers to an antigenic polypeptide moiety. Preferably, such a polypeptide moiety is specific to tumor angiogenesis and not specific to non-tumor related angiogenesis, such as wound healing. The present inventors have provided a comprehensive list of such polypeptide moieties, based on a highly specific and novel screening method as described in Example 1. These moieties can be conjugated to an immunogen, as described herein, by their full length or a part thereof so as to present or display at least one epitope or antigenic determinant. The self antigen may be a structural component of a blood vessel formed during tumor angiogenesis, preferably a structural component specific to a blood vessel formed in tumor angiogenesis and not specific to a blood vessel formed in non-tumor related angiogenesis, such as a polypeptide moiety, or a part thereof, selected from the group formed by, or consisting of, tissue inhibitor of metalloproteinase 1 (Timp1), apelin (Apln), serum amyloid A3 (Saa3), CD93 antigen (CD93), heart development protein with EGF-like domains 1 (Heg1), Notch 4, apelin receptor (Aplnr), nestin (Nes), tenascin C (Tnc), pentraxin related gene (Ptx3), vimentin (Vim), prostate specific membrane antigen (PSMA), human EGF receptor-2 (HER2), HER3, tumor necrosis factor alpha induced protein 6 (Tnfaip6), carboxypeptidase Z (Cpz), snail family zinc finger 1 (Snai1), premelanosome protein (Pmel), arylsulfatase I (Arsi), WNT1 inducible signaling pathway protein 1 (Wisp1), glutathione peroxidase 7 (Gpx7), a disintegrin-like and metallopeptidase (reprolysin type) with thrombospondin type 1 motif, 4 (Adamts4), endothelial cell-specific molecule 1 (Esm1), integrin alpha 5 (fibronectin receptor alpha) (Itga5), a disintegrin-like and metallopeptidase (reprolysin type) with thrombospondin type 1 motif, 2 (Adamts2), thrombospondin 2 (Thbs2), matrix metallopeptidase 14 (membrane-inserted) (Mmp14), insulin-like growth factor binding protein 3 (Igfbp3), thrombospondin 1 (Thbs1), fibrillin 1 (Fbn1), periostin, osteoblast specific factor (Postn), leucine rich repeat containing 17 (Lrrc17), fibrillin 2 (Fbn2), cerebral endothelial cell adhesion molecule (Cercam), secreted frizzled-related protein 4 (Sfrp4), C1q and tumor necrosis factor related protein 6 (C1qtnf6), lysyl oxidase-like 3 (Loxl3), immunoglobulin superfamily, member 10 (Igsf10), secreted frizzled-related protein 2 (Sfrp2), FK506 binding protein 10 (Fkbp10), glutamine fructose-6-phosphate transaminase 2 (Gfpt2), carboxypeptidase X 1 (Cpxm1), microfibrillar associated protein 5 (Mfap5), epidermal growth factor-containing fibulin-like extracellular matrix protein 2 (Efemp2), nephroblastoma overexpressed gene (Nov), versican (Vcan), elastin (Eln), cysteine rich protein 61 (Cyr61), sulfatase 1 (Sulf1), nidogen 2 (Nid2), CD248 antigen, endosialin (Cd248), lysyl oxidase-like 2 (Loxl2), follistatin-like 1 (Fstl1), sushi, von Willebrand factor type A, EGF and pentraxin domain containing 1 (Svep1), laminin, alpha 4 (Lama4), slit homolog 3 (Slit3), mannose receptor, C type 2 (Mrc2), cytoskeleton-associated protein 4 (Ckap4), G protein-coupled receptor 133 (Gpr133), fascin homolog 1, actin bundling protein (Fscn1), elastin microfibril interfacer 2 (Emilin2), scavenger receptor class A, member 3 (Scara3), serine (or cysteine) peptidase inhibitor, clade B, member 2 (Serpinb2), chemokine (C—C motif) ligand 2 (Ccl2), insulin receptor (Insr), folate hydrolase 1 (Folh1), CD99 antigen (CD99), casein kappa (Csn3), calcitonin receptor-like (Calcrl), activin A receptor, type II-like 1 (Acvrl1), colony stimulating factor 3 receptor (Csf3r), chloride channel calcium activated 2 (Clca2), C-type lectin domain family 14, member a (Clec14a), transmembrane protein 100 (Tmem100), cysteine and tyrosine-rich protein 1 (Cyyr1), alkaline ceramidase 2 (Acer2), trichorhinophalangeal syndrome I (Trps1), ArfGAP with RhoGAP domain, ankyrin repeat and PH domain 3 (Arap3), integrin alpha 8 (Itga8), sema domain, immunoglobulin domain (Ig), short basic domain, secreted, (semaphorin) 3G (Sema3g), transmembrane protein 2 (Tmem2), tumor necrosis factor (ligand) superfamily, member 10 (Tnfsf10), HOP homeobox (Hopx), lactalbumin, alpha (Lalba), phosphatidylinositol-3,4,5-trisphosphate-dependent Rac exchange factor 2 (Prex2), mucin 15 (Muc15), rhotekin 2 (Rtkn2), SRY (sex determining region Y)-box 4 (Sox4), tetraspanin 18 (Tspan18), G protein-coupled receptor 126 (Gpr126), C-type lectin domain family 1, member a (Clec1a), extra domain-B of fibronectin (ED-B) and hairy/enhancer-of-split related with YRPW motif 1 (Hey1) as indicated in Tables 1 and 2. More preferably, the polypeptide moieties are specific to (i) embryonic tissue and (ii) blood vessels formed in tumor angiogenesis, or (iii) tumor cells. Even more preferably, the self antigen is selected from the group formed by or consisting of vimentin (Vim), CD93, CD99, HER2, HER3, prostate specific membrane antigen (PSMA). Based on the screening method as described herein, the skilled person is able to identify further self antigens that fulfill the aforementioned criteria.

The term "blood vessel", as used herein, may refer to part of the vascular system comprised of endothelial cells, extracellular matrix, a basal membrane.

The term "tumor vasculature", as used herein, refers to a system of blood vessels, recruited during tumor angiogenesis, securing a blood supply to the tumor. One skilled in the art can identify tumor vasculature on the basis of blood vessel structure parameters such as extracellular matrix composition and/or vascular permeability by using (electron)microscopy.

The term "adjuvant", as used herein, refers to a compound that enhances the immune response of a subject to an antigen, e.g. a polypeptide of the invention when administered with that polypeptide. The adjuvant is preferably a pharmaceutically acceptable adjuvant, such as Montanide ISA 720 (Seppic SA, France), granulocyte-monocyte colony stimulating factor (GM-CSF), Freund's complete adjuvant (F5881, Sigma-Aldrich), preferably for primer vaccinations, Freund's incomplete adjuvant (F5506, Sigma-Aldrich), preferably for booster vaccinations. Adjuvants may be co-formulated in an immunogenic composition of the invention, or may be provided in a further, alternative formulation.

The term "typing", as used herein, refers to differentiating or stratifying between subjects according to a tumor angiogenesis status or tumor vasculature status. The typing is preferably based on a comparison of (i) a gene expression level of at least one gene expression product in a sample of a subject and (ii) a gene expression control value. Preferably, the typing differentiates subjects suffering, or suspected to suffer from, a tumor, preferably of malignant tumor, in a group having an increased risk of tumor metastasis and a group not having such an increased risk.

The term "sample", as used herein refers to a biological sample encompassing a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The term "tumor angiogenesis status", as used herein, refers to a stratification in (i) a group that is found to be positive for tumor angiogenesis status—presence of tumor angiogenesis—based on the gene expression level of at least one gene expression product in said sample of said subject as compared to said gene expression control value, or (ii) a group that is found to be negative for tumor angiogenesis status—absence of tumor angiogenesis—based on the gene expression level of said at least one gene expression product in said sample of said subject as compared to said gene expression control value.

The term "gene expression product", as used herein, includes inter alia RNA products and protein products, including (poly)peptides. The skilled person is aware of quantitative methods for measuring gene expression product levels, such as micro-array analysis, northern blotting, western blotting for proteins, ELISA, quantitative RT-PCR and next-generation sequencing. Preferably, in the context of a method of typing of the invention, the gene expression level is measured by RNA sequencing and/or quantitative (RT-)PCR.

The term "gene expression control value", as used herein, is a cut-off value providing a demarcation between a positive and a negative tumor angiogenesis status or tumor vasculature status. Said control value is preferably a pre-determined similarity threshold value set at a value at which an acceptable number of subjects with a status that is positive would score as false negatives, and an acceptable number of patients with a status that is negative would score as false positives. A similarity threshold value is preferably displayed or outputted to a user interface device, a computer readable storage medium, or a local or remote computer system. The person skilled in the art is well aware of statistical methods to develop such a similarity threshold value. Alternatively, said gene expression control value can be obtained by measuring the gene expression level of said at least one gene expression product in a sample comprising non-tumor cells, preferably non-tumor endothelial cells, more preferably non-tumor vascular endothelial cells of a human subject, preferably the same human subject as is being typed. In the same context, said control sample is preferably obtained from the same tissue or organ as where the tumor is located.

Description of the Preferred Embodiments

Immunogenic Compositions and Fusion Polypeptides of the Invention

The present invention relates inter alia to an immunogenic composition comprising a fusion polypeptide comprising an antigen as a self antigen, and an immunogen as a foreign antigen, wherein said foreign antigen comprises a truncated immunogenic region of 45-70 consecutive amino acid residues of the protein of SEQ ID NO:1 or of a protein having at least 90% sequence identity to the protein of SEQ ID NO:1; or wherein said foreign antigen comprises a truncated immunogenic region of 110-150 consecutive amino acid residues of the protein of SEQ ID NO:2 or of a protein having at least 90% sequence identity to the protein of SEQ ID NO:2; or wherein said foreign antigen comprises an immunogenic region of 45-61 consecutive amino acid residues of the protein of SEQ ID NO:3 or of a protein having at least 90% sequence identity to a protein of SEQ ID NO:3, and wherein said immunogenic region comprises 12-24% of hydrophilic, bulky amino acid residues selected from the group consisting of histidine, glutamate, arginine, glutamine, aspartic acid and/or lysine.

Preferably, said immunogenic composition elicits in a subject a clinically relevant immune response in the sense that a serum level of immunoglobulins against said self antigen of at least ELISA-detectable levels of immunoglobulins directed against the self antigen is achieved. ELISA-detectable levels refer to statistically significant detection above background or above a control or threshold value in an ELISA protocol. Preferably, said relevant immune response involves a serum level of immunoglobulins against said self antigen of at least 5 times the signal measured in control serum of non-vaccinated individuals, detected by ELISA, preferably identical with at least 0.1% of the total serum immunoglobulin G (IgG) level.

It is further preferred that said immunogenic region comprises 12-24% of hydrophilic, bulky amino acid residues selected from the group consisting of histidine, glutamate, arginine, glutamine, aspartic acid and/or lysine.

It was unexpectedly found that certain immunogenic amino acid residue regions of a protein having the amino acid sequence of SEQ ID NO:1 and SEQ ID NO:2 or proteins showing at least 90% sequence identity to SEQ ID NO:1 or SEQ ID NO:2, are advantageously used as fusion partners with antigenic polypeptide moieties, as described herein, in that they, when fused to such a polypeptide moiety and administered as an immunogenic composition, facilitate the elicitation of a relevant (or effective) immune response against said antigenic polypeptide moieties (FIGS. 2-6). It was thus established that elicitation of self-antibody levels depends on the characteristics of the fusion partner.

In addition, an artificial polypeptide (USP) having the amino acid sequence of SEQ ID NO:3 was designed and produced in bacteria. The same effect was found for this polypeptide.

The amino acid sequence of thioredoxin-1 (TRX) is provided in SEQ ID NO:1. TRX is a bacterial protein participating in various redox reactions through the reversible oxidation of its active center dithiol to a disulfide and catalyzes dithiol-disulfide exchange reactions.

The amino acid sequence of type-1 fimbrial protein, A chain (TFP) is provided in SEQ ID NO:2. TFP is a constituent of fimbriae, i.e. polar filaments radiating from the surface of a bacterium, generally of a length of 0.5-1.5 micrometers, enabling bacteria to colonize foreign hosts.

Preferably, or alternatively, said protein having at least 90% sequence identity to the protein of SEQ ID NO:1 is a peptide having at least 90% sequence identity to an amino acid residue region of 45-70, such as 46, 47, 48, 49, 50, 51, 52, 53, 54, 55, 56, 57, 58, 59, 60, 61, 62, 63, 64, 65, 66, 67, 68 or 69, consecutive amino acid residues of the protein of SEQ ID NO:1; and wherein said protein having at least 90% sequence identity to the protein of SEQ ID NO:2 is a polypeptide having at least 90% sequence identity to an amino acid residue region of 110-150, such as 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148 or 149, consecutive amino acid residues of the protein of SEQ ID NO:2; and wherein said protein having at least 90% sequence identity to a protein of SEQ ID NO:3 is a polypeptide having at least 90% sequence identity to a amino acid residue region of 45-61, such as 46, 47, 48, 49, 50, 51, 52, 53, 54, 55, 56, 57, 58, 59 or 60, consecutive amino acid residues of the protein of SEQ ID NO:3. The skilled person understands that herewith the reference protein is further defined, i.e. defined as a specific amino acid residue region of the proteins of SEQ ID NOs:1-3.

More preferably, said truncated immunogenic region of 45-70 consecutive amino acid residues is in the region of Ala-30 to Ala-109, preferably the region of Gln-52 to Ala-109, of the protein of SEQ ID NO:1; and wherein said truncated immunogenic region of 110-150 consecutive amino acid residues is the region of Ala-24 to Ile-154 of the protein of SEQ ID NO:2.

The truncated immunogenic region of 45-70 consecutive amino acid residues is preferably a region of 45-65, more preferably 50-61, and most preferably 58, amino acid residues, preferably of SEQ ID NO:1. Alternatively, the truncated immunogenic region of 45-70 consecutive amino acid residues has a length of 46, 47, 48, 49, 50, 51, 52, 53, 54, 55, 56, 57, 58, 59, 60, 61, 62, 63, 64, 65, 66, 67, 68 or 69 amino acid residues.

Preferably, in a polypeptide of the invention, the antigen foreign to the immune system of a mammal does not comprise or consist of a truncated protein of SEQ ID NO:1 consisting of amino acid residues 1-75 of SEQ ID NO:1, amino acid residues 1-74 of SEQ ID NO:1, or amino acid residues 1-80 of SEQ ID NO:1.

In preferred embodiments of the invention, a truncated immunogenic region of the protein of SEQ ID NO:1 or of a protein having at least 90% sequence identity to the protein of SEQ ID NO:1 (TRX-trunc, or TRXtr) is generated by cleaving the molecule between amino acid 51 (Gln, Q) and 52 (Gly, G) and thereby removing the N-terminal part. TRXtr, in preferred embodiments of the invention, preferably comprises or contains the C-terminal 58 amino acids of the TRX molecule of SEQ ID NO: 1. The cleavage site is preferably chosen so that the molecule is split in between the two globular domains of TRX. The C-terminal domain is then preferably selected as a truncated TRX (TRXtr) molecule. Preferably, the TRXtr molecule in aspects of this invention comprises (i) 3 remaining beta-sheet domains of the original TRX molecule, in combination with (ii) the terminal C terminal part of the molecule comprising an alpha-helix. Preferably, the number of B-cell epitopes in TRXtr is reduced, while antigenicity is maintained by inclusion of both the beta-sheet domains and a free terminal alpha-helix domain, which likely to contain B-cell epitopes.

Without wishing to be bound by theory, a shorter TRXtr protein by cleaving the protein at positions 53-60 is considered to (i) induce too much reduction of antigenicity (loss of beta-sheet 3 domain) and (ii) prevent the proper folding of the molecule, which is considered to give rise to loss of antigenicity. Without wishing to be bound by theory, a longer TRXtr by cleaving at amino acid 40-49 is considered not likely to meet the goal of reduced antigenicity, because thereby an extra (N-terminal) alpha-helix domain is maintained.

In the design of alternative non-self parts of the vaccines of the present invention, molecules with a large percentage of bulky and charged amino acids are preferably selected. This may render the conjugate protein of the invention both immunogenic and soluble, respectively. As can be seen in FIG. 28, all alternative constructs result in high antibody titers against the self-antigen EDB. The relevance of these bulky and charged amino acids is demonstrated by the fact that the USP construct, displaying a lower percentage of these amino acids (see table A, below), induces lower antibody titers against the self-antigen. Bulky and charged amino acids as referred to herein are preferably selected from glutamine (Q), arginine (R), histidine (H), Lysine (K), Aspartic acid (D), and glutamic acid (E).

TABLE A

Molecular characteristics of the different non-self fusion partners.

|  | Bulky hydrophilic/ charged aa | Total[1] | Ratio[2] | Percentage[3] |
| --- | --- | --- | --- | --- |
| TRX | 31 | 109 | 0.40 | 28% |
| TRXtr | 14 | 58 + M[4] | 0.31 | 24% |
| TFP | 23 | 132 | 0.21 | 17% |
| TFPv | 27 | 132 | 0.26 | 20% |
| CDP | 10 | 61 | 0.20 | 16% |

[1]Total number of amino acids in the protein
[2]Ratio of bulky hydrophilic/charged amino acids and remaining amino acids
[3]Percentage bulky hydrophilic/charged in the total protein
[4]Total 59 aa (58 aa + methionine; start site codon)

The truncated immunogenic region of 110-150 consecutive amino acid residues is preferably a region of 110-140, more preferably 125-135, and most preferably 131, amino acid residues, preferably of SEQ ID NO:2. Alternatively, the truncated immunogenic region of 110-150 consecutive amino acid residue has a length of 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148 or 149 amino acid residues, preferably of SEQ ID NO:2.

The truncated immunogenic region of 110-150 consecutive amino acid residues is preferably the amino acid sequence of SEQ ID NO:6 or 7.

Most preferably, the foreign antigen consists of the amino acid sequence of SEQ ID NOs:3, 4, 6 or 7.

A foreign antigen of the fusion polypeptide of the invention preferably further comprises a N-terminal methionine residue. In one preferred embodiment, the foreign antigen as described herein is linked at its N-terminus of the self antigen. It is thus, for instance, envisaged herein that SEQ ID NOs: 4, 6 or 7 are linked to the self antigen through an N-terminal methionine residue. In another preferred embodiment, the foreign antigen as described herein is linked at its C-terminus of the self antigen. It is thus, for instance, envisaged herein that SEQ ID NOs: 4, 6 or 7 are linked to an N-terminal methionine residue.

A polypeptide of the invention may further comprise one or more additional amino acid sequences, in addition to the self and foreign antigens, such as for example an amino acid sequence that constitutes a tag, for example a FLAG tag as described in EP0150126, and/or one or more other identification peptides such as a His-tag. Also, a fusion polypeptide of the invention may comprise a further antigen as an "additional" and/or "further" self antigen as described herein, and/or an "additional" and/or "further" foreign antigen as described herein.

A fusion polypeptide of the invention preferably further comprises a linker peptide such as a glycine-serine (GS), preferably repetitive, linker peptide.

Preferably, the self antigen is a specific disease antigen or is expressed specifically during disease, including the angiogenesis of disease, such as in cancer, atherosclerosis, psoriasis, arthritis, endometriosis or adiposity, or is expressed in tumor cells, rheuma), preferably selected from the group formed by, or consisting of, tissue inhibitor of metalloproteinase 1 (Timp1), apelin (Apln), serum amyloid A3 (Saa3), CD93 antigen (Cd93), heart development protein with EGF-like domains 1 (Heg1), Notch 4, apelin receptor (Aplnr), nestin (Nes), tenascin C (Tnc), pentraxin related gene (Ptx3), vimentin (Vim), tumor necrosis factor alpha induced protein 6 (Tnfaip6), carboxypeptidase Z (Cpz), snail family zinc finger 1 (Snai1), premelanosome protein (Pmel), arylsulfatase I (Arsi), WNT1 inducible signaling pathway protein 1 (Wisp1), glutathione peroxidase 7 (Gpx7), a disintegrin-like and metallopeptidase (reprolysin type) with thrombospondin type 1 motif, 4 (Adamts4), endothelial cell-specific molecule 1 (Esm1), integrin alpha 5 (fibronectin receptor alpha) (Itga5), a disintegrin-like and metallopeptidase (reprolysin type) with thrombospondin type 1 motif, 2 (Adamts2), thrombospondin 2 (Thbs2), matrix metallopeptidase 14 (membrane-inserted) (Mmp14), insulin-like growth factor binding protein 3 (Igfbp3), thrombospondin 1 (Thbs1), fibrillin 1 (Fbn1), periostin, osteoblast specific factor (Postn), leucine rich repeat containing 17 (Lrrc17), fibrillin 2 (Fbn2), cerebral endothelial cell adhesion molecule (Cercam), secreted frizzled-related protein 4 (Sfrp4), C1q and tumor necrosis factor related protein 6 (C1qtnf6), lysyl oxidase-like 3 (Loxl3), immunoglobulin superfamily, member 10 (Igsf10), secreted frizzled-related protein 2 (Sfrp2), FK506 binding protein 10 (Fkbp10), glutamine fructose-6-phosphate transaminase 2 (Gfpt2), carboxypeptidase X 1 (Cpxm1), microfibrillar associated protein 5 (Mfap5), epidermal growth factor-containing fibulin-like extracellular matrix protein 2 (Efemp2), nephroblastoma overexpressed gene (Nov), versican (Vcan), elastin (Eln), cysteine rich protein 61 (Cyr61), sulfatase 1 (Sulf1), nidogen 2 (Nid2), CD248 antigen, endosialin (Cd248), lysyl oxidase-like 2 (Loxl2), follistatin-like 1 (Fstl1), sushi, von Willebrand factor type A, EGF and pentraxin domain containing 1 (Svep1), laminin, alpha 4 (Lama4), slit homolog 3 (Slit3), mannose receptor, C type 2 (Mrc2), cytoskeleton-associated protein 4 (Ckap4), G protein-coupled receptor 133 (Gpr133), fascin homolog 1, actin bundling protein (Fscn1), elastin microfibril interfacer 2 (Emilin2), scavenger receptor class A, member 3 (Scara3), serine (or cysteine) peptidase inhibitor, clade B, member 2 (Serpinb2), chemokine (C—C motif) ligand 2 (Ccl2), insulin receptor (Insr), folate hydrolase 1 (Folh1), CD99 antigen (CD99), casein kappa (Csn3), calcitonin receptor-like (Calcrl), activin A receptor, type II-like 1 (Acvrl1), colony stimulating factor 3 receptor (Csf3r), chloride channel calcium activated 2 (Clca2), C-type lectin domain family 14, member a (Clec14a), transmembrane protein 100 (Tmem100), cysteine and tyrosine-rich protein 1 (Cyyr1), alkaline ceramidase 2 (Acer2), trichorhinophalangeal syndrome I (Trps1), ArfGAP with RhoGAP domain, ankyrin repeat and PH domain 3 (Arap3), integrin alpha 8 (Itga8), sema domain, immunoglobulin domain (Ig), short basic domain, secreted, (semaphorin) 3G (Sema3g), transmembrane protein 2 (Tmem2), tumor necrosis factor (ligand) superfamily, member 10 (Tnfsf10), HOP homeobox (Hopx), lactalbumin, alpha (Lalba), phosphatidylinositol-3,4,5-trisphosphate-dependent Rac exchange factor 2 (Prex2), mucin 15 (Muc15), rhotekin 2 (Rtkn2), SRY (sex determining region Y)-box 4 (Sox4), tetraspanin 18 (Tspan18), G protein-coupled receptor 126 (Gpr126), C-type lectin domain family 1, member a (Clec1a), extra domain-B of fibronectin (ED-B) and hairy/enhancer-of-split related with YRPW motif 1 (Hey1) as indicated in Tables 1 and 2.

In an alternatively preferred embodiment of aspects of this invention, the self antigen is a specific disease antigen selected from Vim and CD99. These self antigens have an anti-tumor effect.

In another alternatively preferred embodiment of aspects of this invention, the self antigen is CD93 antigen. This self antigen is high in METs and especially beneficial in aspects of this invention.

In yet another alternatively preferred embodiment of aspects of this invention, the self antigen is a specific disease antigen selected from the group consisting of Mmp14, Cercam, Sulf1, Gpr133, Scara3, Insr, Folh1, CD99, Acvrl1, Itga8, Muc15. These self antigens are membrane antigens.

In yet another alternatively preferred embodiment of aspects of this invention, the self antigen is a specific disease antigen selected from the group consisting of Timp1, Apln, Saa3, Ptx3, Tnfaip6, Cpz, Pmel, Arsi, Adamts4, Thbs2, Mmp14, Igfbp3, Thbs1, Fbn1, Postn, Loxl3, Mfap5, Efemp2, Nov, Vcan, Eln, Cyr61, Sulf1, Nid2, Lama4, Slit3, Mrc2, Serpinb2, Ccl2, CD99, Tnfsf10, Lalba. These self antigens are secreted antigens.

In yet another alternatively preferred embodiment of aspects of this invention, the self antigen is a specific disease antigen selected from the group consisting of Apln, Saa3, Vim, Pmel, Arsi, Wisp1, Fkbp10. These self antigens are cytoplasmatic targets.

In yet another alternatively preferred embodiment of aspects of this invention, the self antigen is a specific disease antigen selected from the group consisting of Timp1, Apln, Saa3, Ptx3, Vim, Tnfaip6, Cpz, Arsi, Esm1, Itga5, Adamts2, Thbs2, Mmp14, Thbs1, Fbn1, Postn, Fbn2, Cercam, Loxl3, Mfap5, Efemp2, Nov, Vcan, Eln, Cyr61, Sulf1, Nid2, Lama4, Slit3, Mrc2, Gpr133, Scara3, Insr, Folh1, CD99, Acvrl1, Eln, Itga8, Tnfsf10, Lalba, Muc15. These self antigens are extracellular targets.

In yet another alternatively preferred embodiment of aspects of this invention, the self antigen is a specific disease antigen selected from the group consisting of Cd93, Heg1, Notch4, Aplnr, Nes, Tnc, Snai1, Gpx7, Lrrc17, Sfrp4, C1qtnf6, Igsf10, Sfrp2, Gfpt2, Cpxm1, Cd248, Loxl2, Fstl1, Svep1, Ckap4, Emilin2, Csn3, Calcrl, Csf3r, Clca2, Clec14a, Tmem100, Cyyr1, Acer2, Trps1, Arap3, Sema3g, Tmem2, Hopx, Prex2, Rtkn2, Sox4, Tspan18, Gpr126, Clec1a, Hey1. These self antigens are involved in various disease related processes.

In yet another alternatively preferred embodiment of aspects of this invention, the self antigen is a specific disease antigen selected from the group consisting of Timp1, Apln, Saa3, Cd93, Heg1, Notch4, Aplnr, Nes, Tnc, Ptx3, Vim, Tnfaip6, Cpz, Snai1, Pmel, Arsi, Wisp1, Gpx7, Adamts4, Esm1, Itga5, Adamts2, Thbs2, Mmp14, Igfbp3, Thbs1, Fbn1, Postn, Lrrc17, Fbn2, Cercam, Sfrp4, C1qtnf6, Loxl3, Igsf10, Sfrp2, Fkbp10, Gfpt2, Cpxm1, Mfap5, Efemp2, Nov, Vcan, Eln, Cyr61, Sulf1, Nid2, Cd248, Loxl2, Fstl1, Svep1, Lama4, Slit3, Mrc2, Ckap4, Gpr133, Fscn1, Emilin2, Scara3, Serpinb2, Ccl2, Insr, Folh1, CD99. These self antigens are involved in tumor development.

In yet another alternatively preferred embodiment of aspects of this invention, the self antigen is a specific disease antigen selected from the group consisting of Csn3, Calcrl, Acvrl1, Csf3r, Clca2, Clec14a, Tmem100, Cyyr1, Eln, Acer2, Trps1, Arap3, Itga8, Sema3g, Tmem2, Tnfsf10, Hopx, Lalba, Prex2, Muc15, Rtkn2, Sox4, Tspan18, Gpr126, Clec1a, Hey1. These self antigens are involved in metastasis.

Preferred embodiments of this and other aspects of this invention include embodiments wherein the self antigen is at least 1, 2, 3, 4, 5, 6, 7, 8, 9, 10, or more self antigens selected from the self antigen groupings indicated in FIGS. 9-17.

Preferably, the self antigen is extra domain-B of fibronectin or vimentin. More preferably, the self antigen is human extra domain-B of fibronectin or human vimentin.

Human extra-domain B of fibronectin is a 91 amino acid residue domain inserted into fibronectin by alternative splicing and is expressed during vasculogenesis in the embryo, but essentially undetectable under normal conditions in the human body. However, the extra-domain B is highly expressed during tumor angiogenesis. The human fibronectin 1 gene is provided in Genbank under Genbank Accession number NG_012196.1.

A self antigen as described herein is preferably the N-terminal or C-terminal part of the fusion polypopeptide, more preferably the C-terminal part, in a fusion polypeptide of the invention. Said self antigen is preferably conjugated to a foreign antigen by linking the N-terminal part of said self antigen to the C-terminal part of the foreign antigen. The skilled person is aware of methods and means for producing fusion polypeptides that comprise polypeptide moieties in their folded, native spatial conformation (Druzinec et al., *Adv Biochem Eng Biotechnol.*, 136:65-100 (2013); Kollewe, *American Journal of Biochemistry and Biotechnology*, 9(3): 255-271 (2013); Coco-Martin, Chapter four: A review of therapeutic protein expression by mammalian cells. In BioProcess International. 2008. p. suppl. 28-32; Weber et al., Chapter 6: Insect cell-based recombinant protein production. In: Eibl R., editor Cell and tissue reaction engineering: principles and practice. Berlin Heidelberg: Springer-Verlag; p. 263-273 (2009); Jayaraj et al., *Open Veterinary Science*

*Journal*, Bentham Open; 3:28-34 (2009); Swiech et al., *Protein Expr Purif.*, 84(1):147-53 (2012)). The contents of these documents are herein incorporated by reference. The fusion polypeptide can for instance be produced in the *E. coli* strain Rosetta gami DE3 (Novagen), which is optimized for eukaryotic protein expression, meaning that is equipped with eukaryotic tRNA and able to form disulfide bridges for proper folding of the protein (Novagen competent cells, user protocol TB009 Rev. F 0104). Furthermore the polypeptide can be produced in insect cells, yeast or mammalian cells. Expression in an eukaryotic system, e.g. insect cells, is of advantage since the polypeptide will be glycosylated. The preferred expression is in mammalian cells, such as rat, mouse, hamster or human cells.

An immunogenic composition of the invention preferably further comprises an adjuvant. The weight percent ratio of fusion polypeptide:adjuvant is preferably in the range of fusion polypeptide: adjuvant of 3:1-1:3, preferably about 1:1. A composition or polypeptide according to the invention is formulated in an effective amount, i.e. an amount sufficient to induce an immune response against said fusion polypeptide, preferably the induction of an immune response against said immunogen and a humoral immune response against said self antigen. An immunogenic composition or polypeptide of the invention is preferably administered via administration by vaccination, such as (i) administration by injection, preferably in the form of a liquid such as water or an emulsion, and preferably administered intramuscular or subcutaneous, (ii) transdermal administration, preferably via topical administration, for instance in the form of a cream, jelly, powder, or patch, preferably in combination with an adjuvant; (iii) inhalation, for example in the form of inhalation powders, sprays, suspensions, and the like. An adjuvant can be either co-formulated with the fusion polypeptide or composition of the invention or is in a separate formulation. Administration of the adjuvant may occur via the same or a different route of administration, also depending on the type of adjuvant used. For instance, if GM-CSF is employed as adjuvant, it is preferably administered intravenously or subcutaneously. In general, an adjuvant as described herein is preferably administered through enteral administration or parenteral administration. A composition or polypeptide of the invention is preferably administered intramuscular, subcutaneous or transdermal, e.g. in an aqueous liquid such as a suspension, emulsion or solution in water. Preferably, a composition or (fusion) polypeptide according to the invention is in a pharmaceutically acceptable form adapted for intramuscular, subcutaneous administration.

The invention also relates to a kit of parts comprising (i) a first container for holding a composition or polypeptide of the invention, said container comprising a composition or fusion polypeptide of the invention and (ii) a second container for holding an adjuvant, said second container comprising an adjuvant. It is also envisaged herein that said kit of parts is for use in medicine, more preferably for use in eliciting an immune response in a subject against said self antigen or for use in inhibiting or blocking tumor angiogenesis or tumor growth and/or removing tumor vasculature in a subject. Said kit of parts optionally comprises instructions regarding the administration parameters of said fusion polypeptide, composition and/or adjuvant. The components in the first and second container of the kit of parts are preferably for simultaneous or sequential administration. It is possible to admix the fusion protein and adjuvant, e.g. to obtain an emulsion, prior to intramuscular injection. GM-CSF can be given i.v. prior to intramuscular injection with the fusion protein, or admixed with the fusion protein and then the solution can be injected intramusculary.

A composition or polypeptide according to the invention is preferably for use as a medicament, more preferably for use in eliciting an immune response in a subject against said self antigen, or for use in inhibiting or blocking tumor angiogenesis and/or removing tumor vasculature in a subject. The subject is preferable a dog or human, more preferably a human.

Preferably, when the self antigen as described herein, or the mammalian polypeptide the expression of which is associated with tumor angiogenesis as described herein, is prostate specific membrane antigen (PSMA), the fusion polypeptide is for use in inhibiting, counteracting, blocking, preventing or treating a tumor or cancer in a subject in need of treatment, wherein said tumor or cancer is selected from the group consisting of breast cancer; cervical cancer; colon cancer, more preferably colorectal cancer; endometrial cancer; brain cancer; oral cancer; liver cancer; lung cancer; skin cancer; ovary cancer; pancreatic cancer; renal cancer; stomach cancer; testicular cancer; thyroid cancer and urothelial cancer, more preferably said tumor or cancer is renal cell carcinoma.

Preferably, when the self antigen as described herein, or the mammalian polypeptide the expression of which is associated with tumor angiogenesis as described herein, is laminin, alpha 4 (Lama4) or elastin microfibril interfacer 2 (Emilin2), the fusion polypeptide is for use in inhibiting, counteracting, blocking, preventing or treating a tumor or cancer in a subject in need of treatment, wherein said tumor or cancer is selected from the group consisting of renal cancer, more preferably renal cell carcinoma; colon cancer, more preferably colorectal cancer; liver cancer; lung cancer and breast cancer.

Preferably, when the self antigen as described herein, or mammalian polypeptide the expression of which is associated with tumor angiogenesis as described herein, is fibrillin 2 (Fbn2), the fusion polypeptide is for use in inhibiting, counteracting, blocking, preventing or treating a tumor or cancer in a subject in need of treatment, wherein said tumor or cancer is colon cancer, more preferably colorectal cancer.

Preferably, when the self antigen as described herein, or mammalian polypeptide the expression of which is associated with tumor angiogenesis as described herein, is CD99 antigen (CD99), the fusion polypeptide is for use in inhibiting, counteracting, blocking, preventing or treating a tumor or cancer in a subject in need of treatment, wherein said tumor or cancer is Ewing Sarcoma.

Preferably, when the self antigen as described herein, or mammalian polypeptide the expression of which is associated with tumor angiogenesis as described herein, is versican (Vcan), the fusion polypeptide is for use in inhibiting, counteracting, blocking, preventing or treating a tumor or cancer in a subject in need of treatment, wherein said tumor or cancer is renal cancer, more preferably renal cell carcinoma.

Preferably, when the self antigen as described herein, or mammalian polypeptide the expression of which is associated with tumor angiogenesis as described herein, is CD93 antigen (CD93), the fusion polypeptide is for use in inhibiting, counteracting, blocking, preventing or treating a tumor or cancer in a subject in need of treatment, wherein said tumor or cancer is renal cancer, more preferably renal cell carcinoma, pancreatic cancer, more preferably pancreatic adenocarcinoma (PDAC), and colon cancer, more preferably colorectal cancer.

Preferably, when the self antigen as described herein, or mammalian polypeptide the expression of which is associated with tumor angiogenesis as described herein, is the insulin receptor (Insr), the fusion polypeptide is for use in inhibiting, counteracting, blocking, preventing or treating a tumor or cancer in a subject in need of treatment, wherein said tumor or cancer is preferably a solid tumor, more preferably a cancer preferably selected from colon cancer, colorectal cancer, renal cancer, renal cell carcinoma, stomach cancer, breast cancer, skin cancer and head and neck squamous carcinoma, more preferably renal cell carcinoma, stomach cancer, breast cancer, skin cancer and head and neck squamous carcinoma.

The invention further relates to a method of vaccinating or treating a subject, preferably a subject suffering, or suspected to suffer from, a tumor, comprising the step of administration of a composition or fusion polypeptide of the invention to said subject. Preferably, the vaccination or treatment elicits an immune response in a subject against said self antigen, and/or provides for the inhibition of, or blocking of, tumor growth, tumor angiogenesis and/or provides for the removal of tumor vasculature in a subject.

Preferably, a composition or polypeptide of the invention is assigned as therapy, or administered, when said subject is diseased with e.g. cancer, atherosclerosis, psoriasis, endometriosis or adiposity.

The invention further relates to a use of a composition or fusion polypeptide of the invention for the manufacture of a medicament for eliciting an immune response in a subject against a self antigen, or for inhibiting or blocking tumor growth, tumor angiogenesis and/or for removing tumor vasculature in said human subject. Alternatively, a composition or fusion polypeptide of the invention is for treating and/or preventing diseases subject of therapeutic methods of this invention, including cancer.

The invention further relates to fusion polypeptides. For the purpose of clarity and a concise description, features are described herein and hereinabove as part of the same or separate embodiments, however, it will be appreciated that the scope of the invention may include embodiments having combinations of all or some of the features described. More specifically, the fusion polypeptides as described in the context of immunogenic compositions are as such, i.e. as fusion polypeptides, described herein including any of the limitations as described in this or another section.

The invention further relates to an immunogenic polypeptide comprising a polypeptide moiety comprising a truncated immunogenic region of 45-70 consecutive amino acid residues of the protein of SEQ ID NO:1 or of a protein having at least 90% sequence identity to the protein of SEQ ID NO:1; or
comprising a truncated immunogenic region of 110-150 consecutive amino acid residues of the protein of SEQ ID NO:2 or of a protein having at least 90% sequence identity to the protein of SEQ ID NO:2; or
comprising an immunogenic region of 45-61 consecutive amino acid residues of the protein of SEQ ID NO:3 or of a protein having at least 90% sequence identity to a protein of SEQ ID NO:3, wherein said immunogenic region comprises 12-24% of hydrophilic, bulky amino acid residues selected from the group consisting of histidine, glutamate, arginine, glutamine, aspartic acid and/or lysine.

For reasons of clarity and conciseness of description, features of the foreign antigens as described in the context of immunogenic compositions or fusion polypeptides of the invention, are also expressly envisaged in the context of an immunogenic polypeptide of the invention.

It is noted that an immunogenic polypeptide of the invention may comprise a linker peptide as described herein and/or that the polypeptide moiety has the amino acid sequence of any of SEQ ID NOs: 3, 4, 6 or 7. It is also envisaged herein that the immunogenic polypeptide of the invention has the amino acid sequence of any one of SEQ ID NOs: 3-7.

The self antigens described in aspects of this invention, indicated as the protein products of the genes as listed in Tables 1 and 2, may, in additional aspects, alone, or in combination, also be used as a self antigen in fusion polypeptides as envisaged in aspects and embodiment of this invention wherein the foreign antigen or immunogen is TRX (SEQ ID NO:1) or a protein having at least 90% sequence identity to the protein of SEQ ID NO:1. The term "% sequence identity", in the context of this invention, refers to the percentage of sequence identity over the entire length of the amino acid or nucleotide sequence of the gene, protein or polypeptide. The terms "protein" and "polypeptide" are, unless expressly indicated otherwise in the context of this description, interchangeable herein. The tumor markers or tumor associated antigens as identified herein are suitable targets for therapy, including cancer therapy and therapy of tumor vasculature. Such therapy includes cancer immunotherapy, as well as antisense therapy, including the use of antisense oligonucleotides, siRNAs, or miRNAs against genes indicated in Tables 1 and 2.

The invention further provides a nucleic acid comprising a nucleotide sequence, preferably a DNA sequence that encodes a fusion polypeptide or immunogenic polypeptide of the invention. The person skilled in the art will understand how to generate a DNA sequence that encodes an amino acid sequence of a polypeptide of the invention and how to manufacture and isolate a nucleic acid molecule with said DNA sequence using generally known recombinant DNA techniques. The sequence of the nucleic acid molecule is preferably codon-optimized for protein expression in a host cell of the invention. In this way codons are used that are favored for high-level protein expression in a specific host cell.

The present invention also provides an expression vector comprising a nucleic acid of the invention. Nucleic acid molecules are preferably inserted in an expression vector using recombinant DNA techniques known by the person skilled in the art. Expression vectors in the context of the invention direct the expression of a polypeptide of the invention in a host cell. These expression vectors are preferably replicable in a host cell, either as a plasmid or as part of the chromosomal DNA. Further, the expression vector preferably comprises (i) a strong promoter/enhancer, such as the CMV, SV40 or T7 promoter, (ii) an optimal translation initiation sequence, such as a ribosomal binding site and start codon, preferably a KOZAK consensus sequence and (iii) a transcription termination sequence, including a poly (A) signal when the protein is expressed in eukaryotic cells. Suitable expression vectors include plasmids and viral vectors such as adenoviruses, adeno-associated viruses and retroviruses. The person skilled in the art will understand that the expression vector to be used is dependent on the host cell that is used for expression of a recombinant protein. An expression vector of the invention is preferably suited for insertion of a nucleic acid molecule of the invention into a prokaryotic cell including a bacterial cell, or, more preferred, into a eukaryotic host cell, such as a yeast cell and a mammalian cell. Particularly preferred is the expression vector pET-21a or pCMV4. Further expression vectors compatible with the present invention are TOPO, CMV or pcDNA 3.1.

As an alternative, a nucleic acid molecule of the invention may be inserted into the genome of a host cell. Said insertion preferably is at a locus or within a region that ensures transcription and translation of a nucleic acid molecule of the invention in the host cell.

The invention further provides a host cell comprising a nucleic acid molecule or expression vector according to the invention. The invention preferably provides a host cell carrying a nucleic acid molecule of the invention thereby producing a polypeptide of the invention. Said polypeptide is either produced within the host cell or, preferably secreted from the host cell.

Suitable host cells for use in the present invention include prokaryotic and eukaryotic cells, such as bacterial cells, yeast cells, insect cells, animal cells, mammalian cells; including murine cells, rat cells, sheep cells, simian cells and human cells. Examples of suitable eukaryotic host cells include, but are not limited to HEK 293 cells, the hamster cell line CHO and BHK-21; the murine host cells NIH3T3, NSO and C127; the simian host cells COS and Vero; and the human host cells HeLa, PER.C6, U-937 and Hep G2. Suitable cells are available from public sources such as ATCC and Life Technologies. A number of transfection techniques are known in the art, see, e.g., Graham et al., 1973. Virology 52: 456; Green et at, 2012. "Molecular Cloning: A Laboratory Manual", CSHL Press; Davis et at, "Basic Methods in Molecular Biology", 1986, Elsevier; and Chu et al., 1981. Gene 13: 197. The person skilled in the art preferably employs techniques as described in these references to introduce one or more exogenous nucleic acid molecules into suitable host cells.

Method of Typing of the Invention

The invention further relates to a method of typing a subject for a tumor angiogenesis status, comprising the steps of a) measuring a gene expression level of at least one gene expression product in a sample of a subject comprising, or suspected to comprise, tumor cells, preferably tumor endothelial cells; wherein said at least one gene expression product is selected from the group formed by tissue inhibitor of metalloproteinase 1 (Timp1), apelin (Apln), serum amyloid A3 (Saa3), CD93 antigen (Cd93), heart development protein with EGF-like domains 1 (Heg1), Notch 4, apelin receptor (Aplnr), nestin (Nes), tenascin C (Tnc), pentraxin related gene (Ptx3), vimentin (Vim), tumor necrosis factor alpha induced protein 6 (Tnfaip6), carboxypeptidase Z (Cpz), snail family zinc finger 1 (Snai1), premelanosome protein (Pmel), arylsulfatase I (Arsi), WNT1 inducible signaling pathway protein 1 (Wisp1), glutathione peroxidase 7 (Gpx7), a disintegrin-like and metallopeptidase (reprolysin type) with thrombospondin type 1 motif, 4 (Adamts4), endothelial cell-specific molecule 1 (Esm1), integrin alpha 5 (fibronectin receptor alpha) (Itga5), a disintegrin-like and metallopeptidase (reprolysin type) with thrombospondin type 1 motif, 2 (Adamts2), thrombospondin 2 (Thbs2), matrix metallopeptidase 14 (membrane-inserted) (Mmp14), insulin-like growth factor binding protein 3 (Igfbp3), thrombospondin 1 (Thbs1), fibrillin 1 (Fbn1), periostin, osteoblast specific factor (Poste), leucine rich repeat containing 17 (Lrrc17), fibrillin 2 (Fbn2), cerebral endothelial cell adhesion molecule (Cercam), secreted frizzled-related protein 4 (Sfrp4), C1q and tumor necrosis factor related protein 6 (C1qtnf6), lysyl oxidase-like 3 (Loxl3), immunoglobulin superfamily, member 10 (Igsf10), secreted frizzled-related protein 2 (Sfrp2), FK506 binding protein 10 (Fkbp10), glutamine fructose-6-phosphate transaminase 2 (Gfpt2), carboxypeptidase X 1 (Cpxm1), microfibrillar associated protein 5 (Mfap5), epidermal growth factor-containing fibulin-like extracellular matrix protein 2 (Efemp2), nephroblastoma overexpressed gene (Nov), versican (Vcan), elastin (Eln), cysteine rich protein 61 (Cyr61), sulfatase 1 (Sulf1), nidogen 2 (Nid2), CD248 antigen, endosialin (Cd248), lysyl oxidase-like 2 (Loxl2), follistatin-like 1 (Fstl1), sushi, von Willebrand factor type A, EGF and pentraxin domain containing 1 (Svep1), laminin, alpha 4 (Lama4), slit homolog 3 (Slit3), mannose receptor, C type 2 (Mrc2), cytoskeleton-associated protein 4 (Ckap4), G protein-coupled receptor 133 (Gpr133), fascin homolog 1, actin bundling protein (Fscn1), elastin microfibril interfacer 2 (Emilin2), scavenger receptor class A, member 3 (Scara3), serine (or cysteine) peptidase inhibitor, clade B, member 2 (Serpinb2), chemokine (C—C motif) ligand 2 (Ccl2), insulin receptor (Insr), folate hydrolase 1 (Folh1), CD99 antigen (CD99), casein kappa (Csn3), calcitonin receptor-like (Calcrl), activin A receptor, type II-like 1 (Acvrl1), colony stimulating factor 3 receptor (Csf3r), chloride channel calcium activated 2 (Clca2), C-type lectin domain family 14, member a (Clec14a), transmembrane protein 100 (Tmem100), cysteine and tyrosine-rich protein 1 (Cyyr1), alkaline ceramidase 2 (Acer2), trichorhinophalangeal syndrome I (Trps1), ArfGAP with RhoGAP domain, ankyrin repeat and PH domain 3 (Arap3), integrin alpha 8 (Itga8), sema domain, immunoglobulin domain (10, short basic domain, secreted, (semaphorin) 3G (Sema3g), transmembrane protein 2 (Tmem2), tumor necrosis factor (ligand) superfamily, member 10 (Tnfsf10), HOP homeobox (Hopx), lactalbumin, alpha (Lalba), phosphatidylinositol-3,4,5-trisphosphate-dependent Rac exchange factor 2 (Prex2), mucin 15 (Muc15), rhotekin 2 (Rtkn2), SRY (sex determining region Y)-box 4 (Sox4), tetraspanin 18 (Tspan18), G protein-coupled receptor 126 (Gpr126), C-type lectin domain family 1, member a (Clec1a), extra domain-B of fibronectin (ED-B) and hairy/enhancer-of-split related with YRPW motif 1 (Hey1) as indicated in Tables 1 and 2; b) comparing said gene expression level to a gene expression control value; c) typing said subject for a tumor angiogenesis status on the basis of the difference between said gene expression level and said gene expression control value.

A method of typing of the invention allows identification of (i) subjects in which tumor angiogenesis occurs, or has occurred, or (ii) subjects wherein tumor vasculature is present. The skilled person will appreciate that, with a method of typing of the invention, it is also possible to identify subjects suffering, or suspected to suffer, from a tumor.

Preferably, the gene expression level of at least 1, 2, 3, 4, 5, 6, 7 or 8, 9, 10, 11, 12, 13, 14, 15, 16, 17, 18, 19, 20, or all, gene expression products as referred to in Tables 1 and 2 are measured.

The gene expression level of at least one of the gene expression products listed in Tables 1 and 2 can be determined by any method known in the art. For instance, methods to determine RNA levels of genes are known to a skilled person and include, but are not limited to, northern blotting, quantitative PCR, and microarray analysis.

Northern blotting comprises the quantification of the gene expression product of a specific gene by hybridizing a labeled probe that specifically interacts with said gene expression products, after separation of gene expression product by gel electrophoreses. Quantification of the labeled probe that has interacted with said gene expression product serves as a measure for determining the level of expression. The determined level of expression can be normalized for differences in the total amounts of gene expression products between two separate samples by comparing the level of expression of a gene that is known not to differ in expression level between samples.

Quantitative Polymerase Chain Reaction (qPCR) provides an alternative method to quantify the level of expression of nucleic acids. qPCR can be performed by real-time PCR (rtPCR), in which the amount of product is monitored during the reaction, or by end-point measurements, in which the amount of a final product is determined. As is known to a skilled person, rtPCR can be performed by either the use of a nucleic acid staining agents, such as for example ethidium bromide or SYBR® Green I dye, which interacts with all generated double stranded products resulting in an increase in fluorescence during amplification, or by the use of labeled probes that react specifically with the generated double stranded product of the gene of interest. Alternative detection methods that can be used are dendrimer signal amplification, hybridization signal amplification, and molecular beacons. Different amplification methods, known to a skilled artisan, can be employed for qPCR, including but not limited to PCR, rolling circle amplification, nucleic acid sequence-based amplification, transcription mediated amplification, and linear RNA amplification.

For the simultaneous detection of multiple gene expression products, qPCR methods such as reverse transcriptase-multiplex ligation-dependent amplification (rtMLPA), which accurately quantifies up to 45 transcripts of interest in a one-tube assay (Eldering et al., Nucleic Acids Res 2003; 31: e153) can be employed.

Microarray-based analyses involve the use of selected biomolecules that are immobilized on a surface. A microarray usually comprises nucleic acid molecules, termed probes, which are able to hybridize to gene expression products. The probes are exposed to labeled sample nucleic acid, hybridized, and the abundance of gene expression products in the sample complementary to a probe are determined. The probes on a microarray may comprise DNA sequences, RNA sequences, or copolymer sequences of DNA and RNA. The probes may also comprise DNA and/or RNA analogues such as, for example, nucleotide analogues or peptide nucleic acid molecules (PNA), or combinations thereof. The sequences of the probes may be full or partial fragments of genomic DNA. The sequences may also be in vitro synthesized nucleotide sequences, such as synthetic oligonucleotide sequences.

It is preferred that said gene expression levels of multiple gene expression products are determined simultaneously. Simultaneous analyses can be performed, for example, by multiplex qPCR, RNA sequencing procedures, and microarray analysis. Microarray analyses allow the simultaneous determination of the gene expression levels of a large number of genes, such as more than 50 genes, more than 100 genes, more than 1000 genes, or even more than 10.000 genes, allowing the use of a large number of gene expression data for normalization of the genes comprising the set of gene expression product as indicated in Tables 1 and 2.

In a preferred embodiment, therefore, said gene expression level is determined by microarray analysis.

A probe is specific for a gene expression product or gene as indicated in Tables 1 and 2. A probe is specific when it comprises a continuous stretch of nucleotides that are completely complementary to a nucleotide sequence of a RNA product of said gene, or a cDNA product thereof. A probe can also be specific when it comprises a continuous stretch of nucleotides that are partially complementary to a nucleotide sequence of a RNA product of said gene, or a cDNA product thereof. Partially means that a maximum of 5% from the nucleotides in a continuous stretch of at least 20 nucleotides differs from the corresponding nucleotide sequence of a RNA product of said gene. The term complementary is known in the art and refers to a sequence that is related by base-pairing rules to the sequence that is to be detected. It is preferred that the sequence of the probe is carefully designed to minimize nonspecific hybridization to said probe. It is preferred that the probe is, or mimics, a single stranded nucleic acid molecule. The length of said complementary continuous stretch of nucleotides can vary between 15 bases and several kilo-bases, and is preferably between 20 bases and 1 kilo-bases, more preferred between 40 and 100 bases, and most preferred about 60 nucleotides. A most preferred probe comprises a continuous stretch of 60 nucleotides that are identical to a nucleotide sequence of a RNA product of a gene, or a cDNA product thereof.

To determine a gene expression level of at least one of the genes listed in Tables 1 and 2, the RNA sample is preferably labeled, either directly or indirectly, and contacted with probes on the array under conditions that favor duplex formation between a probe and a complementary molecule in the labeled RNA sample. The amount of label that remains associated with a probe after washing of the microarray can be determined and is used as a measure for the level of RNA of a nucleic acid molecule that is complementary to said probe.

Preferably, the typing in a method of typing of the invention is the typing of said sample of said subject.

It is further preferred that the gene expression control value is obtained by measuring the gene expression level of said at least one gene expression product in a control sample comprising non-tumor endothelial cells of a subject. Preferably, said subject is typed positive for tumor angiogenesis status if the gene expression level of said at least one gene expression product is at least 5 times, preferably at least 20 times, higher than said gene expression control value, or wherein said subject is typed negative for tumor angiogenesis status if the gene expression level of said at least one gene expression product is not at least 5 times higher, preferably not at least 20 times higher, than said gene expression control value.

For the purpose of clarity and a concise description, features are described herein as part of the same or separate aspects and preferred embodiments thereof, however, it will be appreciated that the scope of the invention may include embodiments having combinations of all or some of the features described.

The content of the documents referred to herein is incorporated by reference.

TABLE 1

List of tumor angiogenesis specific markers.

| # | Gene ID mouse | Gene ID human | Gene Name | Gene ID |
|---|---|---|---|---|
| 1 | 21857 | 7076 | Timp1 | tissue inhibitor of metalloproteinase 1 |
| 2 | 30878 | 8862 | Apln | apelin |
| 3 | 20210 | | Saa3 | serum amyloid A3 |
| 4 | 17064 | 22918 | Cd93 | CD93 antigen |
| 5 | 77446 | 57493 | Heg1 | heart development protein with EGF-like domains 1 |
| 6 | 18132 | 4855 | Notch4 | notch 4 [Source: MGI Symbol; Acc: MGI: 107471] |
| 7 | 23796 | 187 | Aplnr | apelin receptor [Source: MGI Symbol; Acc: MGI: 1346086] |
| 8 | 18008 | 10763 | Nes | nestin [Source: MGI Symbol; Acc: MGI: 101784] |
| 9 | 21923 | 3371 | Tnc | tenascin C [Source: MGI Symbol; Acc: MGI: 101922] |
| 10 | 19288 | 5806 | Ptx3 | pentraxin related gene [Source; MGI Symbol; Acc: MGI: 104641] |
| 11 | 22352 | 7431 | Vim | vimentin [Source: MGI Symbol; Acc: MGI: 98932] |
| 12 | 21930 | 7130 | Tnfaip6 | tumor necrosis factor alpha induced protein 6 [Source: MGI Symbol; Acc: MGI: 1195266] |
| 13 | 242939 | 8532 | Cpz | carboxypeptidase Z [Source: MGI Symbol; Acc: MGI: 88487] |
| 14 | 20613 | 6615 | Snai1 | snail family zinc finger 1 |
| 15 | 20431 | 6490 | Pmel | premelanosome protein [Source: MGI Symbol; Acc: MGI: 98301] |
| 16 | 545260 | 340075 | Arsi | arylsulfatase i [Source: MGI Symbol; Acc: MGI: 2670959] |
| 17 | 22402 | 8840 | Wisp1 | WNT1 inducible signaling pathway protein 1 [Source: MGI Symbol; Acc: MGI: 1197008] |
| 18 | 67305 | 2882 | Gpx7 | glutathione peroxidase 7 [Source: MGI Symbol; Acc: MGI: 1914555] |
| 19 | 240913 | 9507 | Adamts4 | a disintegrin-like and merallopeptidase (reprolysin type) with thrombospondin type 1 motif, 4 [Source: MGI Symbol; Acc: MGI: 1339949] |
| 20 | 71690 | 11082 | Esm1 | endothelial cell-specific molecule 1 [Source: MGI Symbol; Acc: MGI: 1918940] |
| 21 | 16402 | 3678 | Itga5 | integrin alpha 5 (fibronectin receptor alpha) [Source: MGI Symbol; Acc: MGI: 96604] |
| 22 | 216725 | 9509 | Adamts2 | a disintegrin-like and metallopeptidase (reprolysin type) with thrombospondin type 1 motif, 2 [Source: MGI Symbol; Acc: MGI: 1347356] |
| 23 | 21826 | 7058 | Thbs2 | thrombospondin 2 [Source: MGI Symbol; Acc: MGI: 98738] |
| 24 | 17387 | 4323 | Mmp14 | matrix metallopeptidase 14 (membrane-inserted) [Source: MGI Symbol; Acc: MGI: 101900] |
| 25 | 16009 | 3486 | Igfbp3 | insulin-like growth factor binding protein 3 [Source: MGI Symbol; Acc: MGI: 96438] |
| 26 | 21825 | 7057 | Thbs1 | thrombospondin 1 [Source: MGI Symbol; Acc: MGI: 98737] |
| 27 | 14118 | 2200 | Fbn1 | fibrillin 1 [Source: MGI Symbol; Acc: MGI: 95489] |
| 28 | 50706 | 10631 | Postn | perlostin, osteoblast specific factor [Source: MGI Symbol; Acc: MGI: 1926321] |
| 29 | 74511 | 10234 | Lrrc17 | leucine rich repeat containing 17 [Source: MGI Symbol; Acc: MGI: 1921761] |
| 30 | 14119 | 2201 | Fbn2 | fibrillin 2 [Source: MGI Symbol; Acc: MGI: 95490] |
| 31 | 99151 | 51148 | Cercam | cerebral endothelial cell adhesion molecule [Source: MGI Symbol; Acc: MGI: 2139134] |
| 32 | 20379 | 6424 | Sfrp4 | secreted frizzled-related protein 4 [Source: MGI Symbol; Ace: MGI: 892010] |
| 33 | 72709 | 114904 | C1qtnf6 | C1q and tumor necrosis factor related protein 6 [Source: MGI Syrnbol; Acc: MGI: 1919959] |
| 34 | 16950 | 84695 | Loxl3 | lysyl oxidase-like 3 [Soume: MGI Symbol; Acc: MGI: 1337004), also known as Loxl2 |
| 35 | 242050 | 285313 | Igsf10 | immunoglobulin superfamily, member 10 [Source: MGI Symbol; Acc: MGI: 1923481] |
| 36 | 20319 | 6423 | Sfrp2 | secreted frizzled-related protein 2 [Source: MGI Symbol; Acc: MGI: 108078] |
| 37 | 14230 | 60681 | Fkbp10 | FK506 binding protein 10 [Source: MGI Symbol; Acc: MGI: 104769] |
| 38 | 14584 | 9945 | Gfpt2 | glutamine fructose-6-phosphate transaminase 2 [Source: MGI Symbol; Acc: MGI: 1338883] |
| 39 | 56264 | 56265 | Cpxm1 | carboxypeptidase X 1 (M14 family) [Source: MGI Symbol; Acc: MGI: 1934569] |
| 40 | 50530 | 8076 | Mfap5 | microfibrillar associated protein 5 [Source: MGI Symbol; Acc: MGI: 1354387] |
| 41 | 58859 | 30008 | Efemp2 | epidermal growth factor-containing fibulin-like extracellular matrix protein 2 [Source MGI Symbol; Acc: MGI: 1891209] |
| 42 | 18133 | 4856 | Nov | nephroblastoma overexpressed gene [Source: MGI Symbol; Acc: MGI: 109185] |
| 43 | 13003 | 1462 | Vcan | versican [Source: MGI Symbol; Acc: MGI: 102889] |
| 44 | 13717 | 2006 | Eln | elastin [Source: MGI Symbol; Acc: MGI: 95317] |
| 45 | 16007 | 3491 | Cyr61 | cysteine rich protein 61 [Source: MGI Symbol; Acc: MGI: 88613] |
| 46 | 240725 | 23213 | Sulf1 | sulfatase 1 [Source: MGI Symbol; Acc: MGI: 2138563] |
| 47 | 18074 | 22795 | Nid2 | nidogen 2 [Source: MGI Symbol; Acc: MGI: 1298229] |
| 48 | 70445 | 57124 | Cd248 | CD248 antigen, endosialin [Source: MGI Symbol; Acc: MGI: 1917695] |
| 49 | 94352 | | Loxl2 | lysyl oxidase-like 2 [Source: MGI Symbol; Acc: MGI: 2137913] |
| 50 | 14314 | 11167 | Fstl1 | follistatin-like 1 [Source: MGI Symbol; Acc: MGI: 102793] |
| 51 | 64817 | 79987 | Svep1 | sushi, von Willebrand factor type A, EGF and pentraxin domain containing 1 [Source: MGI Symbol; Acc: MGI: 1928849] |
| 52 | 16775 | 3910 | Lama4 | laminin, alpha 4 [Source: MGI Symbol; Acc: MGI: 109321] |
| 53 | 20564 | 6586 | Slit3 | slit homolog 3 (*Drosophila*) [Source: MGI Symbol; Acc: MGI: 1315202] |
| 54 | 17534 | 9902 | Mrc2 | mannose receptor, C type 2 [Source: MGI Symbol; Acc: MGI: 107818] |
| 55 | 216197 | 10970 | Ckap4 | cytoskeleton-associated protein 4 [Source: MGI Symbol; Acc: MGI: 2444926] |
| 56 | 243277 | 283383 | Gpr133 | G protein-coupled receptor 133 [Source: MGI Symbol; Acc: MGI: 3041203] |
| 57 | 14086 | 6624 | Fscn1 | fascin homolog 1, actin bundling protein (*Strongylocentrotus purpuratus*) [Source: MGI Symbol; Acc: MGI: 1352745] |
| 58 | 246707 | 84034 | Emilin2 | elastin microfibril interfacer 2 [Source: MGI Symbol; Acc: MGI: 2389136] |
| 59 | 219151 | 51435 | Scara3 | scavenger receptor class A, member 3 [Source: MGI Symbol; Acc: MGI: 2444418] |
| 60 | 18788 | 5055 | Serpinb2 | serine (or cysteine) peptidase inhibitor, clade B, member 2 [Source: MGI Symbol; Acc: MGI: 97609] |
| 61 | 20296 | 6347 | Ccl2 | chemokine (C-C motif) ligand 2 [Source: MGI Symbol; Acc: MGI: 98259] |
| 62 | 16337 | 3643 | Insr | insulin receptor [Source: MGI Symbol; Acc: MGI: 96575]; D630014A15Rik, CD220, IR-B, 4932439J01Rik, IR-A, IR |

TABLE 1-continued

List of tumor angiogenesis specific markers.

| # | Gene ID mouse | Gene ID human | Gene Name | Gene ID |
|---|---|---|---|---|
| 63 | 53320 | 219595 | Folh1 | folate hydrolase 1 [Source: MGI Symbol; Acc: MGI: 1858193]; prostate-specific membrane antigen, glutamate carboxypeptidase II |
| 64 | 673094 | 4267 | CD99 | CD99 antigen |
| 65 | 12994 | 1448 | Csn3 | casein kappa [Source: MGI Symbol; Acc: MGI: 107461] |
| 66 | 54598 | 10203 | Calcrl | calcitonin receptor -like [Source: MGI Symbol; Acc: MGI: 1926944] |
| 67 | 11482 | 94 | Acvrl1 | activin A receptor, type II-like 1 [Source: MGI Symbol; Acc: MGI: 1338946] , ALK1 |
| 68 | 12986 | 1441 | Csf3r | colony stimulating factor 3 receptor (granulocyte) [Source: MGI Symbol; Acc: MGI: 1339755] |
| 69 | 80797 | | Clca2 | chloride channel calcium activated 2 [Source: MGI Symbol; Acc: MGI: 1931471] |
| 70 | 66864 | 161198 | Clec14a | C-type lectin domain family 14, member a [Source: MGI Symbol; Acc: MGI: 1914114] |
| 71 | 67888 | 55273 | Tmem100 | transmembrane protein 100 [Source: MGI Symbol; Acc: MGI: 1915138] |
| 72 | 224405 | 116159 | Cyyr1 | cysteine and tyrosine-rich protein 1 [Source: MGI Symbol; Acc: MGI: 2152187] |
| 73 | 13717 | 2006 | Eln | elastin [Source: MGI Symbol; Acc: MGI: 95317] |
| 74 | 230379 | 340485 | Acer2 | alkaline ceramidase 2 [Source: MGI Symbol; Acc: MGI: 1920932] |
| 75 | 33925 | 7227 | Trps1 | trichorhinophalangeal syndrome I (human) [Source: MGI Symbol; Acc: MGI: 1927616] |
| 76 | 106952 | 64411 | Arap3 | ArfGAP with RhoGAP domain, ankyrin repeat and PH domain 3 [Source: MGI Symbol; Acc: MGI: 2147274] |
| 77 | 241226 | 8516 | Itga3 | integrin alpha 8 [Source: MGI Symbol; Acc: MGI: 109442] |
| 78 | 218877 | 56920 | Sema3g | sema domain, immunoglobulin domain (Ig), short basic domain, secreted (semaphorin) 3G [Source: MGI Symbol; Acc: MGI: 3041242] |
| 79 | 83921 | 23670 | Tmem2 | transmembrane protein 2 [Source: MGI Symbol; Acc: MGI: 1890373] |
| 80 | 22035 | 8743 | Tnfsf10 | tumor necrosis factor (ligand) superfamily, member 10 [Source: MGI Symbol; Acc: MGI: 107414] |
| 81 | 74318 | 84525 | Hopx | HOP homeobox [Source: MGI Symbol; Acc: MGI: 1916782] |
| 82 | 16770 | 3906 | Lalba | lactalbumin, alpha [Source: MGI Symbol; Acc: MGI: 96742] |
| 83 | 109294 | 80243 | Prex2 | phosphatidylinositol-3,4,5-trisphosphate-dependent Rac exchange factor 2 [Source: MGI Symbol; Acc: MGI: 1923385] |
| 84 | 269328 | 143662 | Muc15 | mucin 15 [Source: MGI Symbol; Acc: MGI: 2442110] |
| 85 | 170799 | 219790 | Rtkn2 | rhotekin 2 [Source: MGI Symbol; Acc: MGI: 2158417] |
| 86 | 20677 | 6659 | Sox4 | SRY (sex determining region Y)-box 4 [Source: MGI Symbol; Acc: MGI: 98366] |
| 87 | 241556 | 90139 | Tspan18 | tetraspanin 18 [Source: MGI Symbol; Acc: MGI: 1917136] |
| 88 | 215793 | 57211 | Gpr126 | G protein-coupled receptor 126 [Source: MGI Symbol; Acc: MGI: 1916151] |
| 89 | 243653 | 51267 | Clec1a | C-type lectin domain family 1, member a [Source: MGI Symbol; Acc: MGI: 2444151] |
| 90 | 15213 | 23462 | Hey1 | hairy/enhancer-of-split related with YRPW motif 1 [Source: MGI Symbol; Acc: MGI: 1341800] |

TABLE 2

Tumor angiogenesis specific markers coupled to arRNA/protein Genbank Acc. No.'s

| # | GenBank Acc. No. mRNA/protein Mouse | GenBank Acc. No. mRNA/protein human |
|---|---|---|
| 1 | NM_001044384.1 | NM_003254.2 |
| 2 | NM_013912.3 | NM_017413.4 |
| 3 | NM_011315.3 | S73444.1 |
| 4 | NP_034870.1, NM_010740.3 | NP_036204.2, NM_012072.3 |
| 5 | NP_780465.4, NM_175256.5 | NP_065784.1, NM_020733.1 |
| 6 | NP_035059.2, NM_010929.2 | NP_004548.3, NM_004557.3 |
| 7 | NP_035914.1, NM_011784.3 | NP_005152.1, NM_005161.4, NR_027991.1 |
| 8 | NP_057910.3, NM_016701.3 | NP_006608.1, NM_006617.1 |
| 9 | NP_035737.2, NM_011607.3 | NP_002151.2, NM_002160.3 |
| 10 | NP_033013.3, NM_008987.3 | NP_002843.2, NM_002852.3 |
| 11 | NP_035831.2, NM_011701.4 | NP_003371.2, NM_003380.3 |
| 12 | NP_033424.1, NM_009398.2 | NP_009046.2, NM_007115.3 |
| 13 | NP_694747.2, NM_153107.2 | NP_003643.2, NM_003652.3, NP_001014447.1, NM_001014447.2, NP_001014448.1, NM_001014448.2 |
| 14 | NP_035557.1, NM_011427.2 | NP_005976.2, NM_005985.3 |
| 15 | NP_068682.2, NM_021882.4, XP_006513468.1, XM_006513405.2 | NP_001186983.1, NM_001200054.1, NP_001186982.1, NM_001200053.1 |
| 16 | NP_001033588.1, NM_001038499.1 | NP_001012301.1, NM_001012301.2 |
| 17 | NP_061353.1, NM_018865.2 | NP_001191799.1, NM_001204870.1 |
| 18 | NP_077160.1, NM_024198.3 | NM_015696.4 |
| 19 | NM_172845.2 | NP_005090.3, NM_005099.4 |
| 20 | NP_076101.1, NM_023612.3 | NP_008967.1, NM_007036.4, NP_001129076.1, NM_001135604.1 |
| 21 | NP_034707.3, NM_010577.3 | NP_002196.2, NM_002205.2 |
| 22 | NP_001264234.1, NM_001277305.1, NP_783574.1, NM_175643.3 | NP_067610.1, NM_021599.2, NP_055059.2, NM_014244.4 |
| 23 | NP_035711.2, NM_011581.3 | NP_003238.2, NM_003247.3 |
| 24 | NP_032634.3, NM_008608.3 | NP_004986.1, NM_004995.3 |

TABLE 2-continued

Tumor angiogenesis specific markers coupled to arRNA/protein Genbank Acc. No.'s

| # | GenBank Acc. No. mRNA/protein Mouse | GenBank Acc. No. mRNA/protein human |
|---|---|---|
| 25 | NP_032369.2, NM_008343.2 | NP_001013416.1, NM_001013398.1, NP_000589.2, NM_000598.4 |
| 26 | NP_035710.2, NM_011580.3 | NP_003237.2, NM_003246.2 |
| 27 | NP_032019.2, NM_007993.2 | NP_000129.3, NM_000138.4 |
| 28 | NP_001185695.1, NM_001198766.1 | NP_001273596.1, NM_001286667.1 |
| 29 | NP_083253.1, NM_028977.1 | NP_005815.2, NM_005824.2 |
| 30 | NP_034311.2, NM_010181.2 | NP_001990.2, NM_001999.3 |
| 31 | XP_006498539.1, XM_006498476.2 | XP_011517064.1, XM_011518762.1 |
| 32 | NP_057896.1, NM_016687.3 | NP_003005.2, NM_003014.3 |
| 33 | XP_006521518.1, XM_006521455.2 | XP_011528159.1, XM_011529857.1 |
| 34 | NP_038614.2, NM_01386.4 | NP_001276093.1, NM_001289164.1 |
| 35 | NP_001156356.1, NM_001162884.1 | XP_011511011.1, XM_011512709.1 |
| 36 | XP_006501246.1, XM_006501183.2 | NP_003004.1, NM_003013.2 |
| 37 | NP_038557.1, NM_013529.3 | XP_011523401.1, XM_011525099.1 |
| 38 | NP_038557.1, NM_013529.3 | NP_005101.1, NM_005110.2 |
| 39 | NP_062670.2, NM_019696.2 | NP_001171628.1, NM_001184699.1 |
| 40 | XP_006506427.1, XM_006506364.2 | NP_001284639.1, NM_001297710.1 |
| 41 | XP_006531870.1, XM_006531807.1 | NP_058634.4, NM_016938.4 |
| 42 | NP_035060.1, NM_010930.4 | NP_002505.1, NM_002514.3 |
| 43 | NP_001127947.1, NM_001134475.1 | NP_004376.2, NM_004385.4 |
| 44 | NP_031951.2, NM_007925.3 | NP_001075223.1, NM_001081754.2 |
| 45 | NP_034646.1, NM_010516.2 | NP_001545.2, NM_001554.4 |
| 46 | NP_001185494.1, NM_001198565.1 | NP_055985.2, NM_015170.2 |
| 47 | NP_032721.2, NM_008695.2 | NP_031387.3, NM_007361.3 |
| 48 | NP_473383.1, NM_054042.2 | NP_065137.1, NM_020404.2 |
| 49 | NP_201582.2, NM_033325.2 | |
| 50 | NP_032073.2, NM_008047.5 | NP_009016.1, NM_007085.4 |
| 51 | NP_073725.2, NM_022814.2 | NP_699197.3, NM_153366.3 |
| 52 | NP_034811.2, NM_010681.4 | NP_002281.3, NM_002290.4 |
| 53 | NP_035542.2, NM_011412.3 | NP_003053.1, NM_003062.3 |
| 54 | NP_032652.3, NM_008626.3 | NP_006030.2, NM_006039.4 |
| 55 | NP_780660.1, NM_175451.1 | NP_006816.2, NM_006825.3 |
| 56 | NP_001074811.1, NM_001081342.1 | NP_942122.2, NM_198827.3 |
| 57 | NP_032010.2, NM_007984.2 | NP_003079.1, NM_003088.3 |
| 58 | NP_660140.1, NM_145158.3 | NP_114437.2, NM_032048.2 |
| 59 | NP_766192.1, NM_172604.3 | NP_878185.1, NM_182826.1 |
| 60 | XP_011246244.1, XM_011247942.1 | NP_001137290.1, NM_001143818.1 |
| 61 | NP_035463.1, NM_011333.3 | NP_002973.1, NM_002982.3 |
| 62 | NP_034698.2, NM_010568.2 | NP_001073285.1, NM_001079817.1 |
| 63 | NP_001153178.1, NM_001159706.1 | NP_710163.1, NM_153696.2 |
| 64 | NP_079860.2, NM_025584.2 | NP_001264639.1, NM_001277710.1 |
| 65 | NP_031812.2, NM_007786.4 | NP_005203.2, NM_005212.2 |
| 66 | NP_061252.2, NM_018782.2 | NP_001258680.1, NM_001271751.1 |
| 67 | NP_001264188.1, NM_001277259.1 | NP_000011.2, NM_000020.2 |
| 68 | NP_031808.2, NM_007782.3 | NP_758519.1, NM_172313.2 |
| 69 | NP_085104.1, NM_030601.3 | |
| 70 | NP_080085.3, NM_025809.5 | NP_778230.1, NM_175060.2 |
| 71 | NP_080709.1, NM_026433.2 | NP_001093110.1, NM_001099640.1 |
| 72 | NP_659102.1, NM_144853.3 | NP_443186.1, NM_052954.2 |
| 73 | NP_031951.2, NM_007925.3 | NP_001075223.1, NM_001081754.2 |
| 74 | NP_001277472.1, NM_001290543.1 | NP_001010887.2, NM_001010887.2 |
| 75 | NP_114389.2, NM_032000.2 | NP_054831.2, NM_014112.4 |
| 76 | NP_001192265.1, NM_001205336.1 | NP_071926.4, NM_022481.5 |
| 77 | NP_001001309.1, NM_001001309.2 | NP_001278423.1, NM_001291494.1 |
| 78 | NP_001020550.1, NM_001025379.1 | NP_064548.1, NM_020163.1 |
| 79 | NP_001028931.1, NM_001033759.2 | NP_001129292.1, NM_001135820.1 |
| 80 | NP_033451.1, NM_009425.2 | NP_001177871.1, NM_001190942.1 |
| 81 | NP_783199.1, NM_175606.3 | NP_001138932.1, NM_001145460.1 |
| 82 | NP_034809.1, NM_010679.1 | NP_002280.1, NM_002289.2 |
| 83 | NP_083801.1, NM_029525.1 | NP_079146.2, NM_024870.2 |
| 84 | NP_766567.1, NM_172979.3 | NP_001128564.1, NM_001135092.1 |
| 85 | NP_001074815.1, NM_001081346.1 | NP_660350.2, NM_145307.3 |
| 86 | NP_033264.2, NM_009238.2 | NP_003098.1, NM_003107.2 |
| 87 | NP_899003.1, NM_183180.2 | NP_570139.3, NM_130783.4 |
| 88 | NP_001002268.1, NM_001002268.3 | NP_065188.4, NM_020455.5 |
| 89 | NP_780735.2, NM_175526.3 | NP_001284678.1, NM_001297749.1 |
| 90 | NP_034553.2, NM_010423.2 | NP_036390.3, NM_012258.3 |

SEQUENCE LISTING
(Thioredoxin-1, E. coli K12, UniProtKB Acc. No.:
P0AA25, last modified: Jan. 23, 2007-v2)
SEQ ID NO: 1
msdkiihltd dsfdtdvlka dgailvdfwa ewcgpckmia pildeiadey qgkltvakln idqnpgtapk ygirgiptll lfkngevaat kvgalskgql kefldanla (Type-1 fimbrial protein, A chain, E. coli K12,
UniProtKB Acc. No.: P04128)
SEQ ID NO: 2
mkiktlaivv lsalslssta alaaattvng gtvhfkgevv naacavdags vdqtvqlgqv rtaslaqega tssavgfniq lndcdtnvas kaavaflgta idaghtnvla lqssaagsat nvgvqildrt gaaltldgat fssettlnng tntipfgary fatgaatpga anadatfkvq yq (Unknown Scrambled Protein)
SEQ ID NO: 3
mdnnslsqev qngsnhlenn qsqsngggsd salslsskta alaaattvnd gsdgatssav g (Thioredoxin-1 truncated)
SEQ ID NO: 4
gkltvaklni dqnpgtapky girgiptlll fkngevaatk vgalskgqlk efldanla (M-Thioredoxin-1 truncated + GS linker + His-tag)
SEQ ID NO: 5
mgkltvakln idqnpgtapk ygirgiptll lfkngevaat kvgalskgql kefldanlag sgsgsgshhh hhh (Type-1 fimbrial protein truncated)
SEQ ID NO: 6
aattvnggtv hfkgevvnaa cavdagsvdq tvqlgqvrta slaqegatss avgfniqlnd cdtnvaskaa vaflgtaida ghtnvlalqs saagsatnvg vqildrtgaa ltldgatfss ettlnngtnt i (Type-1 fimbrial protein truncated variant)
SEQ ID NO: 7
kattvnggtv hfkgevvnaa cavdagsvdq tvqlgqvrta slaqegatss kvgfniqlnd cdtnvaskaa vaflgtkida ghtnvlalqs saagsdtnvg vqildrtgaa ltldgatfss ettlnndtnt i

EXAMPLES

Example 1

Screening Method for Identifying Embryonic-Tumor Angiogenesis Specific Markers Material and Method
Animal Material/Studies Mouse embryos of wild type C57BL/6 were used at embryonic day E11 (n=4) and embryonic day E18 (n=4). Two healthy adult male mice were used for whole transcriptome preparation. Organs (heart, lung, liver, kidney) from two healthy adult female mice were used for isolation of normal endothelial cells (NEC). All animal procedures were approved by the VU University Research Animal ethics committee (DEC, AngL 13-01) (Animal experimentation committee).

B16-F10 melanoma tumors (n=2) were obtained at Uppsala University. There the animal work was approved by Uppsala animal ethics committee and performed according to the United Kingdom Coordinating Committee on Cancer Research (UKCCCR) guidelines for the welfare of animals in experimental neoplasia (Woekman P, Lab Anim 1988). Animals were inoculated subcutaneously in the left flank with $0.5 \times 10^6$ B16-F10 melanoma cells in a total volume of 100 µl in PBS. Tumors were allowed to grow about 21 days, until the maximum allowed size was reached.

Isolation of Endothelial Cells from Fresh (Tumor) Tissue

Endothelial cells were isolated according to previously described protocol (Van Beijnum, Blood 109:7 (2006)). Briefly, tissue was minced with surgical blades and digested for approximately 20 min (B16-F10) and 1 h 50 min (normal healthy organs) with 2 mg/ml collagenase type I (Sigma, C0130), 0.125 U dispase (Life Technologies, Bethesda, Md.), 2% fetal calf/bovine serum (FCS/FBS) (Biowest, Nuaille, France, cat. no. S1810-500), 74 µg/ml actinomycin D (Sigma, 01815), 0.05 mg/ml DNAse (Qiagen, 79254), 5 mM $CaCl_2$ dihydrate (J. T. Baker, Deventer, The Netherlands) in DMEM (cat. no. BE12-604F, Lonza Benelux B.V.) and gentle agitation at 37° C. Digestion time is dependent on the tissue type, with extended digestion time for fatty or normal tissue.

To get a single cell suspension, cells were filtered/strained through a 100 µm nylon filter (BD). For tumor endothelial cell (TEC) isolation, cell suspensions (digests) were spun at 400 g, 5 min, 4° C. and resuspended in DMEM, counted and after centrifugation resuspended in 10% DMSO/90% FCS and snap frozen. Digests were stored in −70° C. until use (FACS sorting). Normal organ digests for NEC isolation were immediately used for fluorescent activated cell sorting (FACS).

Fluorescent Activated Cell Sorting of Tumor Endothelial Cells and Normal Endothelial Cells Frozen single cell suspensions were thawed and resuspended in 2% FCS/DMEM. Cell suspensions were washed in 2% FCS/DMEM followed by a wash in cold 0.1% bovine serum albumin (BSA) (Roche Diagnostics, Mannheim, Germany) in PBS (Braun Melsungen AG, Melsungen, Germany) and resuspension in 0.1% BSA/PBS. Endothelial cells (ECs) were stained with anti-mouse CD31 antibody PE-labeled (553373, BD Pharmingen, dilution 1:50) and anti-mouse CD34 antibody PE labeled (551387, BD Pharmingen, dilution 1:30). The single cell suspension was also stained with the pan-leukocyte marker CD 45 (anti-mouse CD45 antibody APC labeled, 559864, BD Pharmingen, dilution 1:50) to be able to separate the EC population from CD31/CD45 positive macrophages. Subsequently, $CD31^+/CD34^+$ cells were separated by fluorescent activated cell sorting (BD FACSAria). Sorted ECs were immediately resuspended in Trizol (15596-026, Life Technologies) and stored at −70° C. until use/further processing.

Isolation of the Whole Transcriptome—RNA Isolation

For each time point (embryonic day) 4 embryos were used for isolation of the whole transcriptome; two embryos per pregnant female mouse. This was done to exclude inter-individual variation. Embryos (E11, E18) were decapitated and snap frozen in liquid nitrogen. Adult male mice (n=2) were cervically dislocated and cut into pieces and directly snap frozen in liquid nitrogen. Mice were further pulverized with an ice-cold hammer in an ice-cold stainless steel lid filled with liquid nitrogen. Small pieces were immediately put into Trizol, in total ca. 100 ml per mouse. Embryos and adult mouse samples were homogenized (homogenizer, handled rotor-stator homogenizer, TissueRuptor (Qiagen)) to optimize RNA isolation. All RNA was isolated according to the Trizol reagent protocol provided by Life Technologies. Small amounts of RNA were co-precipitated with glycogen (361505, Calbiochem) to increase RNA yield. The RNA quality was determined with a Bioanalyzer (Agilent Technologies).

RNA Sequencing

A polyA selection was performed to select for stable mRNA and get rid of small microRNAs, tRNA and bacterial or other prokaryotic RNA. For each sample a sequencing library was prepared with 50 base paired end reads (Illumina TruSeq Sample Prep protocol) to enable detection of alternative splicing. Samples were sequenced on an Illumina HiSeq 2000 (Illumina, San Diego, Calif.) with HCS 2.2.68 software suite (Illumina). RNA sequencing experiments and analysis of the data was performed by the genomics core facility at the Netherlands Cancer Institute. The obtained reads (50 million 50 bp paired end reads per sample) were mapped to the mouse reference genome (GRCm38). Genome mapping and differential expression analysis was performed with Cufflinks software (C Trapnell, Nat Biotechnol 2010; A Roberts, Genome Biology 2011; A Roberts, Bioinformatics 2011; C Trapnell, Nat Biotechnol 2012). For detection of splice variants the reads were mapped to the whole mouse genome, including exon and intron DNA. 30 reads per gene were chosen as cut off value to be able to be certain of true expression. Differential gene expression was assumed if there was at least a log 2 fold change in expression level between the embryos and tumor endothelial cells compared to the adult mouse/NEC. To narrow down the number of detected target genes in the tumor endothelial cells, genes 100× upregulated (log 7 fold) in tumor endothelial were chosen. This was also done to correct for that endothelial cells comprise only about 1% of the body's total cell population.

Target Validation by Real-Time Quantitative PCR

From each RNA-sample cDNA was synthesized with the iScript cDNA kit (Bio-Rad). The amount of cDNA present in the sample was determined by SYBR green assays. Approximately 10 ng cDNA template was used per reaction, 1×SYBR Green Master Mix (BioRad Laboratories) and 5 µM of each primer (Eurogentec, Seraing, Belgium) (Table 1). Primers were validated to be able to have a range of Ct values within which the expression can be considered reliable. We also used melting curves of the primers to be able to distinguish between primer dimer formation and amplicon/amplification signal.

Samples were run in triplicate and analyzed on the CFX9G Real Time System C1000 Thermal Cycler (BioRad Laboratories). Data were analyzed with CFX Manager software (BioRad Laboratories), and further processed in MS Excel. All samples were normalized to cyclophillin A, beta-actin and beta-2 microglobulin transcript expression to account for variations in template input (Thijssen V L, Exp Cell Res 2004).

Results

Whole Transcriptomes from Different Mouse Tissues were Isolated Successfully

The whole transcriptome was isolated from mouse embryos E11 (n=4), E18 (n=4), adult male mice (n=2) and normal healthy organs (n=2) and tumor endothelial cells, derived from B16-F10 melanoma (n=2). The purity of the tumor endothelial cells isolated by FACS sorting was about 90% (TEC1 89.8%; TEC2 86.7%) Isolated TEC RNA was of sufficient good quality ($RIN_{TEC1}$ 8.20; $RIN_{TEC2}$ 6.80) for RNA sequencing. Since digestion of normal tissue was difficult, digested samples of healthy organs were pooled for NEC isolation. We could obtain an amount of RNA for RNA sequencing of good quality. The RNA Integrity Number (RIN) was above 8 for all eight embryos and the two healthy adult samples (Table 2).

TABLE 2

RIN values embryo and adult samples

| Sample ID | RIN value |
|---|---|
| E11 mouse 1 embryo 8 | 9.60 |
| E11 mouse 1 embryo 9 | 9.90 |
| E11 mouse 2 embryo 2 | 9.40 |
| E11 mouse 2 embryo 3 | 9.60 |
| E18 mouse 1 embryo 1 | 9.60 |
| E18 mouse 1 embryo 2 | 9.60 |
| E18 mouse 2 embryo 1 | 9.50 |
| E18 mouse 2 embryo 2 | 9.40 |
| Adult mouse 1 | 8.00 |
| Adult mouse 2 | 8.30 |

Embryonic Genes are Re-Used in Tumor Angiogenesis

RNA samples were sequenced with Illumina HiSeq 2000 equipment and a total number of 25077 genes were found to be log FC≥2 (p<0.05) downregulated in the adult mouse. The Venn-diagram displays the number of genes found in each category (E11, E18 and TEC compared to the adult mouse) (FIG. 1d). 288 genes are solely expressed in the embryo and TEC overlapping population. Only about 1% of the total cell population in the body is endothelial cells and we have enriched for (tumor) endothelial cells by FACS, so therefore we choose a 100-fold overexpression (p<0.05) in TEC versus adult/NEC as cut-off. This generated a list of 29 potential target genes. Some discrepancy between the number of reads obtained for each gene in the adult versus NEC was observed, but overall a similar expression of the target genes was found in both samples. Meaning that it might not matter if enriched cells and total cells are compared. Since in the NEC sample the EC are also enriched. Therefore a cut-off of 100-fold might not be required, but other genes with a lower-fold overexpression might be interesting target genes as well.

Validation of Tumor Endothelial Specific Target Genes

Figure 8:
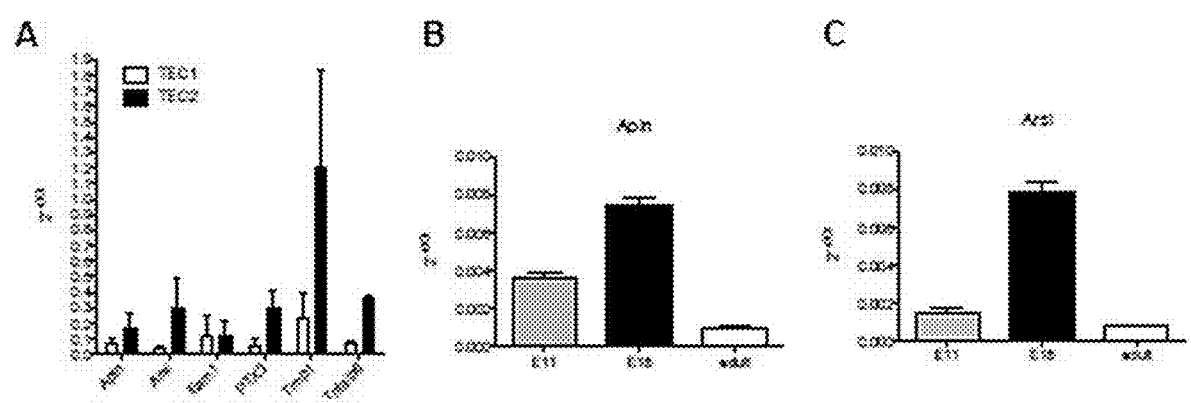
FIG. 8. Target validation by reverse transcription quantitative PCR (RT-qPCR). Expression levels ($2^{-\Delta ct}$) of target genes in different tissues and cell lines. A) Expression of Apln, Arsi, Esm1, PTX3, Timp1 and Tnfaip6 in B16-F10 melanoma derived tumor endothelial cells (TEC). B) Expression of Apln in embryo (E11, E18) and adult mouse. C) Expression of Arsi in embryo (E11, E18) and adult mouse. D) Expression of Esm1 in embryo (E11, E18) and adult mouse. E) Expression of PTX3 in embryo (E11, E18) and adult mouse. F) Expression of Timp1 in embryo (E11, E18) and adult mouse. G) Expression of Tnfaip6 in embryo (E11, E18) and adult mouse. H) Expression of the different by RNA sequencing identified target genes in the B16-F10 melanoma tumor cell line. I) Expression of the different target genes in the Bend5 (primary mouse brain microvascular endothelial cells) endothelial cell line.
Figure 8:
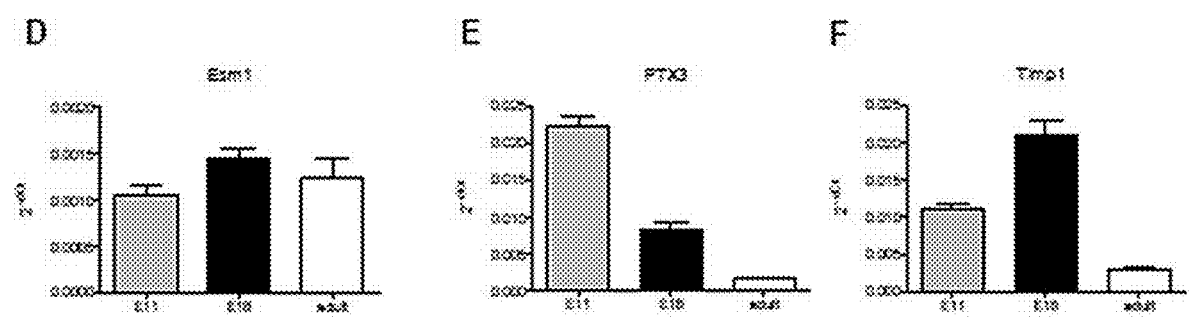
Figure 8:
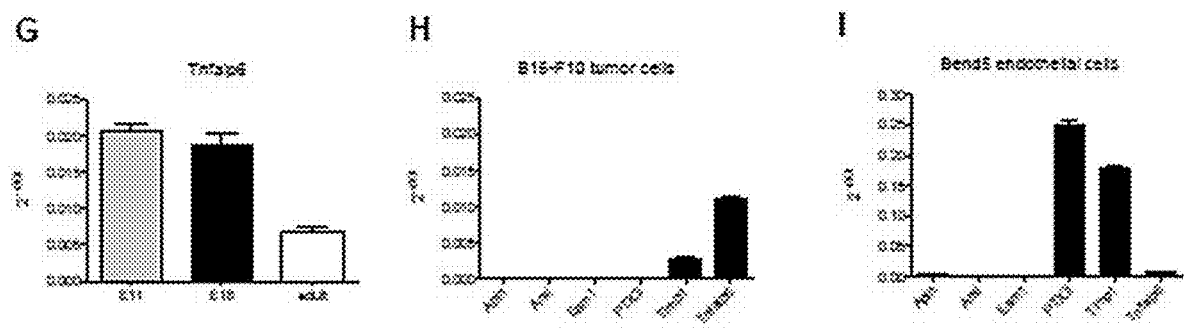

We found several genes known to be involved in angiogenesis. After looking at the cellular localization of the targets, we chose 6 genes to proceed with in validation experiments. Potential interesting targets should either be present in the plasma membrane or secreted to facilitate future drug targeting. We validated the expression of the 6 target genes in the source material (the RNA isolates from embryo, adult mouse and tumor endothelium) by reverse transcription (RT)-qPCR (quantitative PCR) (FIG. 8). We also validated the expression of the target genes in Bend5 endothelial cells (FIG. 8i) and B16-F10 melanoma cells (FIG. 8h). All genes showed a very low/absent expression in the melanoma tumor cells, indicating that the found genes were specific to (tumor) endothelial cells. For some of the target genes a higher expression level could be detected in Bend5 endothelial cells (FIG. 8i). One might not expect expression of the target genes in normal endothelial cells. However, the Bend5 endothelial cell line is derived from immortalized mouse brain endothelial cells, which makes these cells more tumor endothelial cell-like.

Example 2

Immunogenic Compositions

Material and Method; Fusion Polypeptides Constructs TRX-EDB and TRX

The expression vector pET21a TRX-EDB was constructed as follows.

Briefly, the region encoding the ED-B domain and an N-terminal His-tag (309 bp) was restricted with the endonucleases BamH1 and Xho1 (Thermo Scientific, Waltham, Mass., USA) from the plasmid Hum TS-33-EDB containing the EDB domain between these two restriction sites. A pET-21a vector (Novagen, EMD Chemicals, Gibbstown, N.J., USA) containing the bacterial TRX sequence (354 bp) (A Holmgren, Ann Rev Biochem 1985; acc no. GenBank EDV64981.1; all referenced Genbank accessions referred to herein refer to Genbank as of 31 May 2016) was also restricted with BamH1 and Xho1. Thereafter the EDB insert was ligated in frame into the pET-21a vector, downstream the bacterial TRX sequence. The pET21-TRX vector was a kind gift of Dr. Anna-Karin Olsson (Uppsala University, Uppsala, Sweden).

TRXtr-EDB

The TRX sequence in the pET2 1a TRX-EDB vector was replaced with a PCR-amplified TRXtr sequence (192 bp). The resulting vector construct was named pET21a TRXtr-EDB. Both TRX and TRXtr contain an C-terminal GS-linker sequence.

```
Forward TRXtr primer
'5-TATCATATGGGCAAACTGACCGTTGCAAAACTGA-3'

Reverse TRXtr primer
'3-AGCGGATCCGCTACCAGAACCAGAACCGGCCAG-3'
```

To construct the pET21a-TRXtr plasmid, the TRX-EDB sequence was restricted from the plasmid by Nde1 and Xho1 restriction enzyme (Thermo Scientific) cleavage and replaced by the TXRtr sequence.

TFP-EDB, TFPv-EDB and USP-EDB

The DNA sequences encoding the truncated Type-1 fimbrial protein, A chain (TFPtr; 393 bp), TFPvariant (TFPv; 393 bp) or unspecified protein (USP; 183 bp) were ordered from Genscript (Piscataway, N.J., USA) and inserted in frame upstream the ED-B domain, in the pET21a expression vector.

TRX-Vimentin, TRXtr-Vimentin and Vimentin

The pET21a-TRX-Vimentin plasmid was constructed by restricting the pET21a-TRX-EDB with restriction enzymes BamH1 and Xho1, to remove the EDB sequence. The EDB sequence was then replaced with the mouse vimentin sequence (NCBI Gene ID 22352). For construction of the pET21-TRXtr-Vimentin vector the TRX was removed and replaced by TRXtr. To obtain the pET21a-Vimentin plasmid the mouse vimentin sequence was cut from a pUC57-Vimentin vector (Genscript, Piscataway, N.J., USA) and inserted into a pET2 1a expression vector.

Expression and Purification of the Different Fusion-Proteins

The different vectors were transformed into *Escherichia coli* Rosetta gami (DE3) (Novagen; EMD Chemicals) for expression of the fusion proteins. Rosetta gami (DE3) is an *E. coli* strain optimized for eukaryotic protein expression. Overnight cultures were diluted 1:2 or 1:3 and grown until $OD_{600}$ (optical density) 0.5. Protein expression was induced with 1 mM isopropyl β-D-1-thiogalactopyranoside (IPTG) (Invitrogen, Life Technologies, CA, USA) for 4 hours at 37° C. For the recombinant proteins TRXtr, TRXtr-EDB, TFP-EDB and TFPv-EDB bacterial pellets were dissolved in 8M urea/PBS (Acros Organic-Thermo Fisher Scientific, Geel, Belgium). The bacterial pellet of the USP-EDB protein was dissolved in PBS. Proteins were released from the bacterial pellets by sonication on ice for 12 cycles (30 s on and 30 s off) (Soniprep 150 MSE, amplitude 18-26 microns). Bacterial debris was pelleted by centrifugation at 4500 rpm (3584 g) (Hettich Rotina 420R, Geldermalsen, The Netherlands) and the supernatant collected. Thirty milliliters of supernatant (originating from 1 L bacterial culture) was mixed with 2.5 ml Ni-NTA agarose slurry (Qiagen, Hilden, Germany) and incubated "end-over-end" for 3 h at 4° C. The Ni-NTA agarose was pelleted by centrifugation at 4500 rpm, 10 min at 4° C. and washed 5 times with PBS pH 7.0/1M NaCl/ 0.1% Tween-20. To get rid of the Tween-20 (P1379, Sigma-Aldrich, Zwijndrecht, The Netherlands), an additional washing step with PBS was performed before transfer of the Ni-NTA agarose to a 2 ml syringe with a glass filter (Satorius Stedim Biotech GmBH, Göttingen, Germany). The column was washed again with PBS and washed with 4×1250 μl fractions 10 mM imidazole (J. T. Baker, Avantor Performance Materials B.V., Deventer, The netherlands) in 20 mM Tris (pH 8.0)/0.1M NaCl to remove non-specific/background protein binding. Final protein was eluted in four 200 mM imidazole 1250 μl fractions.

Purification of the TRX protein was performed as described above, with the exception that the bacterial pellet was dissolved in 50 ml 5M urea/PBS before sonication. 1 nil Ni-NTA agarose slurry was added to the supernatant (originating from 1 L bacterial culture). During the incubation of the supernatant with Ni-NTA agarose 10 mM imidazole was added, to reduce background. Prior to elution of the TRX protein with 200 mM (4×500 μl fractions) the column was washed with 10×500 μl fractions 20 mM imidazole.

For the production of TRX-EDB, TRX-Vimentin, TRXtr-Vimentin protein and Vimentin, protein expression was induced at 22° C. for 16 h. The lower induction temperature was used to increase the soluble protein fraction. To release the TRX-Vimentin protein or vimentin protein form the bacterial pellet, 1 L pelleted culture was dissolved in 8M urea/PBS and sonicated 15×20 s on and 30 s off on ice (amplitude 22-26 microns). The bacterial debris was pelleted at 4500 rpm, 10 min, 4° C. and the supernatant dialyzed against 4M urea/PBS in Visking dialysis tubing 27/32 (Mw cutoff 12-14000 Da; cat no. 44114, Serva Feinbiochemica GmbH, Heidelberg, Germany) at 4° C. for several hours until a final dialysis step in 0.5M urea/PBS. For purification of the TRXtr-Vimentin protein induced bacterial pellet was dissolved 9.5M urea/30 mM Tris HCl/10 mM methylammonium chloride/2 mM EDTA/2 mM DTT (pH 8.0) and sonicated as described for TRX-Vimentin. The supernatant was stepwise dialyzed to 0.5M urea/PBS in Visking dialysis tubing 27/32 (Mw cutoff 12-14000 Da). For the purification of TRX-EDB thirty milliliters of bacterial supernatant (originating from 1 L bacterial culture) was mixed with 1 ml Ni-NTA agarose slurry. After an incubation step and several washing steps the TRX-EDB protein was eluted with 100 mM imidazole in four 500 μl fractions.

Protein containing fractions of TRX-EDB, TRXtr-EDB, TFP-EDB and TFPv-EDB were pooled and dialyzed against PBS (pH 7.0) in Slide-A-Lyzer dialysis cassette 7 kDa Mw cutoff (Fisher Scientific, Landsmeer, The Netherlands). For dialysis of TRX and TRXtr a snakeskin pleated dialysis tubing with 3.5 kDa Mw cutoff (cat no. 68035, Thermo Scientific) was used. Final protein concentration was estimated by comparison with BSA fraction V (Roche Diagnostics, Mannheim, Germany) standard on SDS-PAGE and by a protein quantification assay (Micro BCA Protein Assay, Pierce Biotechnology, Rockford, Ill., USA). Protein identity was confirmed by Western blot when possible.

Both the EDB protein and TRX-galectin1 (TRX-Gal1, containing mouse galectin1) protein were a kind gift from Dr. Anna-Karin Olsson (Uppsala University, Uppsala, Sweden).

Western Blot

To confirm identity of the TRX-Vimentin, TRXtr-Vimentin and Vimentin protein a SDS-PAGE gradient gel (Mini-Protean TGX gel, Bio-Rad Laboratories, Veenendaal, The Netherlands) was run for 1 h at 100V. Proteins were wet blotted onto Immobilon® PVDF (polyvinylidene) membrane (Merck Millipore, Darmstadt, Germany) for 2.5 h at 100V. The membrane was then blocked with Rockland buffer (Rockland Immunochemicals Inc., Limerick, Pa., USA) for 1 h at room temperature. Vimentin was visualized by incubation of the membrane with anti-vimentin RV202 antibody (sc-32322, Santa-Cruz Biotechnology, Heidelberg, Germany) overnight at 4° C. After several washing steps in PBS/0.1% Tween-20 (P1379, Sigma-Aldrich) the membrane was incubated with donkey anti-mouse IR dye 680 RD (LI-COR Biosciences, Lincoln, Nebr., USA) diluted 1:10 000 for 1 h at room temperature. Then the membrane was washed again and imaged with an Odyssey (LI-COR Biosciences).

Vaccine Preparation

For vaccine preparation the fusion proteins were mixed 50:50 with either Freund's complete adjuvant (F5881, Sigma-Aldrich), for primer vaccinations, or with Freund's incomplete adjuvant (F5506, Sigma-Aldrich), for booster vaccinations. The amount of protein administered/injected was determined by the size/Mw of the protein (Tables 3 and 4).

TABLE 3

Amount of fusion protein used for vaccination against EDB.

| Protein | Size (kDa) | Amount used for vaccination (μg/mouse) |
|---|---|---|
| TRX | 13.0 | 50 |
| TRX-EDB | 20 | 100 |
| TRXtr-EDB | 17.5 | 75 |
| TFP-EDB | 23.9 | 100 |
| TFPv-EDB | 24.1 | 100 |
| USP-EDB | 16.8 | 75 |

TABLE 4

Amount of fusion protein used for vaccination against Vimentin.

| Protein | Size (kDa) | Amount used for vaccination (μg/mouse) |
|---|---|---|
| TRX | 13.0 | 20 |
| TRXtr | 7.6 | 10 |
| TRX-Vimentin | 67.0 | 100 |
| TRXtr-Vimentin | 61.0 | 90 |

Cell Culture

T241 fibrosarcoma cells and B16-F10 melanoma cells (American Type Culture Collection, Manassas, Va., USA) were cultured in Dulbecco's modified eagle medium (DMEM) (cat. no. BE12-604F, Lonza Benelux B.V., Breda, The Netherlands)+2 mM L-glutamine (cat no. 17-605C, Lonza Benelux B.V.)+100 U/ml penicillin/streptomycin (cat. no. DE17-602E Lonza Benelux B.V.) supplemented with 10% Fetal calf serum (FCS) (cat. no. S1810-500, Biowest, Nuaille, France). CT26 colon carcinoma cells (American Type Culture Collection) were cultured in Roswell Park Memorial Institute (RPMI) 1640 supplemented with 10% FCS.

Animal Experiments

All animal experiments were approved by local ethics board of the VU University Medical Center (reg. no. AngL 13-02; AngL 14-01) and were performed in accordance with the Dutch guidelines and law on animal experimentation.

Approximately 8-weeks old female C57BL/6 or BALB/c mice (n=5 per group) were vaccinated 4 times in 2-weeks intervals with 50 μl vaccine in each groin (total injection volume 100 μl). One week after each vaccination approximately 50 μl blood was drawn from the tail vein after warming the mice under a red (heating) lamp for 5 min. Antibody levels in the sera of the mice were measured by ELISA. Two weeks after the $4^{th}$ vaccination C57BL/6 mice were inoculated in their right flank with $0.5 \times 10^6$ T241 fibrosarcoma cells; a syngeneic mouse tumor cell line expressing EDB or $0.1 \times 10^6$ B16-F10 melanoma cells. BALM mice were inoculated in their right flank with $0.2 \times 10^6$ CT26 colon carcinoma cells. Tumor volume was measured with a caliper and calculated according to the formula width$^2 \times$length$\times \pi/6$. Mice were sacrificed about 2-3 weeks after tumor cell inoculation. Two independent studies were performed with 5 mice per group. Half the tumor was cryopreserved and the other half was paraffin embedded. Normal organs were cryopreserved. Tissue was stored at −80° C. until further use.

Anti-EDB Antibody and Anti-Vimentin Antibody ELISA

Antibodies against EDB were measured in the sera of vaccinated mice by coating the ELISA plate (Nunc, Maxisorp, cat. no. 44-2404-21, Thermo Fisher Scientific, Waltham, Mass., USA) with 8 μg/ml recombinant EDB protein for 1 h at 37° C. For detection of anti-vimentin antibodies plates were coated with 4 μg/ml recombinant vimentin diluted in 0.5M urea (Acros Organics, Geel, Belgium). Consecutively, plates were blocked with 100% horse serum in PBS (H1138, Sigma-Aldrich, Zwijndrecht, The Netherlands) for 1 h at 37° C. After the blocking step the plate was washed for 5 min in PBS. Mouse serum was diluted 10% horse serum/PBS before further dilution in 10% Rosetta Gami protein extract/PBS, to prevent unspecific binding, to a final dilution of 1:150. For the serial dilution the following dilutions were made 1:100, 1:300, 1:900, 1:2700, 1:8100 and 1:24300. The serum was incubated for 45 min at 37° C. and plates were washed 4 times with PBS for 1 min, 5 min, 1 min and 5 min to remove the excess of antibody. For detection plates were incubated with a biotinylated goat anti-mouse antibody (cat. no. E0433, DAKO, Heverlee, Belgium,), diluted 1:2000 in PBS-T 0.01%, 45 min at 37° C., followed by a washing step as previously described and incubation with streptavidin-horseradish peroxidase (cat. no. P0397, DAKO, Heverlee, Belgium), dilution 1:2000 (concentration 0.4 μg/ml) in 0.01% PBS-T, 30 min at 37° C. After a final washing step plates were developed with TMB (T8665, Sigma-Aldrich, Zwijndrecht, The Netherlands) and absorbance was read at 655 nm with a BioTek, Synergy HT microplate reader (BioTek, Bad Friedrichshall, Germany).

Anti-TRX Antibody ELISA

TRX-Gal1 protein (a kind gift from Dr. AK Olsson, Uppsala University, Sweden) was used for this ELISA. Plates were coated with 8 μg/ml TRX-Gal1 and either assayed at serum dilution of 1:1000 or a dilution series (1:1000, 1:3000, 1:9000, 1:27000, 1:81000) was made. Mouse sera were diluted 1:10 in horse serum and further diluted in 10% Rosetta gami extract/PBS.

Results

Figure 1:
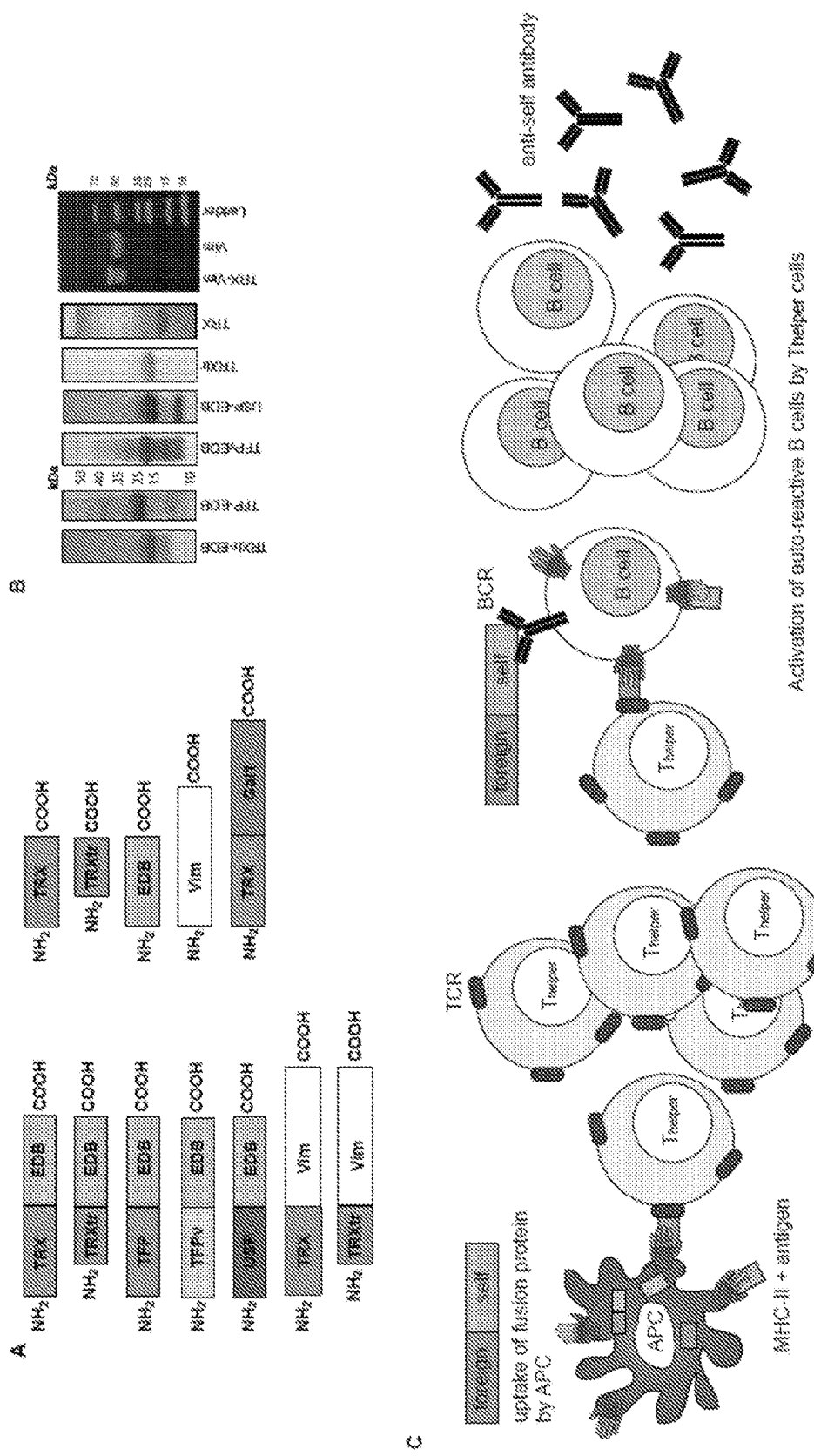
FIG. 1 shows different fusion protein constructs and the vaccination mechanism. Panel A displays the different fusion protein constructs that were developed. The fusion proteins TRX-EDB (20 kDa), TRXtr (uncated)-EDB (17.5 kDa), TFP (type-I fimbrial protein)-EDB (23.9 kDa), TFPv (type-I fimbrial protein variant)-EDB (24.1 kDa), USP (unspecified protein)-EDB (16.8 kDa), TRX-Vim (mouse vimentin) (67 kDa) and TRXtr-Vim (61 kDa) were used for vaccination. The TRX protein (13.2 kDa) and TRXtr protein (7.6 kDa) were used for vaccination of control mice. The EDB protein (10.9 kDa), mouse vimentin (Vim) protein (54 kDa) and TRX-Gal1 (mouse galectin-1) (28 kDa) were used for detection of antibodies in ELISA. Panel B shows the appearance of the proteins used on SDS-PAGE or western blot after purification. TRXtr appears at ~15 kDa, which is about twice its expected size, probably due to dimerization. C) After injection of the fusion protein in combination with a potent adjuvant, antigen-presenting cells (APC) take up the fusion protein and present foreign (non-self) peptides and self-peptides (EDB) on MHC class II. Only the foreign peptides will be recognized by the T-cell receptor (TCR) on T-helper cells (T-helper) and cause T-cell activation. Self-peptides are not seen, since auto-reactive T cells are deleted in the thymus during development. On the other hand auto-reactive B cells are present in the circulation. Those will recognize the self-part (EDB) of the fusion protein via their B-cell receptor (BCR). The auto-reactive B cells will internalize the fusion protein and also present foreign- and self-peptides via MHC class II. Now the previously activated T-helper cells will activate these auto-reactive B cells, since they present the same foreign peptides. The activated auto-reactive B cells then undergo clonal expansion and produce anti-EDB antibodies.
Figure 1:
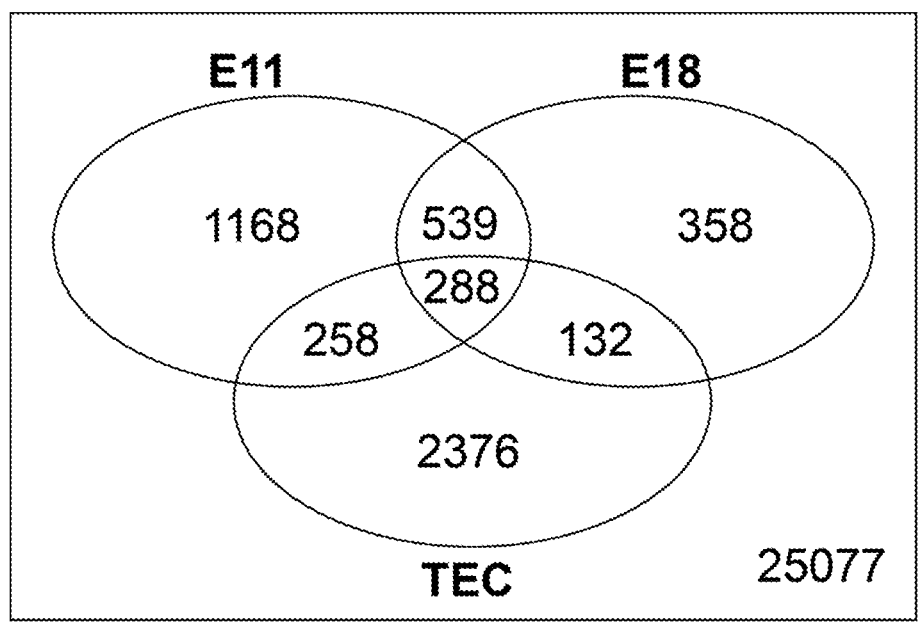

In order to investigate if the immune response against a self-antigen can be improved by shortening the foreign fusion partner/reducing the size of the fusion partner we designed a truncated form of the bacterial protein thioredoxin, named TRXtrunc (SEQ ID NO:4) (TRXtr). The TRXtr protein consists of only half the TRX sequence ($TRX_{51-108}$), a GS linker and a C-terminal His-tag. Furthermore, we choose another bacterial protein type-1 fimbrial protein (TFP) (SEQ ID NO:6). In addition we developed a variant of said TFP (SEQ ID NO:7). Together with the protein expert Dr. Kevin Mayo we also designed an artificial protein consisting of several predicted highly soluble peptide stretches derived from different bacterial proteins. This newly build protein we called unspecified protein (USP) (SEQ ID NO:3). All DNA sequences of the foreign proteins were cloned in frame N-terminal of the DNA sequence of the self-antigen EDB. EDB was used as the fusion partner to be able to compare the effect of the different fusion proteins on antibody production against EDB and the anti-tumor response with the 'golden standard'/previously used TRX-EDB fusion protein. A schematic representation of the constructs used in this study is shown in FIG. 1A. The protein TRX-Gal1 was used for detection of TRX antibodies and the EDB-protein for detection of antibodies towards the self-antigen EDB in ELISA. SDS-PAGE protein gels show that all the proteins could be produced reasonably pure (FIG. 1b).

Self-Antibody Levels/Titers Depend on the Fusion Partner

Figure 2:
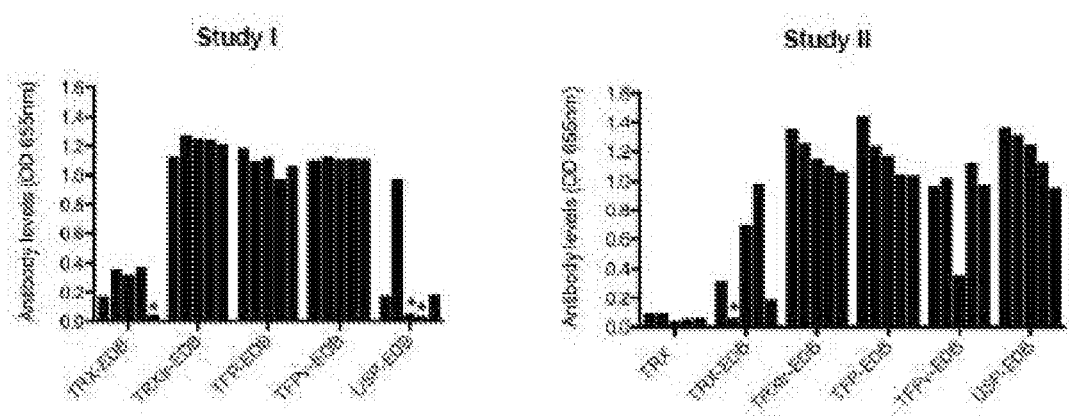
FIG. 2 shows anti-EDB antibody levels in wild type C57BL/6 mice vaccinated with the indicated fusion proteins. From FIG. 2, it follows that the fusion proteins of the invention elicit increased antibody titer levels against the self-antigen EDB as compared to the TRX-EDB fusion protein known from the art.
Figure 3:
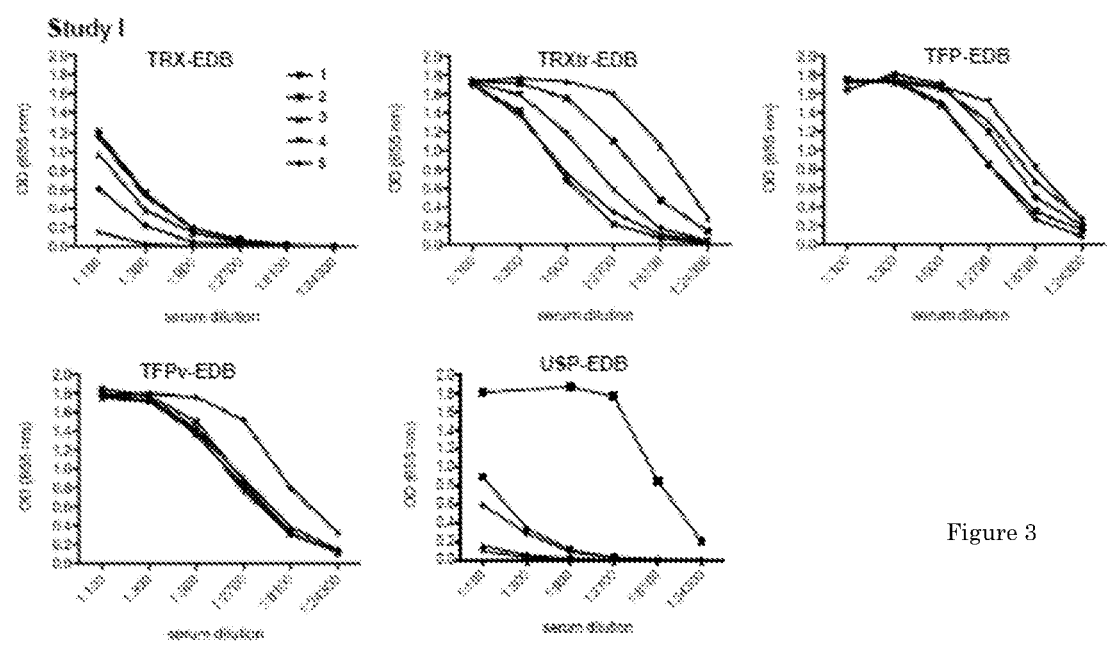
FIG. 3 shows anti-EDB antibody titers per individual mouse for each treatment group in two individual studies. Serum was diluted 1:100-1:24300 and optical density measured at 655 nm.
Figure 3:
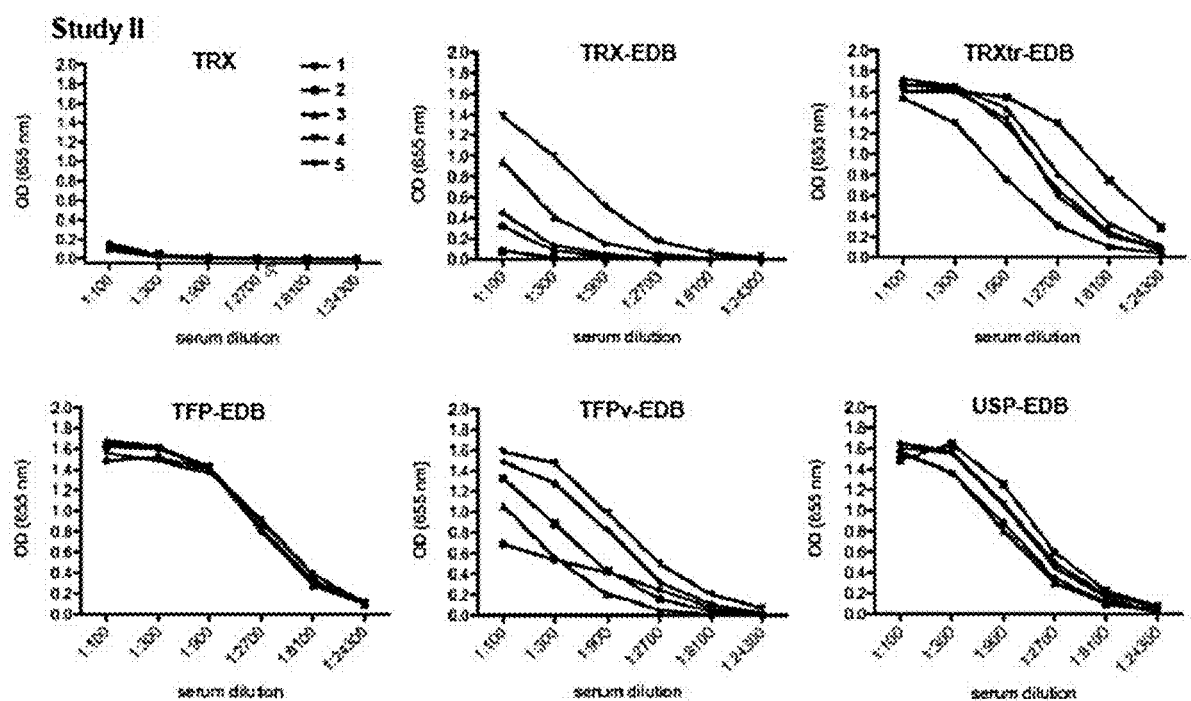
Figure 4:
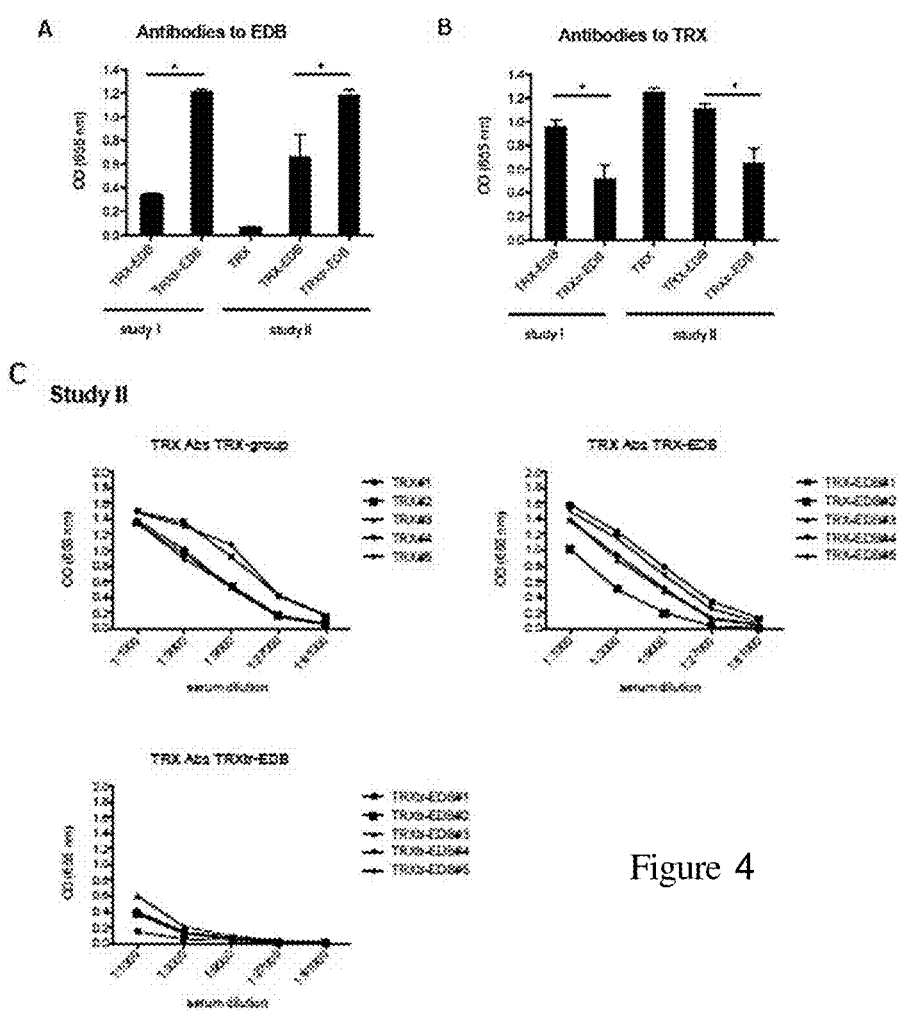
FIG. 4, panels A and B, shows that anti-EDB antibody levels are increased upon truncation of TRX, whereas panel B shows that antibodies to TRX are reduced when TRX is truncated. Panel C shows antibody titers against TRX in C57BL/6 mice vaccinated with TRX, TRX-EDB or TRXtr-EDB (study II).
Figure 5:
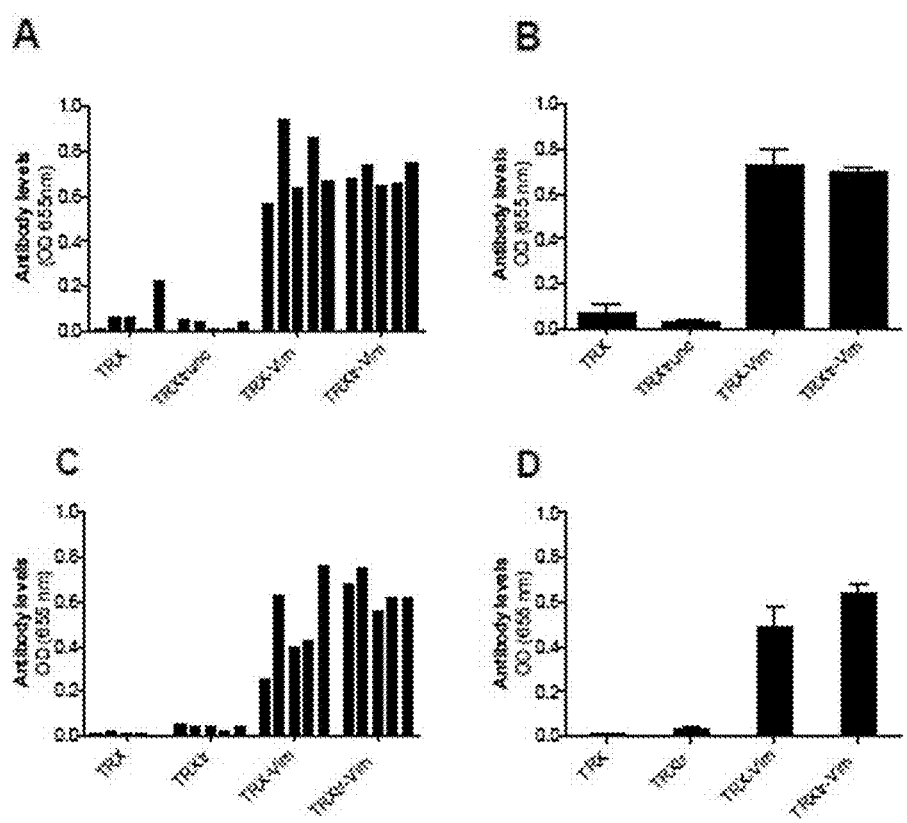
FIG. 5 shows in panels A)-D) anti-vimentin antibody levels in mice vaccinated with TRX, TRXtr, TRX-vimentin and TRXtr-vimentin. Panels A)-B) relate to a study wherein mice were vaccinated with the indicated fusion proteins and one week after the last booster antibody levels were measured in the sera. Afterwards mice were implanted with a B16-F10 melanoma cells. Panels C)-D) relate to a study wherein mice were vaccinated with the indicated fusion proteins and one week after the last booster antibody levels were measured in the sera. Afterwards mice were implanted with a CT26 carcinoma cells. In panels E)-H), anti-TRX antibody levels are shown for the different vaccinated fusion proteins. Panels E)-F) are based on experimental results that were obtained in the same study as panels A)-B) and panels G)-H) are based on experimental results obtained in the same study as panels C)-D). It clearly follows from these panels that anti-TRX antibody levels are decreased if TRXtr is employed as non-self fusion partner as compared to TRX.
Figure 5:
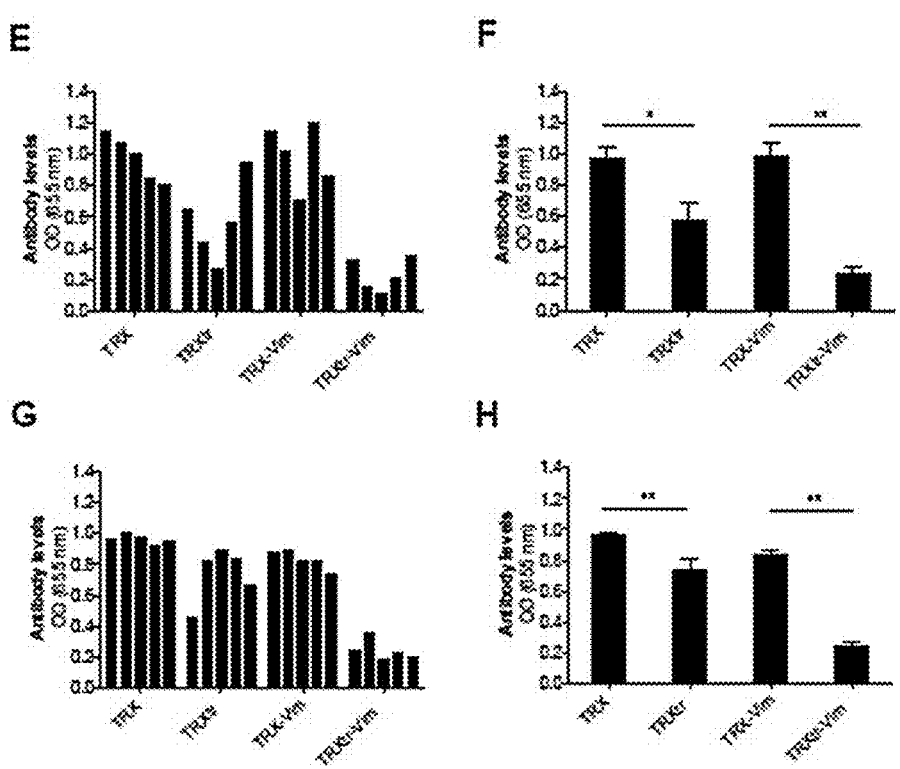
Figure 6:
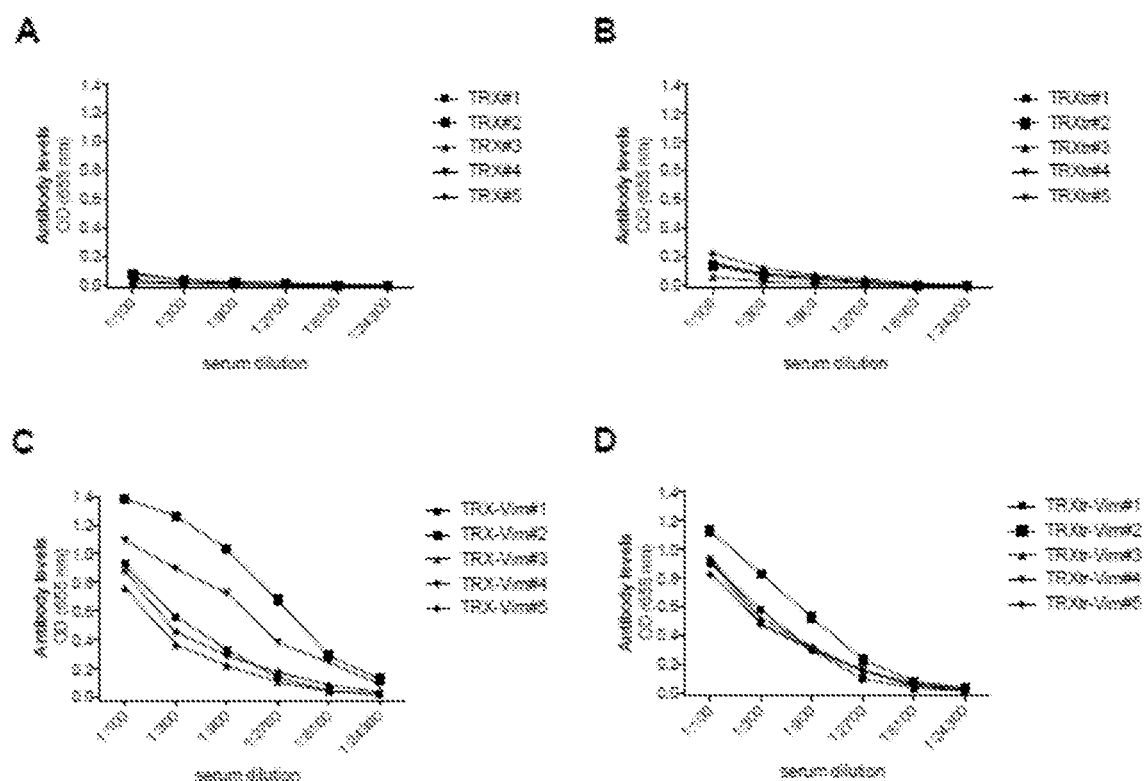
FIG. 6 shows in panels A)-D) anti-vimentin antibody titers per individual C57BL/6 mouse. Serum was diluted 1:100-1:24300 and optical density measured at 655 nm.

Anti-EDB antibody levels of vaccinated wild type C57BL/6 mice were assessed one week after the $4^{th}$ vaccination. We could observe that antibody levels against EDB in both studies were modest to low (mean $OD_{650\ nm}$=0.3410 (study I); 0.5732 (study II)) in the TRX-EDB vaccinated mice whereas the mice in the TRXtr-EDB, TFP-EDB and TFPv-EDB (mean OD=0.8775-1.212 for both studies) responded well to vaccination (FIG. 2, study I and study II). For USP-EDB there was a mixed response for the mice in the first study (mean OD=0.2743, study I, FIG. 2), whereas all mice in the study II responded well to vaccination (mean OD=1.192, study II). Since there was a large variation between the different study groups in the anti-EDB antibody levels observed, we made a dilution series to address the anti-EDB antibody titers. A sigmoidal curve should be observed for each dilutions series. The highest titers were present in the TRXtr-EDB, TFP-EDB and the USP-EDB group in the second study (FIG. 3). The reference group TRX-EDB had the lowest anti-EDB antibody titers of all groups tested (FIG. 3). In the control group vaccinated with TRX no anti-EDB should be present and therefore no anti-EDB antibody titers could be measured (FIG. 3, study II).

Antibody levels against vimentin in C57BL/6 mice and BALB/c mice were analyzed one week after the 4th vaccination. In both studies anti-vimentin antibody levels were comparable between the TRX-Vimentin (TRX-Vim) (mean $OD_{650\ nm}$=0.7341 (study I) (FIG. 5a); 0.4914 (study II) (FIG. 5c)) and TRXtr-Vimentin (TRXtr-Vim) (mean $OD_{650\ nm}$=0.6943 (study I) (FIG. 5a); 0.6445 (FIG. 5c)) groups. In the control groups, vaccinated with TRX or TRXtr no anti-Vimentin antibodies should be present and therefore mean $OD_{650\ nm}$ values were below 0.2000 (study I: 0.0072 (TRX); 0.0312 (TRXtr); study II: 0.0088 (TRX); 0.0383 (TRXtr)). We also determined the anti-Vimentin antibody titers per group in study I (FIG. 6a,d). Anti-vimentin antibody titers (dilution curves) were comparable between the TRX-Vim (FIG. 6c) and TRXtr-Vim (FIG. 6d) vaccinated mice. No anti-vimentin antibody titers were observed in the TRX (FIG. 6a) and TRXtr (FIG. 6b) control vaccinated mice.

The Antibody Response to the Self-Antigen can be Enhanced by Reducing the Size of the Foreign/Non-Self Part TRX In FIG. 4A average anti-EDB antibody levels are shown. It can be observed that in both studies the anti-EDB antibody levels are significantly (p=0.0357) increased in the TRXtr-EDB group compared to the TRX-EDB group. We also compared the anti-TRX antibody levels between the groups and found that the TRXtr-EDB group indeed shows a significantly (p=0.0317 (study I); p=0.0159 (study II)) reduced anti-TRX antibody level (FIG. 4b). Indeed antibody titers against TRX (the foreign/non-sef antigen) were reduced in mice vaccinated with TRXtr-EDB (p<0.001; at dilution 1:1000) compared to TRX or TRX-EDB (FIG. 4c).

The same observation was made after vaccination with TRXtr-Vimentin. The average anti-vimentin antibody levels were equal between the TRX-Vim and TRXtr-Vim groups (FIG. 5b,d), whereas the anti-TRX antibody levels were significantly reduced in TRXtr-Vim vaccinated mice (p=0.0079 (study I and II) FIG. 5e-h). In addition the anti-TRX antibody levels were significantly decreased in the TRXtr control mice vaccinated compared to TRX (p=0.0317 (study I); p=0.0079 (study II) FIG. 5f,h).

Figure 7:
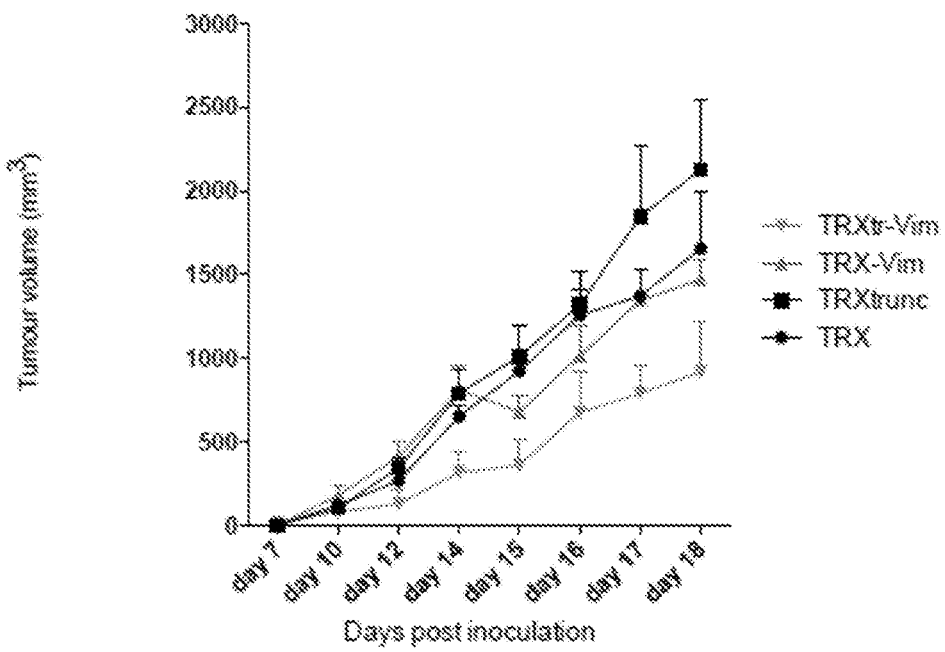
FIG. 7. Tumor volumes of mice vaccinated with TRXtr-Vim, TRX-Vim, TRXtr or TRX. A) Tumor volume per vaccinated group in days after inoculation with B16-F10 melanoma cells. B) Tumor volume of mice vaccinated with the different fusion proteins in days after inoculation with CT26 colon carcinoma cells. In the B16-F10 model the TRXtr-Vim fusion protein performed better than TRX-Vim.
Figure 7:
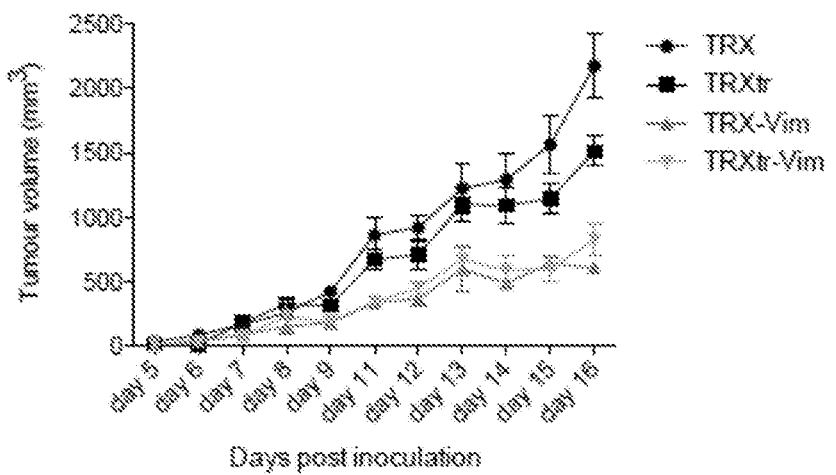

The Novel Fusion Partner TRXtr is Superior to TRX in the Production of Anti-Self Antibodies and the Inhibition of Tumor Growth Since we observed high anti-vimentin antibody titers in the TRXtr-Vim vaccinated group, but less antibodies against TRX we wanted to address if this would result in a better anti-tumor response. In addition we wanted to investigate if the anti-vimentin antibodies generated with the novel fusion protein construct TRXtr-Vimentin were functional and would be able to recognize vimentin in vivo and thereby inhibit tumor growth. Therefore we inoculated all mice subcutaneously with B16-F10 melanoma (study I) or CT26 colon carcinoma (study II) tumor cells, two weeks after the last booster. In both studies the construct TRXtr-Vimentin performed equal to the TRX-Vimentin construct (FIG. 5a,c), and high antibody levels against vimentin were induced. We observed a significant inhibition of tumor growth in the mice vaccinated with TRXtr-Vimentin (TRXtr-Vim) in both studies (p<0.001 (study I and II), FIG. 7a,b), whereas for the TRX-Vimentin (TRX-Vim) construct only a significant tumor growth inhibition could be observed in the CT26 model (p<0.001; FIG. 7b). These results indicate that by reducing the number of antibodies to the foreign bacterial part the amount of antibodies against the self-part can be enhanced and thereby the anti-tumor response. Indicating that less epitope suppression is correlated to an enhanced anti-tumor response.

The invention claimed is:

1. A method for eliciting an immune response in a mammalian subject in need of anti-tumor treatment, wherein said immune response is against a mammalian polypeptide the expression of which is associated with tumor angiogenesis, the method comprising
administering to the subject a therapeutically effective dose of a fusion polypeptide, the fusion polypeptide comprising said mammalian polypeptide and a foreign antigen,
wherein the foreign antigen comprises the sequence of SEQ ID NO:4,
wherein the foreign antigen is truncated form of SEQ ID NO:1 in which between 10 to 50 amino acids from the N-terminal side of SEQ ID NO:1 are removed, and
wherein the mammalian polypeptide is selected from the group consisting of vimentin (Vim), secreted frizzled-related protein 2 (Sfrp2), apelin (Apln), apelin receptor (Aplnr), human EGF receptor-2 (erbb2, HER2), erbb3 (HERS), fibrillin 2 (Fbn2), extra domain-B of fibronectin (ED-B), versican (Vcan), elastin microfibril interfacer 2 (Emilin2), CD99 antigen (CD99), tissue inhibitor of metalloproteinase 1 (Timp1), matrix metallopeptidase 14 (membrane-inserted) (Mmp14), laminin alpha 4 (Lama4), nidogen 2 (Nid2), member a (Clec14a), sulfatase 1 (Sulf1), insulin receptor (Insr).

2. The method of claim 1, wherein the mammalian polypeptide is vimentin (Vim).

3. The method of claim 1, wherein the mammalian polypeptide is secreted frizzled-related protein 2 (Sfrp2).

4. The method of claim 1, wherein the mammalian polypeptide is apelin (Apln).

5. The method of claim 1, wherein the mammalian polypeptide is apelin receptor (Aplnr).

6. The method of claim 1, wherein the mammalian polypeptide is human EGF receptor-2 (erbb2, HER2).

7. The method of claim 1, wherein the mammalian polypeptide is erbb3 (HER3).

8. The method of claim 1, wherein the mammalian polypeptide is fibrillin 2 (Fbn2).

9. The method of claim 1, wherein the mammalian polypeptide is extra domain-B of fibronectin (ED-B).

10. The method of claim 1, wherein the mammalian polypeptide is versican (Vcan).

11. A method for eliciting an immune response in a mammalian subject in need of anti-tumor treatment, wherein said immune response is against a mammalian polypeptide the expression of which is associated with tumor angiogenesis, the method comprising
administering to the subject a therapeutically effective dose of a fusion polypeptide, the fusion polypeptide comprising said mammalian polypeptide and a foreign antigen,
wherein the foreign antigen comprises the sequence of SEQ ID NO:4,
wherein the foreign antigen consists of a truncated immunogenic region of 58 to 70 consecutive amino acid residues of the protein of SEQ ID NO:1, and
wherein the mammalian polypeptide is selected from the group consisting of vimentin (Vim), secreted frizzled-related protein 2 (Sfrp2), apelin (Apln), apelin receptor (Aplnr), human EGF receptor-2 (erbb2, HER2), erbb3 (HERS), fibrillin 2 (Fbn2), extra domain-B of fibronectin (ED-B), versican (Vcan), elastin microfibril interfacer 2 (Emilin2), CD99 antigen (CD99), tissue inhibitor of metalloproteinase 1 (Timp1), matrix metallopeptidase 14 (membrane-inserted) (Mmp14), laminin alpha 4 (Lama4), nidogen 2 (Nid2), member a (Clec14a), sulfatase 1 (Sulf1), insulin receptor (Insr).

12. The method of claim 11, wherein the mammalian polypeptide is vimentin (Vim).

13. The method of claim 11, wherein the mammalian polypeptide is secreted frizzled-related protein 2 (Sfrp2).

14. The method of claim 11, wherein the mammalian polypeptide is apelin (Apln).

15. The method of claim 11, wherein the mammalian polypeptide is apelin receptor (Aplnr).

16. The method of claim 11, wherein the mammalian polypeptide is human EGF receptor-2 (erbb2, HER2).

17. The method of claim 11, wherein the mammalian polypeptide is erbb3 (HER3).

18. The method of claim 11, wherein the mammalian polypeptide is fibrillin 2 (Fbn2).

19. The method of claim 11, wherein the mammalian polypeptide is extra domain-B of fibronectin (ED-B).

20. The method of claim 11, wherein the mammalian polypeptide is versican (Vcan).

* * * * *

UNITED STATES PATENT AND TRADEMARK OFFICE
CERTIFICATE OF CORRECTION

PATENT NO. : 11,795,202 B2
APPLICATION NO. : 16/322786
DATED : October 24, 2023
INVENTOR(S) : Arjan Willem Griffioen, Elisabeth Johanna Maria Huijbers and Patrycja Nowak-Sliwinska It is certified that error appears in the above-identified patent and that said Letters Patent is hereby corrected as shown below:

In the Claims

Claim 1, Column 55, Line 33, delete "(HERS), fibrillin 2 (Fbn2), extra domain-B of fibronec-" and insert --(HER3), fibrillin 2 (Fbn2), extra domain-B of fibronec- --

Claim 11, Column 56, Line 31, delete "(HERS), fibrillin 2 (Fbn2), extra domain-B of fibronec-" and insert --(HER3), fibrillin 2 (Fbn2), extra domain-B of fibronec- --

Signed and Sealed this
Fifth Day of March, 2024

Katherine Kelly Vidal
*Director of the United States Patent and Trademark Office*